(12) United States Patent
Yamamoto et al.

(10) Patent No.: US 9,295,640 B2
(45) Date of Patent: Mar. 29, 2016

(54) PHARMACEUTICAL COMPOSITION FOR TREATING CANCER USING CARBONATE APATITE NANOPARTICLES

(71) Applicants: Hirofumi Yamamoto, Suita-shi, Osaka (JP); Toshihiro Akaike, Yokohama-shi, Kanagawa (JP); Masaki Mori, Suita-shi, Osaka (JP); Yuichiro Doki, Suita-shi, Osaka (JP); Xin Wu, Suita-shi, Osaka (JP); IJUNKAI, Sakai-Shi, Osaka (JP)

(72) Inventors: Hirofumi Yamamoto, Suita (JP); Hiroyuki Nakanishi, Sakai (JP); Toshihiro Akaike, Yokohama (JP); Masaki Mori, Suita (JP); Yuichiro Doki, Suita (JP); Xin Wu, Suita (JP)

(73) Assignees: Hirofumi Yamamoto, Suita-shi, Osaka (JP); Toshihiro Akaike, Yokohama-Shi, Kanagawa (JP); Masaki Mori, Suita-shi, Osaka (JP); Yuichiro Doki, Suita-shi, Osaka (JP); Xin Wu, Suita-shi, Osaka (JP); IJUNKAI, Sakai-Shi, Osaka (JP)

( * ) Notice: Subject to any disclaimer, the term of this patent is extended or adjusted under 35 U.S.C. 154(b) by 0 days.

(21) Appl. No.: 14/010,878

(22) Filed: Aug. 27, 2013

(65) Prior Publication Data
US 2014/0302145 A1 Oct. 9, 2014

(30) Foreign Application Priority Data

Nov. 28, 2012 (JP) .................................. 2012-260203

(51) Int. Cl.
*A61K 48/00* (2006.01)
*C12N 15/11* (2006.01)
*C07H 21/02* (2006.01)
*C07H 21/04* (2006.01)
*A61K 9/00* (2006.01)
*A61K 9/51* (2006.01)

(52) U.S. Cl.
CPC ............. *A61K 9/0019* (2013.01); *A61K 9/5115* (2013.01); *C12N 15/111* (2013.01); *C12N 2320/32* (2013.01)

(58) Field of Classification Search
USPC .......................... 536/23.1, 24.3, 24.5; 514/44
See application file for complete search history.

(56) References Cited

FOREIGN PATENT DOCUMENTS

| JP | 2005-075717 A | 3/2005 |
|---|---|---|
| WO | WO 2004-043495 A1 | 5/2004 |

OTHER PUBLICATIONS

Hossain et al. (Journal of Controlled Release, 2010 vol. 147:101-108).*
Wu et al. (PLOS One, Mar. 4, 2015, pp. 1-21).*

* cited by examiner

*Primary Examiner* — Terra Cotta Gibbs
(74) *Attorney, Agent, or Firm* — Knobbe, Martens, Olson & Bear, LLP

(57) ABSTRACT

A principal object of the present invention is to provide a pharmaceutical composition that can produce a high antitumor effect by efficiently delivering a drug with antitumor activity to tumor tissues with the aid of carbonate apatite nanoparticles. The present invention provides a pharmaceutical composition including carbonate apatite nanoparticles with an average particle size of at most 50 nm containing a drug with antitumor activity and a pharmacologically acceptable solvent in which the carbonate apatite nanoparticles containing the drug are dispersed.

12 Claims, 46 Drawing Sheets

PHARMACEUTICAL COMPOSITION FOR TREATING CANCER USING CARBONATE APATITE NANOPARTICLES

BACKGROUND OF THE INVENTION

Field of the Invention

The present invention relates to a pharmaceutical composition that can produce a high antitumor effect by efficiently delivering a drug with antitumor activity to tumor tissues with the aid of carbonate apatite nanoparticles. The present invention also relates to a method of treating cancer with such a pharmaceutical composition and to a method for manufacturing such a pharmaceutical composition.

Reference To Sequence Listing

A Sequence Listing submitted as an ASCII text file via EFS-Web is hereby incorporated by reference in accordance with 35 U.S.C. §1.52(e). The name of the ASCII text file for the Sequence Listing is 18283670_1.txt, the date of creation of the ASCII text file is Jun. 24, 2014, and the size of the ASCII text file is 968 bytes.

Description of Related Art

Carbonate apatite has a chemical structure in which the hydroxyl group (OH—) of hydroxy apatite ($Ca_{10}(PO_4)_6(OH)_2$) is partially replaced by a carbonic acid group ($CO_3^{2-}$). WO2004/043495 discloses that carbonate apatite is used as a carrier for introducing substances into cells. More specifically, WO2004/043495 discloses a cell transfection agent, which includes complex particles including a desired substance and a calcium phosphate-based material, wherein when the pH of the complex particles is changed from 8.0 to 6.0, at least 50% of the complex particles present at a pH of 8.0 can dissolve within a certain period of time after its pH is changed to 6.0.

JP 2005-75717 A states that carbonate apatite has a problem in that its primary particles have a relatively small size but have strong aggregability, while its secondary particles has a relatively large size, and discloses, as means for solving the problem, a method of controlling the amount of carbonic acid in an aqueous solution containing phosphoric acid and calcium. Even based on these conventional techniques, however, a further improvement is necessary for practical use of carbonate apatite as a carrier for delivery of substances into cells or a living body.

Drugs with antitumor activity are generally used through systemic administration such as intravascular administration, subcutaneous administration, or intramuscular administration. Unfortunately, the conventional type of carbonate apatite has strong aggregability and relatively large secondary particle sizes as mentioned above, and does not have a particle size suitable for movement in blood vessels. At present, there has been no carbonate apatite that can be practically used as a carrier for systemic administration of drugs.

Specifically, the efficiency of conventional carbonate apatite-mediated uptake of substances into cells is not always satisfactory, and there is a room for further improvement. To administer carbonate apatite to animals by intraarterial or intravenous injection, it is necessary to dissolve carbonate apatite in a solution suitable for the administration, such as a saline solution. However, there is the following problem. When centrifugation is performed in the process of replacing the solvent used in forming carbonate apatite by another solvent such as a saline solution, carbonate apatite can aggregate to form large clusters unsuitable for administration (particularly, administration into blood). Thus, there is a technical barrier to use of carbonate apatite nanoparticles for practical manufacture of pharmaceutical compositions for treating cancer.

SUMMARY OF THE INVENTION

Thus, a principal object of the present invention is to provide a pharmaceutical composition that can produce a high antitumor effect by efficiently delivering a drug with antitumor activity to tumor tissues with the aid of carbonate apatite nanoparticles.

As a result of earnest studies to solve the problems, the inventors have made the following findings.

(1) When a conventional type of carbonate apatite is subjected to an ultrasonic vibration treatment, carbonate apatite nanoparticles with an average particle size of 50 nm or less can be prepared. The use of such carbonate apatite nanoparticles can significantly increase the efficiency of uptake of substances into cells and can make it possible to introduce a large amount of substances in a shorter time, as compared with the use of a conventional type of carbonate apatite particles.

(2) When the carbonate apatite nanoparticles are used in intraarterially or intravenously administering a drug to a living body, the drug can be efficiently accumulated in and leached to tumor tissue regions far from blood vessels without an increase in the accumulation of the drug in liver and kidney, as compared with DDS according to conventional techniques.

(3) When carbonate apatite nanoparticles containing a drug with antitumor activity are intravenously administered to tumor model mice, a dramatically improved antitumor effect can be produced with a smaller amount of the drug with antitumor activity as compared with conventional techniques.

(4) When albumin is added to carbonate apatite particles and the resulting mixture is subjected to an ultrasonic vibration treatment, the particle size can be further reduced, and aggregation of the particles can be effectively suppressed.

(5) Carbonate apatite nanoparticles with an average particle size of 50 nm or less, which are impossible to obtain with such general size-reducing means as a Polytron homogenizer (POLYTRON PT3000), a vortex mixer, or an ultrasonic crusher (ULTRASONIC DISRUPTOR TOMYUD-201), are conveniently and reliably obtained by a process including placing carbonate apatite particles in an appropriate vessel and applying to ultrasonic waves to the vessel while allowing the vessel to float in the water bath of an ultrasonic cleaner, which is generally used for cleaning test tubes and so on.

Based on these findings, the inventors have made further investigations and improvements, and have finally accomplished the present invention.

Specifically, the present invention provides the following aspects.

Item 1. A pharmaceutical composition, including: carbonate apatite nanoparticles with an average particle size of at most 50 nm containing a drug with antitumor activity; and a pharmacologically acceptable solvent in which the carbonate apatite nanoparticles containing the drug are dispersed.

Item 2. The pharmaceutical composition according to item 1, wherein the solvent is a saline solution.

Item 3. The pharmaceutical composition according to item 1, wherein the carbonate apatite nanoparticles are a product obtained by subjecting, to an ultrasonic vibration treatment, carbonate apatite particles containing the drug with antitumor activity.

Item 4. The pharmaceutical composition according to item 1, wherein the drug is at least one selected from the group consisting of siRNA, miRNA, and antisense RNA.

Item 5. The pharmaceutical composition according to item 1, further including albumin.

Item 6. A method of treating cancer, including the step of administering, to a patient with cancer, a pharmaceutical composition including carbonate apatite nanoparticles with an average particle size of at most 50 nm containing a drug with antitumor activity and a pharmacologically acceptable solvent in which the carbonate apatite nanoparticles containing the drug are dispersed.

Item 7. The method according to item 6, wherein the pharmaceutical composition is administered by intravascular administration, subcutaneous administration, or intramuscular administration.

Item 8. The method according to item 6, wherein the solvent is a saline solution.

Item 9. The method according to item 6, wherein the carbonate apatite nanoparticles are a product obtained by subjecting, to an ultrasonic vibration treatment, carbonate apatite particles containing the drug with antitumor activity.

Item 10. The method according to item 6, wherein the drug is at least one selected from the group consisting of siRNA, miRNA, and antisense RNA.

Item 11. The method according to item 6, wherein the pharmaceutical composition further includes albumin.

Item 12. A method for manufacturing the pharmaceutical composition according to item 1, including the steps of:
preparing a dispersion including carbonate apatite particles containing a drug with antitumor activity and a pharmacologically acceptable solvent in which the particles are dispersed; and
subjecting the dispersion to an ultrasonic vibration treatment.

The use of the pharmaceutical composition of the present invention makes possible remarkably efficient transfection of a drug with antitumor activity into tumor cells as compared with the use of a conventional type of carbonate apatite particles. Particularly when a nucleic acid such as siRNA or miRNA is used as a drug with antitumor activity, the present invention can dramatically improve the efficiency of delivery of the nucleic acid into cells as compared with conventional cell transfection agents.

In addition, even when used through systemic administration such as intravascular, subcutaneous, or intramuscular administration, the pharmaceutical composition of the present invention is less accumulated in such tissues as liver, kidney, and spleen than conventional ones (liposome and atelocollagen), but allows significant accumulation into tumor tissues and significant leaching, so that it can efficiently produce a cancer treatment effect.

In addition, it has been found that the administration of the carbonate apatite nanoparticles for use in the present invention does not cause any abnormalities of body weight or any abnormalities in biochemical examination of blood and histological examination. Thus, the carbonate apatite nanoparticles are considered to have high safety and a very high potential for practical use.

To form the pharmaceutical composition of the present invention, albumin may be used in combination with the carbonate apatite nanoparticles with a specific particle size containing a drug with antitumor activity, so that the size of the carbonate apatite nanoparticles can be further reduced or reaggregation of the carbonate apatite nanoparticles can be suppressed.

BRIEF DESCRIPTION OF THE DRAWINGS

FIG. 1-2 shows the results of the measurement of the particle size and morphology of carbonate apatite nanoparticles (sCA(2) particles) of Example 1 with a scanning probe microscope;

FIG. 1-3 shows the results of the measurement of the particle size and morphology of siRNA-containing carbonate apatite nanoparticles of Example 1 (sCA-siRNA) with a scanning probe microscope;

FIG. 2 shows the results of the measurement of the particle size and morphology of a conventional type of carbonate apatite particles of Comparative Example 1;

FIG. 3-1 is a photograph showing the results of the measurement of uptake of siRNA-containing carbonate apatite nanoparticles into KM12sm cells;

FIG. 3-2 shows the results of the fluorescence intensity measurement of uptake of siRNA-containing carbonate apatite nanoparticles into KM12sm cells;

FIG. 4-1 is a photograph showing the results of the measurement of uptake of siRNA-containing carbonate apatite nanoparticles into 22Rv1 cells;

FIG. 4-2 shows the results of the fluorescence intensity measurement of uptake of siRNA-containing carbonate apatite nanoparticles into 22Rv1 cells;

FIG. 5-1 is a photograph showing the results of the measurement of uptake of siRNA-containing carbonate apatite nanoparticles into FaDu cells;

FIG. 5-2 shows the results of the fluorescence intensity measurement of uptake of siRNA-containing carbonate apatite nanoparticles into FaDu cells;

FIG. 10-1 is a photograph showing the results of high-resolution analysis of uptake of siRNA-containing carbonate apatite nanoparticles into HCT116 cells;

FIG. 10-2 is a photograph showing the results of high-resolution analysis of uptake of siRNA-containing Lipofectamine into HCT116 cells;

FIG. 12-1 shows whether or not siRNA-containing carbonate apatite nanoparticles are accumulated in the liver;

FIG. 12-2 shows whether or not siRNA-containing carbonate apatite nanoparticles are accumulated in the kidney;

FIG. 13-1 shows a distribution of siRNA-containing carbonate apatite nanoparticles in tumor tissue (HCT116) blood vessels and surrounding tissues;

FIG. 13-2 shows a distribution of siRNA-containing carbonate apatite nanoparticles in tumor tissues (HT29);

FIG. 13-3 shows the results of fluorescence intensity-based analysis of a distribution of siRNA-containing carbonate apatite nanoparticles in tumor tissues (HCT116);

FIG. 15-1 shows whether or not carbonate apatite nanoparticles are accumulated in the liver of a tumor-bearing model mouse 4 hours after intravenous injection of siRNA-containing carbonate apatite nanoparticles;

FIG. 15-2 shows whether or not carbonate apatite nanoparticles are accumulated in the liver of a tumor-bearing model mouse 12 hours after intravenous injection of siRNA-containing carbonate apatite nanoparticles;

FIG. 15-3 shows (in an enlarged manner) whether or not carbonate apatite nanoparticles are accumulated in the liver of a tumor-bearing model mouse 4 hours after intravenous injection of siRNA-containing carbonate apatite nanoparticles;

FIG. 16-1 shows whether or not carbonate apatite nanoparticles are accumulated in the spleen of a tumor-bearing model mouse 4 hours after intravenous injection of siRNA-containing carbonate apatite nanoparticles;

FIG. 16-2 shows whether or not carbonate apatite nanoparticles are accumulated in the spleen of a tumor-bearing model mouse 12 hours after intravenous injection of the siRNA-containing carbonate apatite nanoparticles;

FIG. 17-1 shows whether or not carbonate apatite nanoparticles are accumulated in the kidney of a tumor-bearing model mouse 4 hours after intravenous injection of siRNA-containing carbonate apatite nanoparticles;

FIG. 17-2 shows whether or not carbonate apatite nanoparticles are accumulated in the kidney of a tumor-bearing model mouse 12 hours after intravenous injection of siRNA-containing carbonate apatite nanoparticles;

DETAILED DESCRIPTION OF PREFERRED EMBODIMENTS

Figure 1:
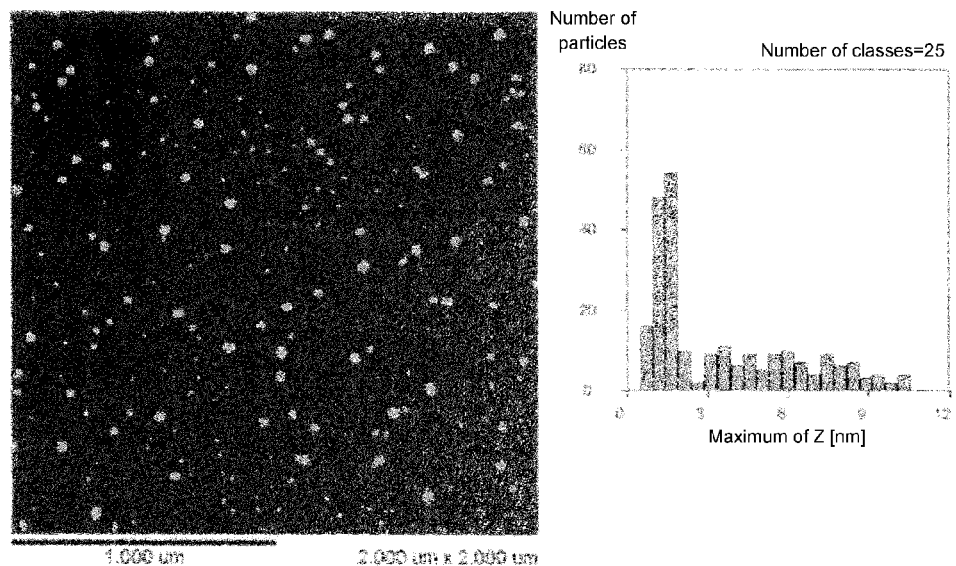
FIG. 1-1 shows the results of the measurement of the particle size and morphology of carbonate apatite nanoparticles (sCA(1) particles) of Example 1 with a scanning probe microscope.

The pharmaceutical composition of the present invention includes carbonate apatite nanoparticles with an average particle size of 50 nm or less containing a drug with antitumor activity and a pharmacologically acceptable solvent in which the carbonate apatite nanoparticles containing the drug are dispersed. Hereinafter, the present invention will be described in detail.

1. Composition of Pharmaceutical Composition

"Carbonate apatite" used in the present invention may have a known composition. Carbonate apatite may have a chemical structure in which the hydroxyl group (OH—) of hydroxy apatite ($Ca_{10}(PO_4)_6(OH)_2$) is partially replaced by a carbonic acid group ($CO_3^{2-}$), and such a chemical structure can be represented by the general formula: $Ca_{10-m}X_m(PO_4)_6(CO_3)_{1-n}Y_n$. In the formula, X may be an element capable of partially replacing Ca in the carbonate apatite, examples of which include Sr, Mn, and rare-earth elements. In the formula, m is generally a positive number of 0 to 1, preferably 0 to 0.1, more preferably 0 to 0.01, even more preferably 0 to 0.001. Y is a unit capable of partially replacing $CO_3$ in the carbonate apatite, examples which include OH, F, and Cl. In the formula, n is generally a positive number of 0 to 0.1, preferably 0 to 0.01, more preferably 0 to 0.001, even more preferably 0 to 0.0001.

In the present invention, carbonate apatite is used in the form of nanoparticles with an average particle size of 50 nm or less. Controlling the average particle size of the carbonate apatite nanoparticles to 50 nm or less makes it possible to produce the desired advantageous effects set forth above. The lower limit of the average particle size of the carbonate apatite nanoparticles is not limited as long as the desired effects set forth above can be obtained. For example, the average particle size of the carbonate apatite nanoparticles may have a lower limit of 1 nm or more, preferably 3 nm or more, more preferably 5 nm or more. On the other hand, the upper limit of the average particle size of the carbonate apatite nanoparticles is more preferably 40 nm or less, even more preferably 30 nm or less, further more preferably 20 nm or less, still more preferably 10 nm or less.

As described below in EXAMPLES, the average particle size of the carbonate apatite nanoparticles can be measured by observation using a scanning probe microscope. Before the measurement of the average particle size, the site to be measured should be observed with a CCD camera. As a result, when large particles clearly unsuitable for measurement with a scanning probe microscope are observed (for example, particles with diameters of 5 μm or more), such large particles will be removed from the measurement. As used herein, the term "particle size" means the size of independent particles that can be individually identified when measured with a scanning probe microscope. Therefore, when a plurality of particles form an aggregate, such an aggregate should be counted as a single particle.

The "drug with antitumor activity" used in the present invention may be of any type having antitumor activity and being usable for cancer treatment, examples of which include anticancer agents, nucleic acids with antitumor activity, proteins with antitumor activity, and other antitumor drugs.

Examples of anticancer agents include alkylating agents such as cyclophosphamide hydrate, ifosfamide, thiotepa, busulfan, melphalan, nimustine hydrochloride, ranimustine, dacarbazine, and temozolomide; antimetabolites such as methotrexate, pemetrexed sodium hydrate, fluorouracil, doxifluridine, capecitabine, tegafur, cytarabine, gemcitabine hydrochloride, fludarabine phosphate, nelarabine, cladribine, and levofolinate calcium; antibiotics such as doxorubicin hydrochloride, daunorubicin hydrochloride, pirarubicin, epirubicin hydrochloride, idarubicin hydrochloride, aclarubicin hydrochloride, amrubicin hydrochloride, mitoxantrone hydrochloride, mitomycin C, actinomycin D, bleomycin hydrochloride, peplomycin hydrochloride, zinostatin stimalamer, and calicheamicin; microtubule inhibitors such as vincristine sulfate, vinblastine sulfate, vindesine sulfate, and paclitaxel; aromatase inhibitors such as anastrozole, exemestane, letrozole, and fadrozole hydrochloride hydrate; platinum agents such as cisplatin, carboplatin, nedaplatin, and oxaliplatin; topoisomerase inhibitors such as irinotecan hydrochloride hydrate, nogitecan hydrochloride, etoposide, and sobuzoxane; adrenocorticosteroids such as prednisolone and dexamethasone; thalidomide and a derivative thereof such as lenalidomide; and a protease inhibitor such as bortezomib. These anticancer agents may be used alone or in combination of two or more.

Examples of nucleic acids with antitumor activity include DNA, RNA, antisense RNA, siRNA, and miRNA. Examples of the siRNA include those targeting an apoptosis inhibiting protein such as survivin. Examples of the miRNA include miR340, miR542-3p, miR34a, and miR4685. These nucleic acids may be used alone or in combination of two or more.

Examples of proteins with antitumor activity include antibodies and fragments thereof.

Among these drugs, nucleic acids with antitumor activity are preferred, and siRNA, miRNA, antisense RNA, and antisense DNA each with antitumor activity are more preferred.

In the present invention, drugs with antitumor activity may be used alone or in combination of two or more.

In the pharmaceutical composition of the present invention, the carbonate apatite nanoparticles with an average particle size of 50 nm or less contain the drug with antitumor activity. As used herein, the term "contain" means that the drug with antitumor activity is attached in any mode to the carbonate apatite nanoparticles with an average particle size of 50 nm or less. Examples of such an attached state include states in which the drug is attached to the inside and/or the outside of the carbon apatite nanoparticles with an average particle size of 50 nm or less. When the carbonate apatite nanoparticles with an average particle size of 50 nm or less containing the drug with antitumor activity are administered to a living body, the drug remains attached to the carbonate apatite nanoparticles until the drug is transfected into tumor cells. When transferred into tumor cells, the drug is released from the carbon apatite nanoparticles upon a change in pH to produce the desired antitumor effect in the tumor cells.

In the pharmaceutical composition of the present invention, the amount of the drug with antitumor activity contained by the carbonate apatite nanoparticles with an average particle size of 50 nm or less may be appropriately set depending on the type of the drug or other factors. In general, carbonate apatite can contain about 0.02 to about 1 part by weight of an anticancer agent per 100 parts by weight of the total amount of added anticancer agent, and carbonate apatite can contain about 30 to about 50 parts by weight of a nucleic acid such as siRNA per 100 parts by weight of the total amount of added nucleic acid. The amount of the drug with antitumor activity to be contained by the carbonate apatite nanoparticles with an average particle size of 50 nm or less may be appropriately set in such a range.

The concentration of the carbonate apatite nanoparticles in the pharmaceutical composition of the present invention is not limited and may be appropriately set so as to provide the dose mentioned below, taking into account the administration technique or other factors. For example, the concentration of the carbonate apatite nanoparticles may be from $1 \times 10^8$ to $1 \times 10^{12}$/ml, preferably from $1 \times 10^9$ to $1 \times 10^{11}$/ml, more preferably from $1 \times 10^{10}$ to $5 \times 10^{10}$/ml, even more preferably $3 \times 10^9$ to $3 \times 10^{10}$/ml, further more preferably from $6 \times 10^9$ to $1.5 \times 10^{10}$/ml.

In the pharmaceutical composition of the present invention, the pharmacologically acceptable solvent may be of any type as long as the carbonate apatite nanoparticles can be dispersed in it. Examples of such a solvent include a saline solution and other buffer solutions.

The pharmaceutical composition of the present invention may also contain albumin. The addition of albumin makes it possible to further reduce the particle size of the carbonate apatite nanoparticles or to suppress reaggregation of the particles.

The content of albumin in the pharmaceutical composition of the present invention is typically, but not limited to, 0.1 to 500 mg/ml, preferably 1 to 100 mg/ml, more preferably 1 to 10 mg/ml, to make the carbonate apatite nanoparticles fine and/or to suppress the reaggregation.

2. Method for Manufacturing the Pharmaceutical Composition

Specifically, a method for manufacturing the pharmaceutical composition of the present invention may include the steps of: preparing a dispersion including carbonate apatite particles containing a drug with antitumor activity and a pharmacologically acceptable solvent in which the particles are dispersed; and subjecting the dispersion to an ultrasonic vibration treatment.

Carbonate apatite particles containing a drug with antitumor activity can be obtained by a known method. For example, carbonate apatite particles containing a drug with antitumor activity can be produced by preparing an aqueous solution containing calcium ions, phosphate ions, hydrogencarbonate ions, and the drug with antitumor activity and incubating the solution. The concentrations of each type of ions and the drug with antitumor activity in the aqueous solution are not limited as long as carbonate apatite particles can be formed containing the drug with antitumor activity, and may be appropriately set taking into account the following.

The concentration of calcium ions in the aqueous solution is generally 0.1 mM or more, preferably 0.5 mM or more, more preferably 1 mM or more. The upper limit of the calcium ion concentration is generally 1 M or less, preferably 100 mM or less, more preferably 10 mM or less.

The concentration of phosphate ions in the aqueous solution is generally 0.1 mM or more, preferably 0.5 mM or more, more preferably 1 mM or more. The upper limit of the phosphate ion concentration is generally 1 M or less, preferably 100 mM or less, more preferably 10 mM or less.

The concentration of hydrogencarbonate ions in the aqueous solution is generally 1.0 mM or more, preferably 5 mM or more, more preferably 10 mM or more. The upper limit of the hydrogencarbonate ion concentration is generally 10 M or less, preferably 1 M or less, more preferably 100 mM or less.

Sources of calcium ions, phosphate ions, and hydrogencarbonate ions may each be of any type capable of supplying the ions to the aqueous solution. For example, salts of these ions may be added as ion sources to the aqueous solution. More specifically, $CaCl_2$ may be used as a calcium ion source, $NaH_2PO_4 \cdot 2H_2O$ may be used as a phosphate ion source, and $NaHCO_3$ may be used as a carbonate ion source.

The concentration of the drug with antitumor activity in the aqueous solution can be appropriately set depending on the type of the drug or other factors. When an anticancer agent is used, for example, the concentration of the anticancer agent in the aqueous solution may be 10 to 1,000 µM, 20 to 500 µM, or 40 to 200 µM. When a nucleic acid such as siRNA is used, the concentration of the nucleic acid in the aqueous solution may be 0.1 to 1,000 nM, 0.5 to 500 nM, or 1 to 200 nM.

The respective ion sources and the drug with antitumor activity may be mixed in any order, and the aqueous solution may be prepared in any mixing order as long as carbonate apatite particles containing the drug with antitumor activity can be obtained. For example, the aqueous solution can be prepared by a process including preparing a first solution containing calcium ions and the drug with antitumor activity, separately preparing a second solution containing phosphate ions and hydrogencarbonate ions, and mixing the first and second solutions.

The aqueous solution for the preparation of carbonate apatite particles containing the drug with antitumor activity may contain other components than the respective ion sources and the drug with antitumor activity in a range where the object is not impaired. For example, fluoride ions, chloride ions, Sr, Mn, or other species may be added to the aqueous solution so that in the composition, such a species can partially replace Ca or $CO_3$ in carbonate apatite. The added amount of fluoride ions, chloride ions, Sr, or Mn is preferably in a range where there is no significant effect on the pH-solubility of the formed complex particles or the particle size range of the formed complex particles. The aqueous solution for the preparation of carbonate apatite particles containing the drug with antitumor activity may also be prepared using any of various cell culture media or buffers.

Carbonate apatite particles containing the drug with antitumor activity can be obtained by incubating, for a certain period of time, the aqueous solution containing each type of ions and the drug with antitumor activity with the pH of the solution adjusted in the range of 6.0 to 9.0. In the process of forming carbonate apatite particles containing the drug with antitumor activity, the pH of the aqueous solution is preferably 7.0 or more, more preferably 7.1 or more, even more preferably 7.2 or more, further more preferably 7.3 or more, still more preferably 7.4 or more, most preferably 7.5 or more. On the other hand, in the process of forming carbonate apatite particles, the pH of the aqueous solution is preferably 8.5 or less, more preferably 8.0 or less.

In the process of forming carbonate apatite particles containing the drug with antitumor activity, the temperature condition of the aqueous solution is generally 10° C. or higher, preferably 25° C. or higher, more preferably 37° C. or higher. On the other hand, the upper limit of the temperature condition is generally 80° C. or lower, preferably 70° C. or lower.

To form carbonate apatite particles containing the drug with antitumor activity, the aqueous solution is generally incubated for a time period of 1 minute to 24 hours, preferably 10 minutes to 1 hour. For example, whether or not such particles are formed can be checked by observation with a microscope.

In this way, a dispersion is formed which contains carbonate apatite particles containing the drug with antitumor activity. In such a dispersion, the carbonate apatite particles have an average particle size of more than 50 nm. Thus, the carbonate apatite particles are subjected to a size-reducing treatment so that they can have an average particle size of 50 nm or less. Thus, the pharmaceutical composition of the present invention can be obtained.

As described above, carbonate apatite particles containing the drug with antitumor activity can be obtained from a solution of the respective ion source materials and the drug with antitumor activity in a solvent such as water, a medium, or a buffer. The dispersion of carbonate apatite particles obtained in this way is not always suitable for administration (intravascular administration) to a living body in terms of osmotic pressure, buffer capacity, sterility, or other properties. Therefore, the solvent in the dispersion of the carbonate apatite particles containing the drug with antitumor activity should be replaced by another solvent suitable for administration to a living body (such as a saline solution). For this purpose, it is generally necessary to perform a process including separating the carbonate apatite particles from the solvent by centrifugation, collecting the particles, and replacing the solvent by another solvent. If such a process is performed, however, the carbonate apatite particles can aggregate together to form large particles, so that the particles can rather change into a state unsuitable for administration to a living body. Thus, the dispersion medium in which the carbonate apatite particles have aggregated is replaced by a pharmacologically acceptable solvent suitable for administration to a living body, and then a size-reducing treatment is performed as described below, which makes it possible to obtain a pharmaceutical composition in which carbonate apatite nanoparticles with an average particle size of 50 nm or less containing the drug with antitumor activity are dispersed in the pharmacologically acceptable solvent.

The method for size-reducing the carbonate apatite particles containing the drug with antitumor activity to an average particle size of 50 nm or less is preferably an ultrasonic vibration treatment. As used herein, the term "ultrasonic vibration treatment" does not refer to a treatment in which ultrasonic waves are applied to the specimen by bringing the specimen into direct contact with an ultrasonic vibrator of an ultrasonic crusher, a homogenizer, or other means for use in what is called cell-disruption or other procedures, but refers to a treatment using an ultrasonic cleaner having an ultrasonic vibrator and a cleaning tank integrated together generally for use in cleaning precision instruments, test tubes, or other objects. The ultrasonic vibration treatment means a process including placing a liquid (such as water) in the cleaning tank (water tank) of an ultrasonic cleaner, allowing a vessel (such as a plastic tube) to float in the liquid, wherein the vessel contains the pharmacologically acceptable solvent dispersion of the carbonate apatite particles containing the drug with antitumor activity, and applying ultrasonic waves to the dispersion through the liquid in a similar manner to cleaning precision instruments. This process makes it possible to conveniently and efficiently reduce the size of the carbonate apatite particles to 50 nm or less.

The ultrasonic vibration treatment may be performed using any device capable of applying ultrasonic vibration indirectly to a vessel containing the carbonate apatite particles through a solvent such as water, like the ultrasonic cleaner. In view of versatility and good handleability, an ultrasonic cleaner having an ultrasonic vibrator and a thermostatic tank is preferably used.

The ultrasonic vibration treatment may be performed under any conditions as long as the average particle size can be controlled to 50 nm or less. For example, the temperature of the water tank may be appropriately selected from temperatures ranging from 5 to 45° C., preferably from 10 to 35° C., more preferably from 20 to 30° C. For example, the high-frequency power in the ultrasonic vibration treatment may be appropriately set in the range of 10 to 500 W, preferably 20 to 400 W, more preferably 30 to 300 W, even more preferably 40 to 100 W. The oscillating frequency is generally from 10 to 60 Hz, preferably from 20 to 50 Hz, more preferably from 30 to 40 Hz. For example, the time period of the ultrasonic vibration treatment may be appropriately set in the range of 30 seconds to 30 minutes, preferably 1 to 20 minutes, more preferably 3 to 10 minutes.

In the process of performing the ultrasonic vibration treatment, any type of vessel may be used to contain the dispersion containing carbonate apatite particles containing the drug with antitumor activity as long as the average size of the particles can be reduced to 50 nm or less. Such a vessel may be appropriately selected depending on the volume of the dispersion or the intended use of the dispersion. For example, a plastic tube with a volume of 1 to 1,000 ml may be used.

As described above, the ultrasonic vibration treatment is preferably performed after albumin is added to the dispersion containing carbonate apatite particles containing the drug with antitumor activity. This is because when the ultrasonic vibration treatment is performed in an environment where carbonate apatite particles coexist with albumin, carbonate apatite nanoparticles with smaller sizes can be obtained, and reaggregation of particles can also be suppressed. The amount of albumin added to the dispersion containing carbonate apatite particles containing the drug with antitumor activity may be as described above in the section "1. Composition of pharmaceutical composition."

3. Mode of Use of Pharmaceutical Composition

The pharmaceutical composition of the present invention can produce an antitumor effect by means of the drug with antitumor activity contained by the carbonate apatite nanoparticles with an average particle size of 50 nm or less. Thus, the pharmaceutical composition of the present invention can be used as a therapeutic agent for cancer.

The pharmaceutical composition of the present invention may be administered by any method. It may be administered systemically or locally. The pharmaceutical composition of the present invention is remarkably advantageous in that even when administered systemically, the drug with antitumor activity can be specifically accumulated in or leached to tumor tissues while prevented from being accumulated in such tissues as liver, kidney, and spleen. Thus, systemic administration is preferred. Specifically, systemic administration may be intravascular (intraarterial or intravenous) administration, subcutaneous administration, subcutaneous administration, or the like, and is preferably intravascular administration, more preferably intraarterial or intravenous administration. It will be understood that intravascular administration is intended to include not only intravascular injection but also continuous infusion.

The dose of the pharmaceutical composition of the present invention is appropriately determined depending on the type of the drug with antitumor activity and the sex, age, condition, and other characteristics of the patient, and thus cannot be uniquely determined. For example, the pharmaceutical composition of the present invention may be administered in a dose containing about 10 to about 30 $mg/m^2$ (body surface area) of the carbonate apatite nanoparticles with an average particle size of 50 nm or less per day.

The timing of the administration of the pharmaceutical composition of the present invention is not restricted. However, aggregation of the carbonate apatite nanoparticles should be avoided before the administration. For this purpose, it is preferable to administer the pharmaceutical composition of the present invention quickly after the ultrasonic vibration treatment. For example, the pharmaceutical composition of the present invention is preferably administered within 1 minute, more preferably within 30 seconds after the ultrasonic vibration treatment. However, when albumin is added to suppress the aggregation of the carbonate apatite nanoparticles as described above, the pharmaceutical composition of the present invention can be administered several minutes to several tens of minutes after the ultrasonic vibration treatment.

EXAMPLES

Hereinafter, the present invention will be described with reference to examples. It will be understood that the examples described below are not intended to limit the scope of the present invention.

Example 1

Production of Carbonate Apatite Nanoparticles (Sonicated Carbonate Apatite (sCA))

(1) Production of Carbonate Apatite Nanoparticles (sCA) Using DMEM Solution

To 100 ml of distilled water were added 1.35 g of DMEM powder and 0.37 g of $NaHCO_3$ sequentially, and dissolved completely. The pH of the solution was adjusted to 7.5 with 1N HCl. The DMEM solution (100 ml) was filtered through a 0.2 µm size filter, and 4 µl of $CaCl_2$ (1 M) was mixed per 1 ml of the DMEM solution. The resulting mixture was incubated in a water bath at 37° C. for 30 minutes. Subsequently, the mixture was centrifuged at 15,000 rpm for 5 minutes. The resulting pellet was dispersed in distilled water, a cell culture liquid, or an aqueous solution capable of being administered to cells or a living body, such as a saline solution, so that a dispersion of carbonate apatite particles was obtained. The dispersion was subjected to an ultrasonic vibration treatment for 10 minutes, so that carbonate apatite nanoparticles (hereinafter referred to as "sCA(1) particles") were obtained. A plastic vessel containing the dispersion of carbonate apatite particles was allowed to float in water at 20° C. placed in a water bath having an ultrasonic vibration function, and the ultrasonic vibration treatment was performed under the conditions of a high-frequency power of 55 W and an oscillating frequency of 38 kHz for 10 minutes using the water bath. When the particle size was measured with a microscope, the sCA(1) particles were dispersed in distilled water after the centrifugation. When the dispersion was used for experiments with cells, the dispersion was prepared by dispersing the sCA(1) particles in a DMEM solution without or after the centrifugation. When the dispersion was used for experiments with animals, the dispersion was prepared by dispersing the sCA(1) particles in a saline solution after the centrifugation.

(2) Production of Carbonate Apatite Nanoparticles (sCA) Using Buffer

To 100 ml of distilled water were added 0.37 g of $NaHCO_3$, 90 µl of $NaH_2PO_4.2H_2O$ (1M), and 180 µl of $CaCl_2$ (1 M) in this order, and dissolved. The pH of the solution was adjusted to 7.5 with 1N HCl. The solution was filtered through a 0.2 µm size filter. Four µl of $CaCl_2$ (1 M) was mixed per 1 ml of the resulting buffer, and the mixture was incubated in a water bath at 37° C. for 30 minutes. Subsequently, the mixture was centrifuged at 15,000 rpm for 5 minutes. The resulting pellet was dispersed in distilled water, a cell culture liquid, or an aqueous solution capable of being administered to cells or a living body, such as a saline solution, so that a dispersion of carbonate apatite particles was obtained. The dispersion was subjected to an ultrasonic vibration treatment for 10 minutes, so that carbonate apatite nanoparticles (hereinafter referred to as "sCA(2) particles") were obtained. A plastic vessel containing the dispersion of carbonate apatite particles was allowed to float in water at 20° C. placed in a water bath having an ultrasonic vibration function, and the ultrasonic vibration treatment was performed under the conditions of a high-frequency power of 55 W and an oscillating frequency of 38 kHz for 10 minutes using the water bath. When the particle size was measured with a microscope, the sCA(2) particles were dispersed in distilled water after the centrifugation. When the dispersion was used for experiments with cells, the dispersion was prepared by dispersing the sCA(2) particles in a DMEM solution without or after the centrifugation. When the dispersion was used for experiments with animals, the dispersion was prepared by dispersing the sCA(2) particles in a saline solution after the centrifugation.

(3) Production of Carbonate Apatite Nanoparticles Containing siRNA (sCA-siRNA)

Similarly to the production (1), 1.35 g of DMEM powder and 0.37 g of $NaHCO_3$ were sequentially added to 100 ml of distilled water, and dissolved completely, and the pH of the solution was adjusted to 7.5 with 1N HCl. The DMEM solution (100 ml) was filtered through a 0.2 µm size filter, and 2 µg of siRNA and 4 µl of $CaCl_2$ (1 M) were mixed per 1 ml of the DMEM solution. The resulting mixture was incubated in a water bath at 37° C. for 30 minutes. When a buffer was used, the preparation was performed as follows. Similarly to the production (2), 0.37 g of $NaHCO_3$, 90 µl of $NaH_2PO_4.2H_2O$ (1M), and 180 µl of $CaCl_2$ (1 M) were added in this order to 100 ml of distilled water, and dissolved, and the pH of the solution was adjusted to 7.5 with 1N HCl. The solution was filtered through a 0.2 µm size filter. Two µg of siRNA and 4 µl of $CaCl_2$ (1 M) were mixed per 1 ml of the resulting buffer, and the mixture was incubated in a water bath at 37° C. for 30 minutes. Subsequently, the mixture was centrifuged at 15,000 rpm for 5 minutes. The resulting pellet was dispersed in distilled water, a cell culture liquid, or an aqueous solution capable of being administered to cells or a living body, such as a saline solution, so that a dispersion of carbonate apatite particles containing siRNA was obtained. The dispersion was subjected to an ultrasonic vibration treatment for 10 minutes, so that carbonate apatite nanoparticles containing siRNA (hereinafter referred to as "sCA-siRNA particles") were obtained. In this case, Alexa Fluor 448-labeled (fluorescently labeled) siRNA (AllStars Neg.siRNA AF488 (manufactured by QIAGEN) was used. A plastic vessel containing the dispersion of carbonate apatite particles containing siRNA was allowed to float in water at 20° C. placed in a water bath having an ultrasonic vibration function, and the ultrasonic vibration treatment was performed under the conditions of a high-frequency power of 55 W and an oscillating frequency of 38 kHz for 10 minutes using the water bath. When the particle size was measured with a microscope, the sCA-siRNA particles were dispersed in distilled water after the centrifugation. When the dispersion was used for experiments with cells, the dispersion was prepared by dispersing the sCA-siRNA particles in a DMEM solution without or after the centrifugation. When the dispersion was used for experiments with animals, the dispersion was prepared by dispersing the sCA-siRNA particles in a saline solution after the centrifugation.

Example 2

Measurement of Particle Size and Morphology

Figures 1, 2:
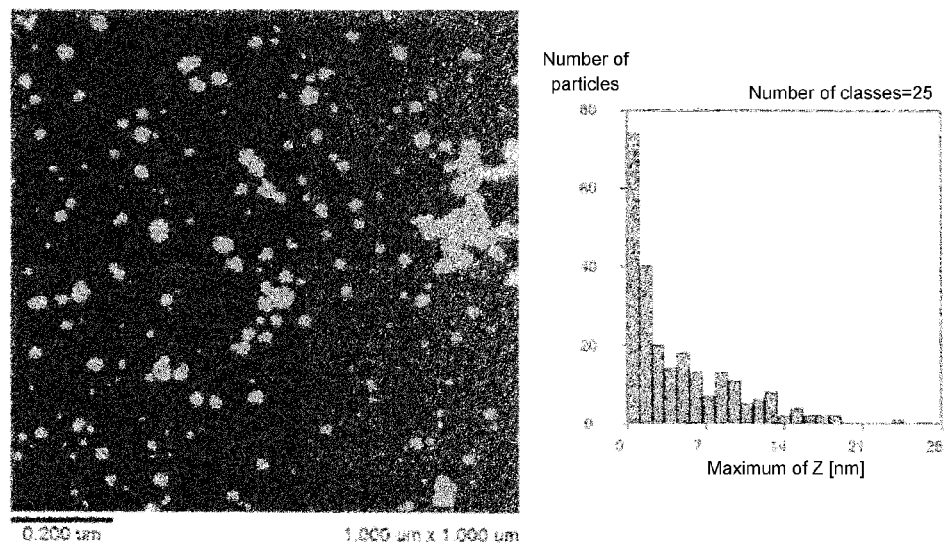
Figures 1, 2, 3:
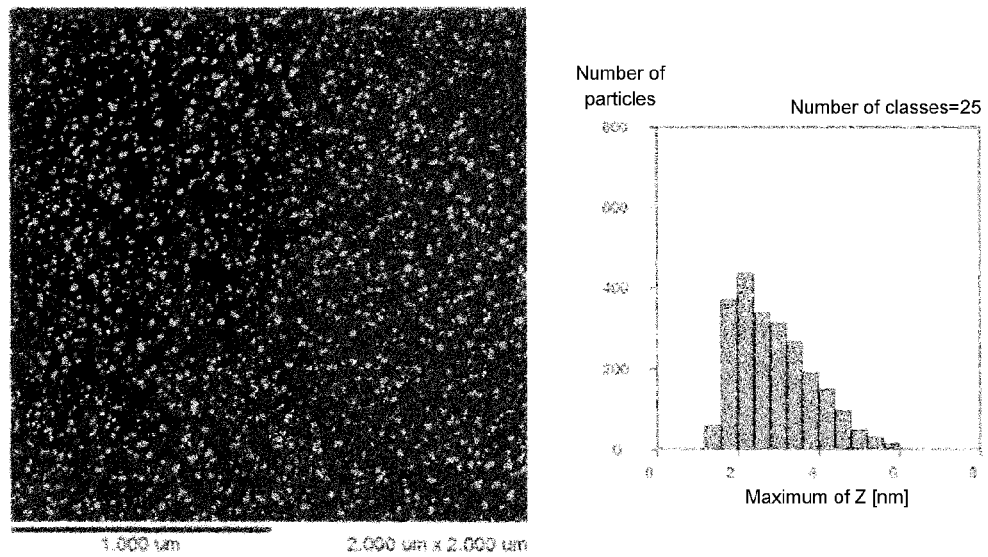
Figure 2:
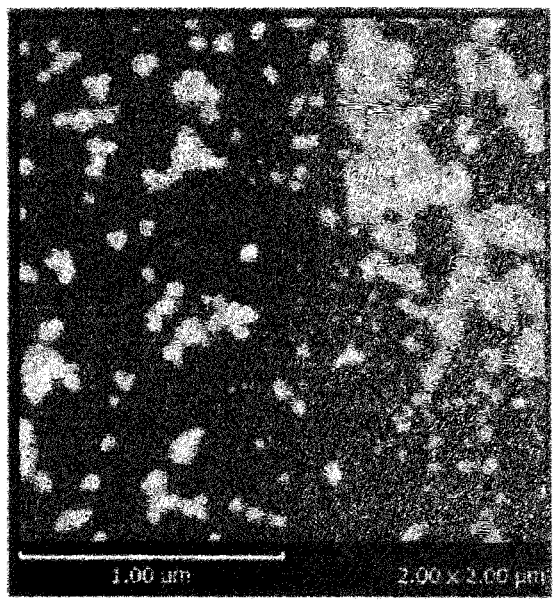
Figures 1, 3:
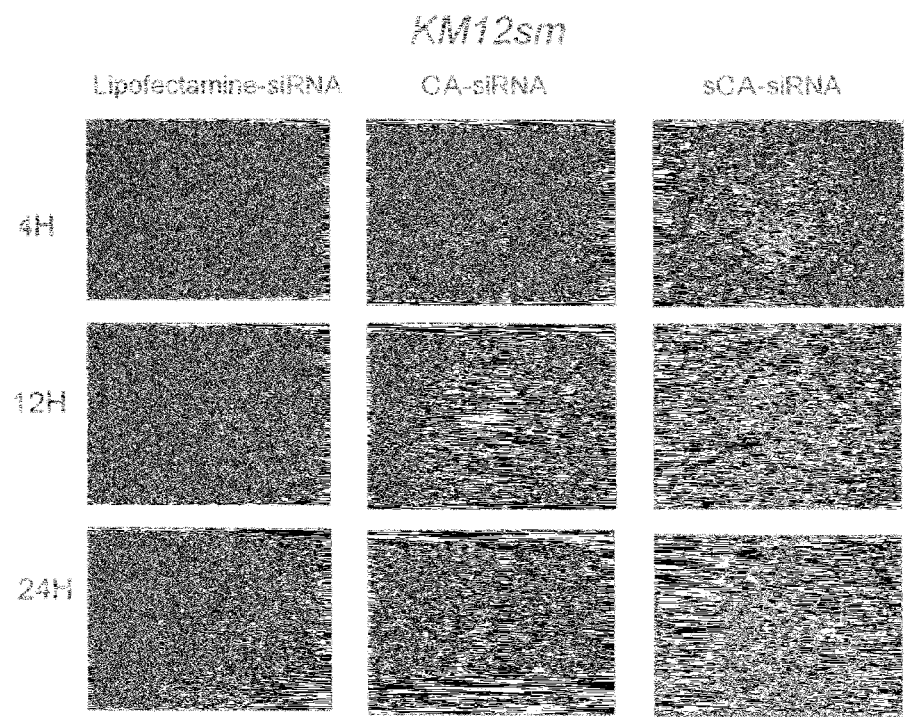
Figures 2, 3:
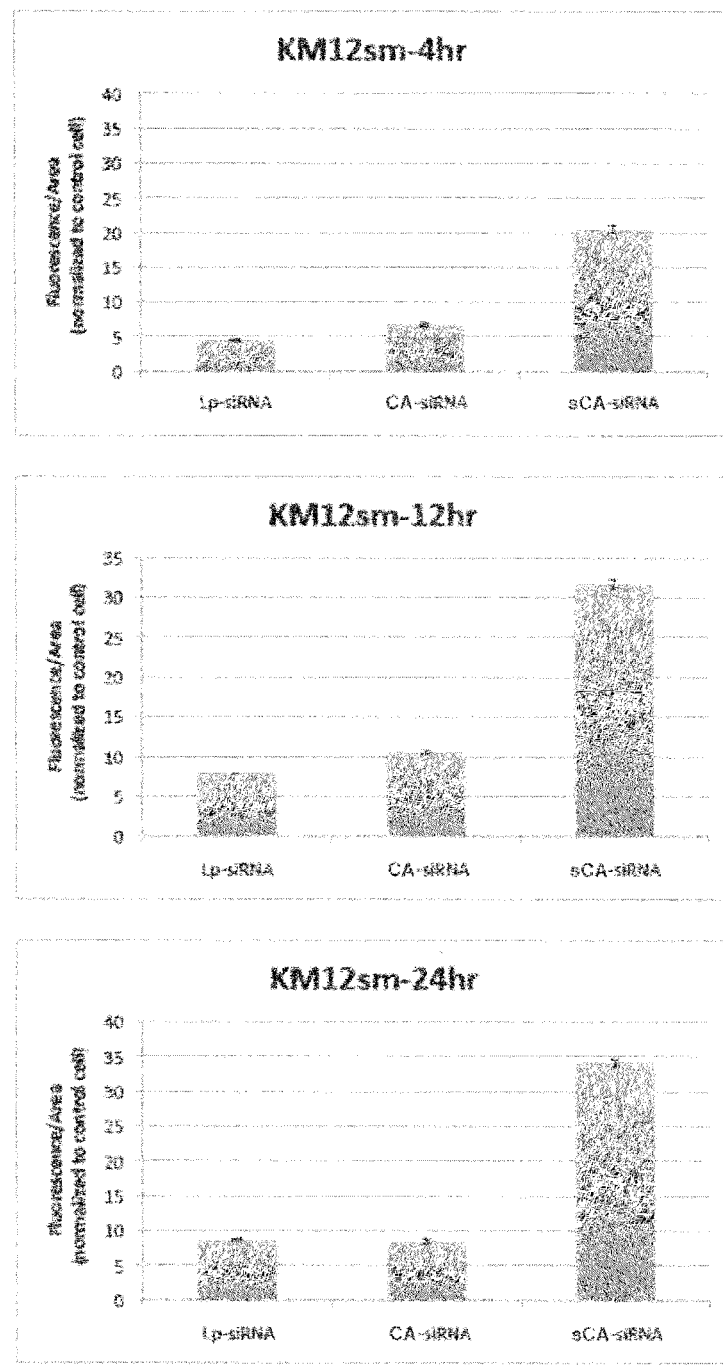

The particle size, morphology, and other properties of the sCA(1) particles, the sCA(2) particles, and the sCA-siRNA particles prepared in Example 1 were measured using, in a dynamic mode, a scanning probe microscope (SPM-9500 manufactured by SHIMADZU CORPORATION) with a microcantilever (OMCL-AC240TS-RS manufactured by Olympus Corporation). The measurement was performed twice within 30 seconds after the ultrasonic vibration treatment in every case. About 10 µl of the aqueous sample solution was dropped on the surface of a cover glass. After the solution was vacuum-dried for 5 minutes, a smooth surface was selected with a CCD camera, and particle size and morphology were measured within an area of 1 to 5 square µm. The results are shown in Table 1 below. FIGS. 1-1 to 1-3 are graphs each showing a two-dimensional analysis image obtained in the measured area and the size distribution of the number of particles. FIG. 1-1 is for the sCA(1) particles, FIG. 1-2 for the sCA(2) particles, and FIG. 1-3 for the sCA-siRNA particles. These results show that the size of carbonate apatite particles can be reduced to 10 nm or less by an ultrasonic vibration treatment. It is also shown that the particle size reduction is also possible when the particles contain siRNA.

siRNA) was prepared according to the product protocol. The sCA-siRNA, CA-siRNA or Lp-siRNA was added to the wells, in which the cancel cell lines were cultured, in such a manner that the siRNA concentration reached 20 pmol/well. The medium was removed 4 hours, 12 hours, and 24 hours after the addition, and the cells were washed with PBS after each removal. Subsequently, concerning uptake of siRNA

TABLE 1

|  | sCA(1) particles | | sCA(2) particles | | sCA-siRNA particles | |
| --- | --- | --- | --- | --- | --- | --- |
|  | Measurement 1 | Measurement 2 | Measurement 1 | Measurement 2 | Measurement 1 | Measurement2 |
| Average particle size (nm) | 2.649 | 3.502 | 4.564 | 3.269 | 2.916 | 2.649 |
| Measured area | 2 μm × 2 μm | | 1 μm × 1 μm | | 2 μm × 2 μm | |
| Number of particles in the measured area | 307 | 235 | 242 | 283 | 2319 | 2964 |

Comparative Example 1

Measurement of the Size and the Morphology of Conventional Type of Carbonate Apatite Particles Carbonate apatite particles were produced as in the production (1) of Example 1, except that the ultrasonic vibration treatment was not performed, and the particle size and the morphology were measured as in Example 2. FIG. 2 shows the resulting two-dimensional analysis image. FIG. 2 shows that the conventional type of carbonate apatite particles prepared without the ultrasonic vibration treatment aggregate together and mostly do not have even a micrometer-scale size. Therefore, since the conventional type of carbonate apatite particles aggregate together, it is not possible to measure the size of individual particles. From the analysis image shown in FIG. 2, however, it is apparent that the individual particles aggregate in the transverse direction and that the width is of the order of several micrometers.

Example 3

Uptake of Carbonate Apatite Nanoparticles into Cells

Five types of human cancer cell lines (HCT116, HT29, KM12SM, 22Rv1, and FaDu) were uniformly seeded on 24-well plates (about $3 \times 10^5$ cells/dish) and cultured overnight. HCT116, HT29, and KM12SM are human colon cancer cell lines, 22Rv1 a human prostate cancer cell line, and FaDu a human head and neck cancer cell line. The HCT116, KM12SM, and FaDu lines were cultured using a 10% fetal bovine serum-supplemented DMEM medium. The HT29 line was cultured using a 10% fetal bovine serum-supplemented RPMI medium. The 22Rv1 line was cultured using a 10% fetal bovine serum-supplemented RPMI medium. The culture was performed under the conditions of 5% CO2 and 37° C.

Using the carbonate apatite nanoparticles, the conventional type of carbonate apatite particles, or Lipofectamine 2000 (manufactured by Invitrogen), control siRNA (manufactured by QIAGEN) fluorescent-labeled with Alexa Fluor 488 was introduced into the cultured cells of each line. The carbonate apatite nanoparticles containing siRNA (sCA-siRNA) were prepared by the procedure (3) of Example 1. The conventional type of carbonate apatite particles containing siRNA (CA-siRNA) were prepared by the procedure (3) of Example 1, except that the ultrasonic vibration treatment was not performed. The Lipofectamine 2000 containing siRNA (Lp-siRNA) was prepared according to the product protocol. The sCA-siRNA, CA-siRNA or Lp-siRNA was added to the wells, in which the cancel cell lines were cultured, in such a manner that the siRNA concentration reached 20 pmol/well. The medium was removed 4 hours, 12 hours, and 24 hours after the addition, and the cells were washed with PBS after each removal. Subsequently, concerning uptake of siRNA into each type of cells, each well was observed with a fluorescence microscope (BZ-9000 manufactured by KEYENCE CORPORATION) and evaluated by flow cytometry.

Figures 1, 4:
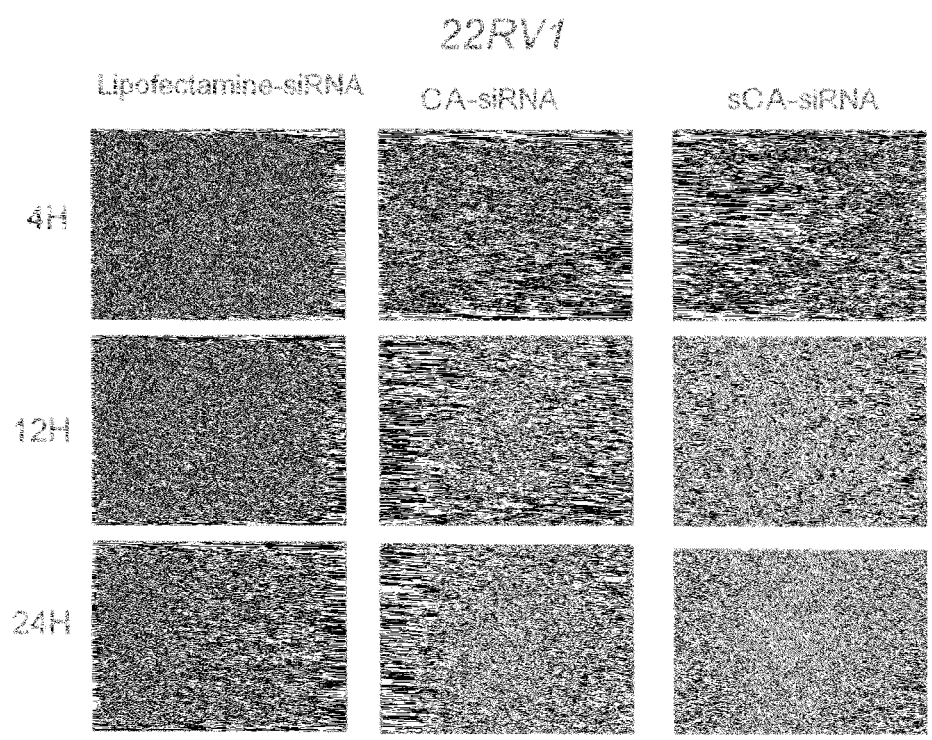
Figures 2, 4:
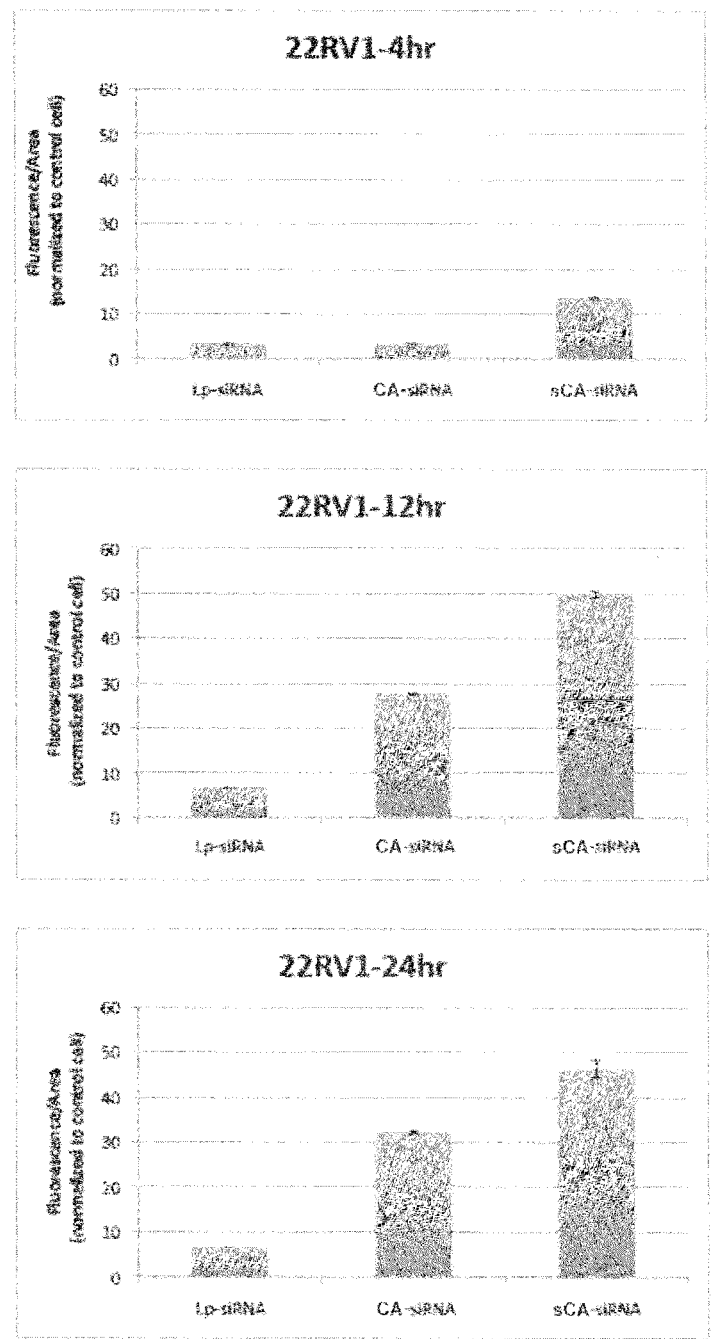
Figures 1, 5:
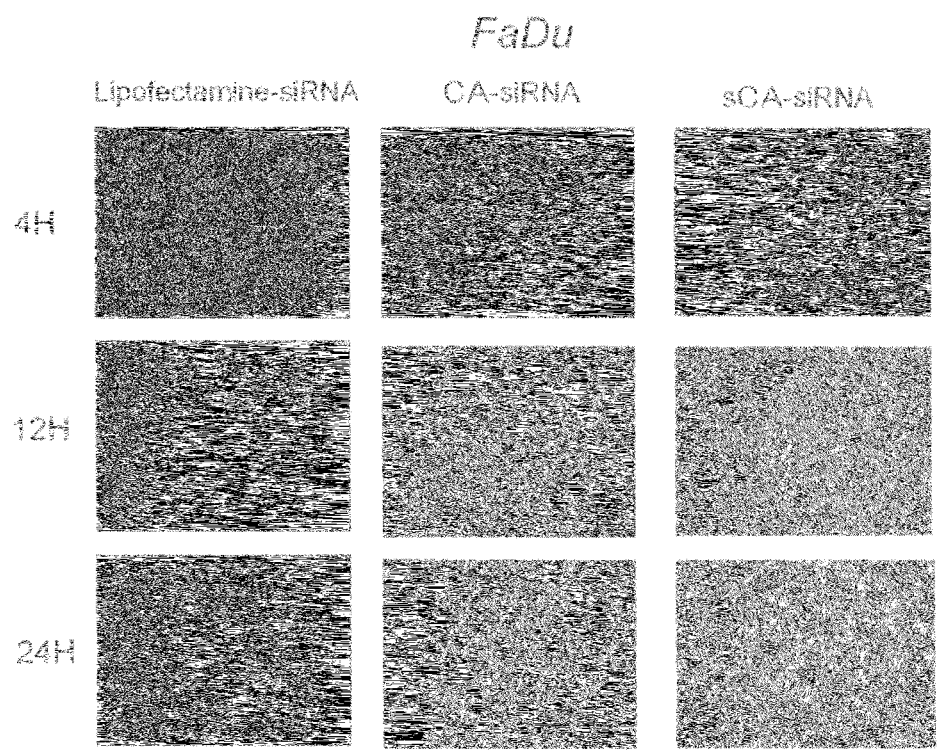
Figures 2, 5:
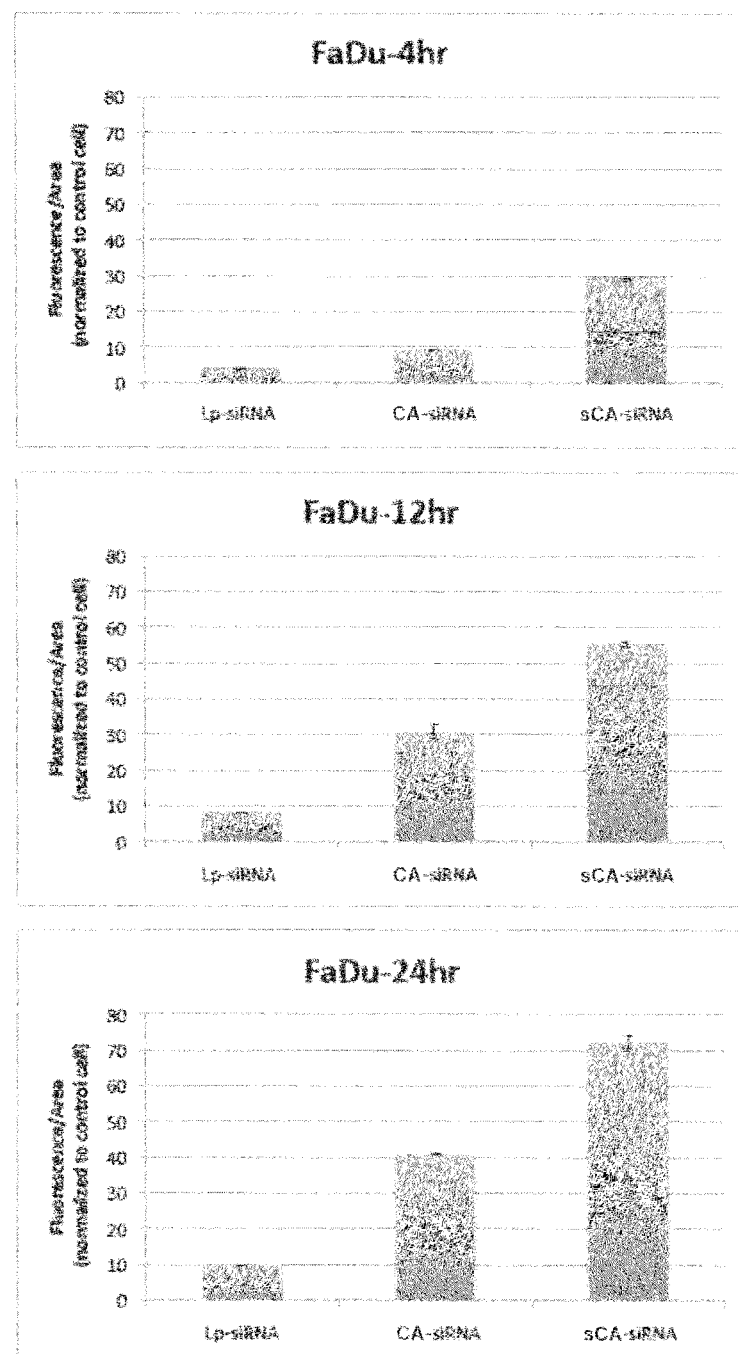
Figure 6:
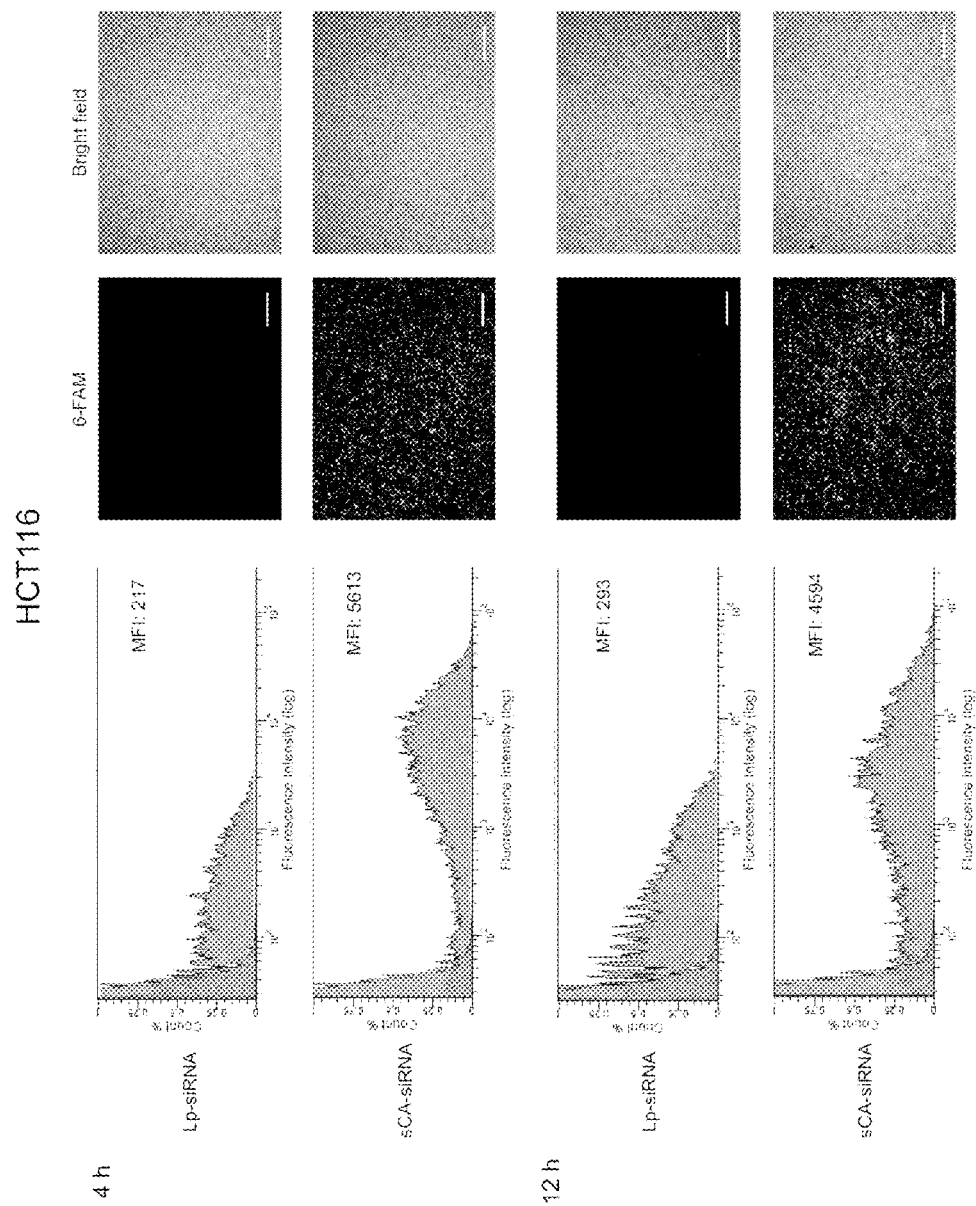
FIG. 6 is a photograph showing the results of the measurement of uptake of siRNA-containing carbonate apatite nanoparticles into HCT116 cells.
Figure 7:
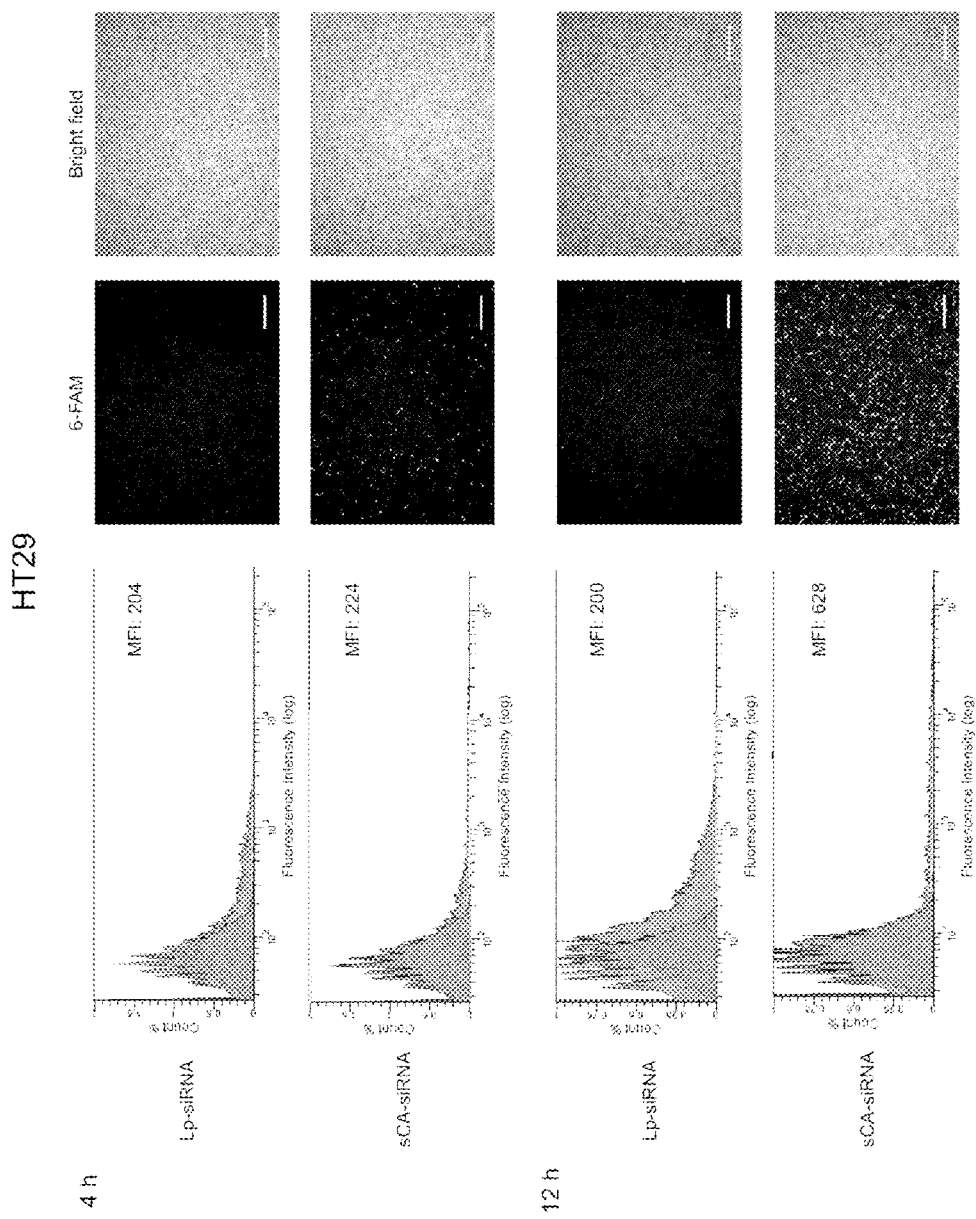
FIG. 7 is a photograph showing the results of the measurement of uptake of siRNA-containing carbonate apatite nanoparticles into HT29 cells.
Figure 8:
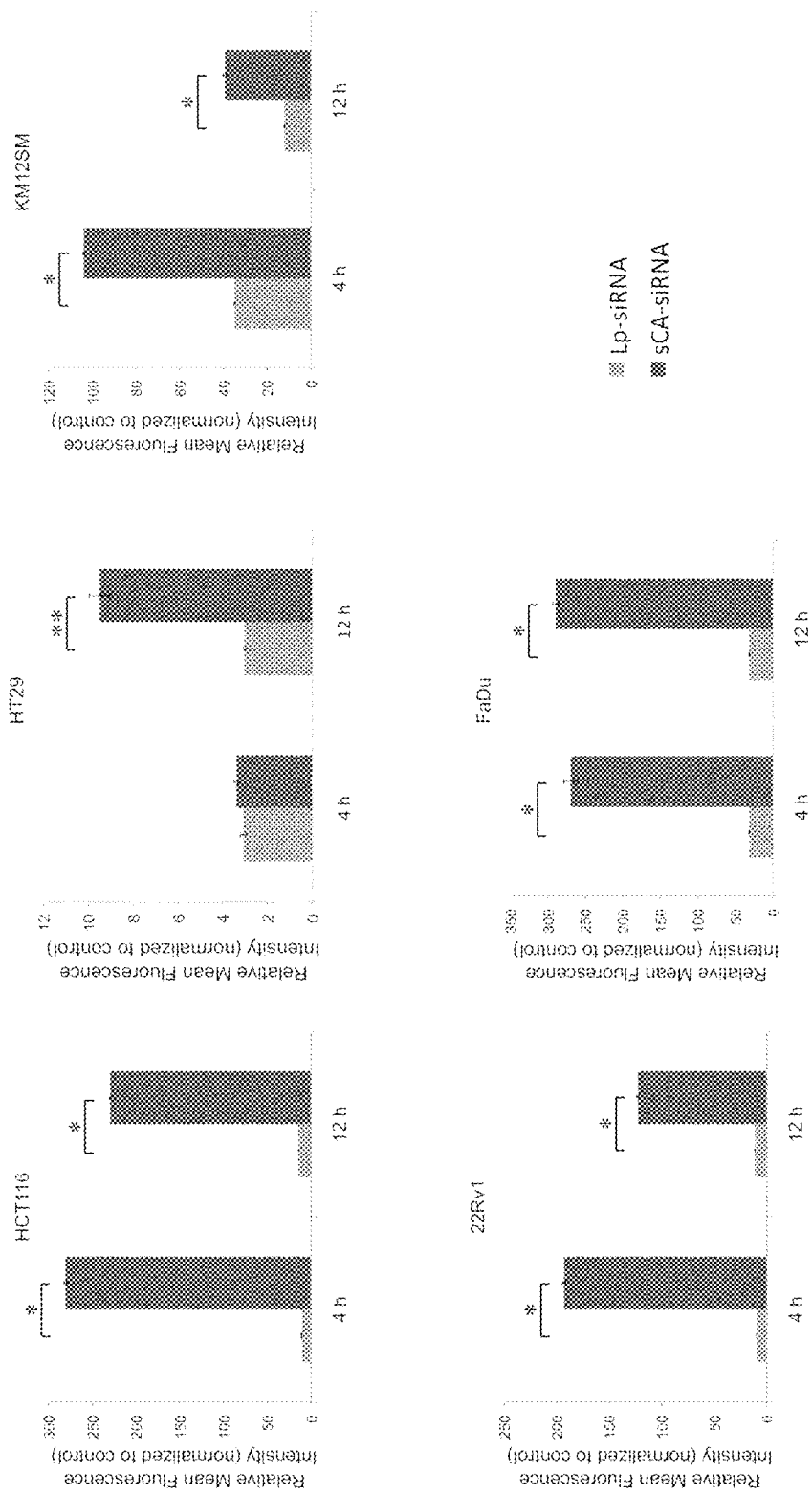
FIG. 8 shows the results of the relative mean fluorescence intensity measurement of uptake of siRNA-containing carbonate apatite nanoparticles into cancer cells of each type.
Figure 9:
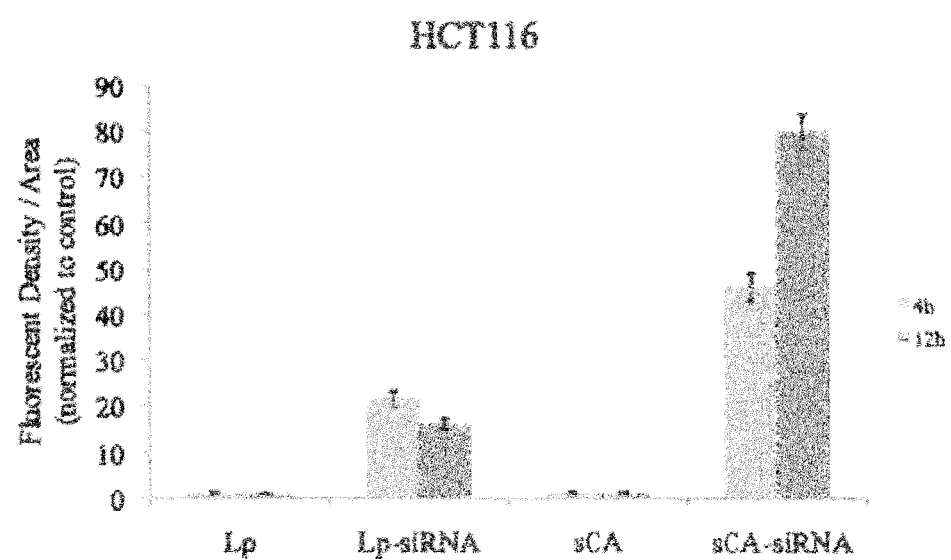
FIG. 9 shows the results of analysis of uptake of siRNA-containing carbonate apatite nanoparticles into HCT116 cells.

FIG. 3-1 shows the KM12SM image observed with the fluorescence microscope, and FIG. 3-2 shows the results of the measurement of the fluorescence area of KM12SM. FIG. 4-1 shows the 22Rv1 image observed with the fluorescence microscope, and FIG. 4-2 shows the results of the measurement of the fluorescence area of 22Rv1. FIG. 5-1 shows the FaDu image observed with the fluorescence microscope, and FIG. 5-2 shows the results of the measurement of the fluorescence area of FaDu. FIG. 6 shows the HCT116 image observed using the fluorescence microscope and the flow cytometry. FIG. 7 shows the HT29 image observed using the fluorescence microscope and the flow cytometry. FIG. 8 shows the results of the measurement of the relative mean fluorescence intensity 4 hours and 12 hours after the addition of sCA-siRNA or Lp-siRNA to cancer cells of each line. FIG. 9 shows the results of the measurement of the fluorescence intensity 4 hours and 12 hours after the addition of sCA-siRNA or Lp-siRNA to HCT116.

These results show that only in the case of using sCA-siRNA, siRNA was clearly taken up into cells of all lines 4 hours after the transfection. It was observed that the amount of the uptake tended to increase with time, but for KM12SM, a substantial increase in the uptake of siRNA was observed only in the case of using sCA-siRNA. For the FaDu cell line, the uptake of siRNA began to be observed 12 hours after the start of the culture also when the conventional type of CA-siRNA and Lp-siRNA were used for the transfection, but the amount of the uptake was considerably smaller than that in the case of using sCA-siRNA. FIG. 9 for HCT116 shows that the fluorescence intensity (namely, the uptake of siRNA) was at least about twice higher in the case of using sCA-siRNA than in the case of using Lp-siRNA. For HCT116, when Lp-siRNA was used, the fluorescence intensity was lower after 12 hours than after 4 hours, and sustained uptake of siRNA was not observed, but when sCA-siRNA was used, the fluorescence intensity was significantly higher after 12 hours than after 4 hours, and sustained uptake was observed. These results demonstrate that the substance can be introduced into cells significantly more efficiently (in a shorter time) and more effectively using sCA-siRNA than using the conventional type of CA-siRNR or Lp-siRNA. When sCA-siRNA was used, similar effects were observed for all the cancer cell lines. This shows that the uptake of sCA-siRNA into cells is less vulnerable to the cancer cell type.

Example 4

Analysis of Uptake into Cells Using Confocal Laser Microscope

HCT116 human colon cancer cells were uniformly seeded on μ-dishes (35 mm high, manufactured by ibidi GmbH) ($1 \times 10^5$ cells/dish) and cultured for 24 hours with a 10% FBS-containing DMEM medium. Subsequently, the medium was replaced by a fresh DMEM medium (2 ml) containing carbonate apatite nanoparticles (sCA-siRNA) containing control siRNA fluorescent-labeled with Alexa Fluor 488, which were used in Example 3, or by a fresh DMEM medium (2 ml) containing Lipofectamine 2000 containing control siRNA fluorescent-labeled with Alexa Fluor 488 (Lp-siRNA), which was used in Example 3. The fresh medium contained siRNA at a concentration of 100 pmol/well. The culture was then continued. Carbonate apatite nanoparticles (CA) and Lipofectamine 2000 (Lp) each not containing siRNA were used as negative controls. Zero hours, 4 hours, and 12 hours after the medium replacement, the medium was removed, and the cells were washed twice with PBS and then fixed for 30 minutes using 4% PFA. A drop of a DAPI-supplemented ProLong Gold antifade reagent (manufactured by Invitrogen) was then added to each culture dish, which was followed by incubation at 4° C. for 24 hours. Subsequently, analysis was performed using a confocal laser scanning microscope (FV1000-D manufactured by Olympus Corporation).

Figures 1, 10:
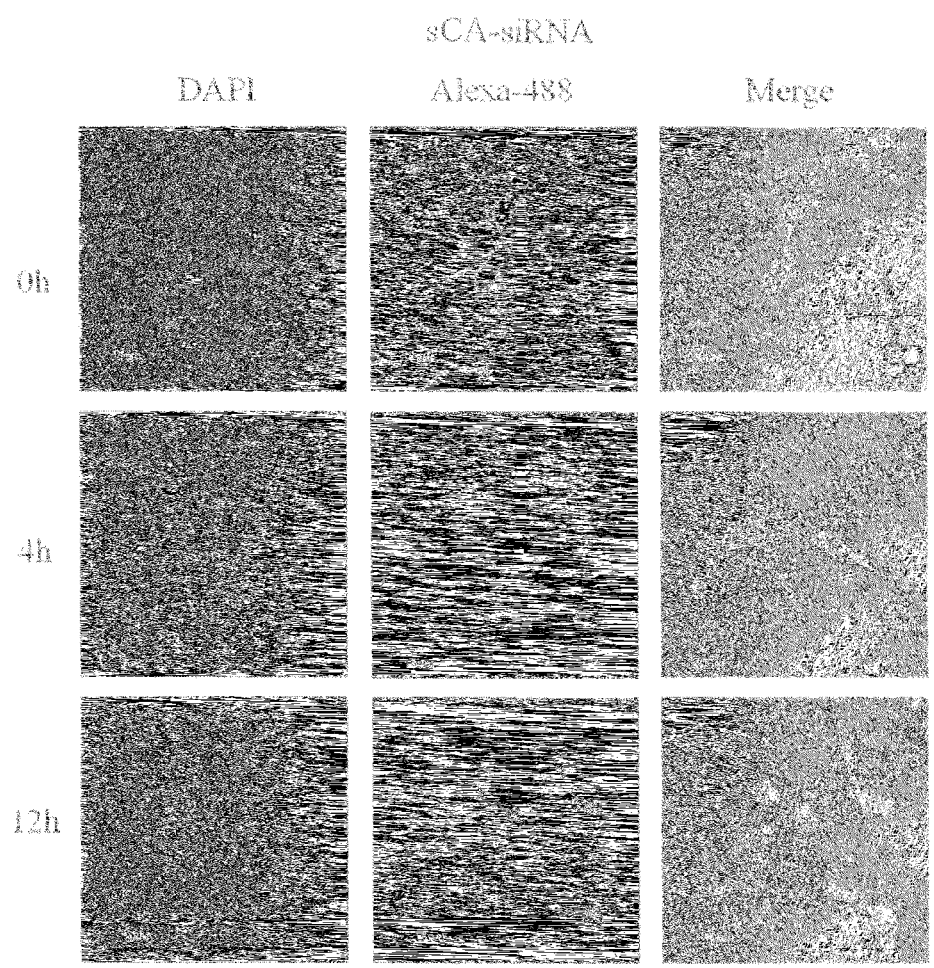
Figures 2, 10:
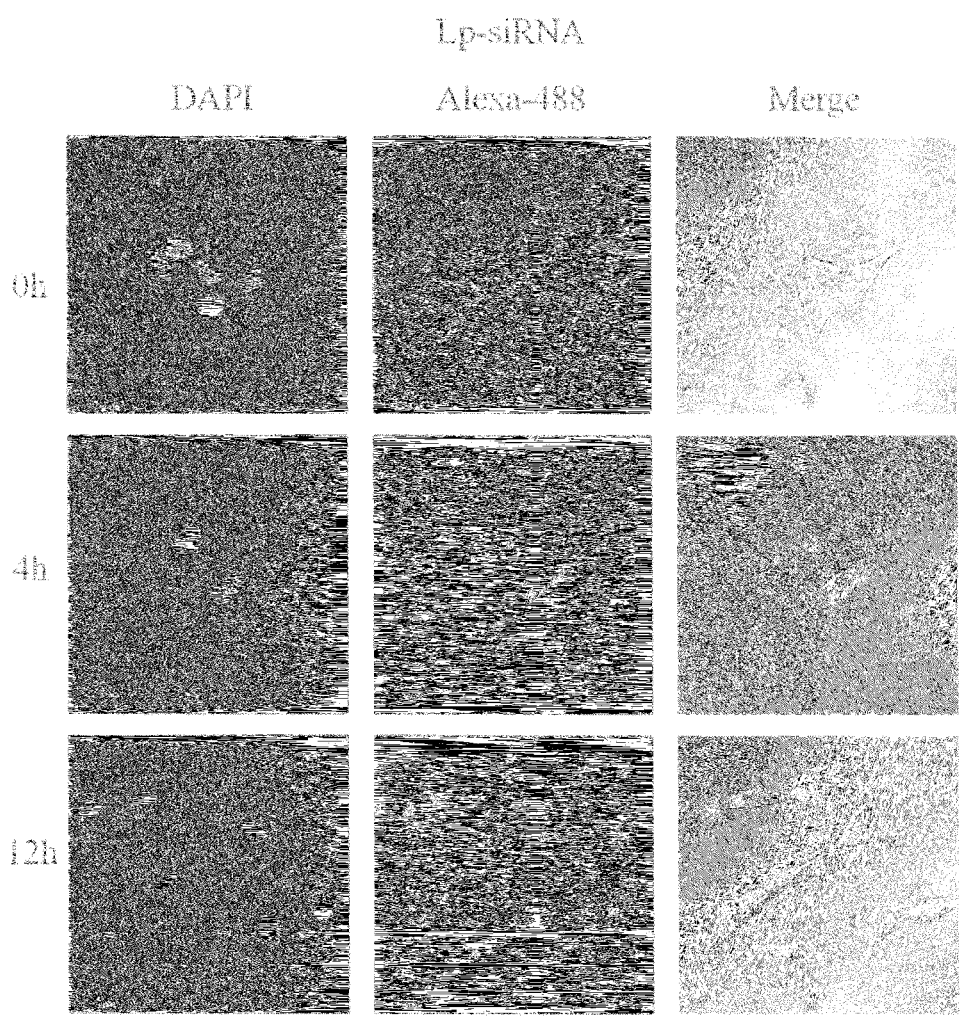

Photographs obtained by high-resolution analysis are shown in FIGS. 10-1 and 10-2. FIG. 10-1 shows the results obtained with sCA-siRNA, and FIG. 10-2 shows the results obtained with Lp-siRNA. In FIGS. 10-1 and 10-2, the position of cellular nuclei stained with DAPI is indicated on the left side, the position of sCA-siRNA or Lp-siRNA is indicated at the center, and the photographs in which these positions are combined are shown on the right. A comparison between the 0-hour images shows that when sCA-siRNA was used, sCA-siRNA was already bound to the cellular surface at this time, but when Lp-siRNA was used, such an event was not observed. This shows that carbonate apatite nanoparticles have a higher affinity for cells and can more rapidly adhere to the cellular surface than Lipofectamine, which suggests that as a result, substances can be introduced into cells in a shorter time using carbonate apatite nanoparticles. Next, a comparison between the results after 4 hours and 12 hours shows that when sCA-siRNA was used, the Alexa Fluor 488 fluorescence was observed in the cytoplasm after 4 hours, and after 12 hours, the fluorescence spread over the entire cytoplasm and reached even the nucleus. On the other hand, when Lp-siRNA was used, the fluorescence signal was localized at part of the cytoplasm even after 12 hours. This difference seems to be caused by the fact that sCA-siRNA is nanometer-scale particles and has the property of releasing the contained substance depending on pH. Specifically, sCA-siRNA is charged to adhere to the cellular surface. The sCA-siRNA adhering to the cellular surface is then taken up into cells at an accelerated rate by endocytosis because of the nanometer-scale size. Subsequently, as the pH in the endosome decreases, the substance is promptly released from sCA-siRNA and also allowed to escape from the endosome. In contrast, Lipofectamine does not have these mechanisms. The release from the endosome is advantageous in that siRNA is prevented from being decomposed by a lysosome.

Example 5

In Vivo Distribution 1 of Carbonate Apatite Nanoparticles

HCT116 or HT29 human colon cancer cells were subcutaneously injected into the left and right backs of 7 week-old BALB/cA nude mice (produced by CLEA Japan, Inc.), so that solid tumor-bearing model mice were produced. At the time when the tumor size reached 10 mm, the mice were randomly divided into three groups: a control group, a naked-siRNA administration group, and an sCA-siRNA administration group. The naked-siRNA administration group was administered by tail vein injection with a saline solution containing 40 μg of fluorescent 6-FAM-labeled control siRNA (manufactured by KOKEN CO., LTD.). Carbonate apatite nanoparticles containing 6-FAM-labeled control siRNA (sCA-siRNA) were prepared by the same procedure as in the production (3) of Example 1, and administered to the sCA-siRNA group by tail vein injection in such a manner that the dose of siRNA was the same as that to the naked-siRNA administration group. The dose was controlled according to the technique described in J. Control Release, 147, 101-108 (2010). It will be understood that the conventional type of carbonate apatite particles, which can aggregate to form very large clusters as shown in Comparative Example 1, cannot be administered in this way because they can clog blood vessels if administered into veins.

Figure 11:
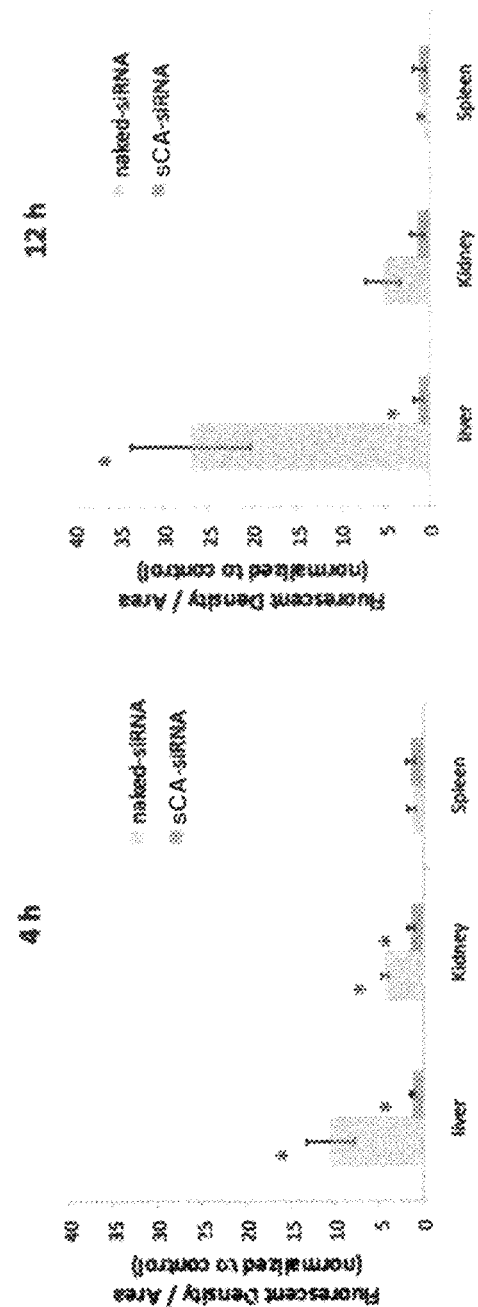
FIG. 11 shows the results of analysis of accumulation in the liver, kidney, and spleen of tumor-bearing model mice intravenously injected with siRNA-containing carbonate apatite nanoparticles.
Figures 1, 12:
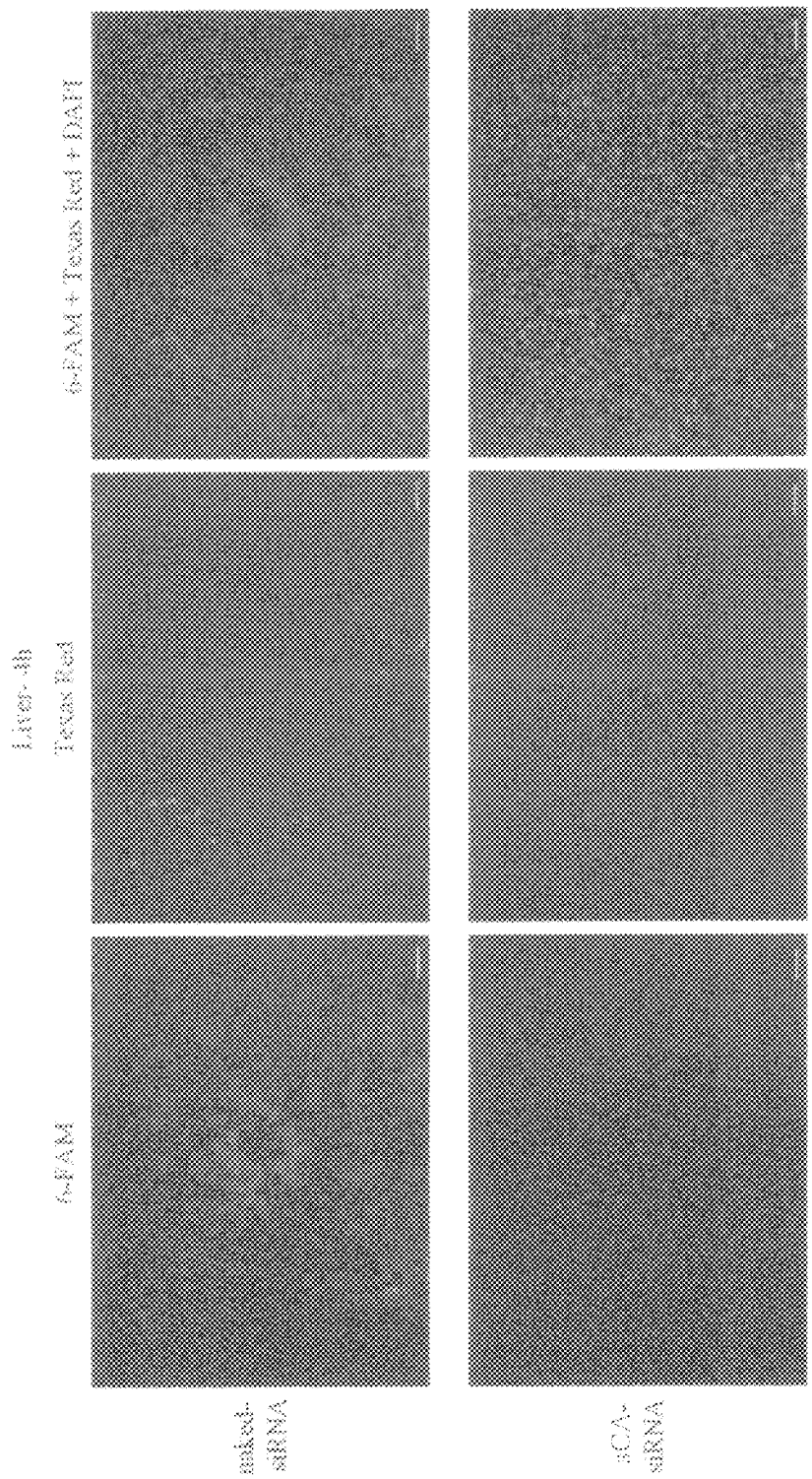
Figures 2, 12:
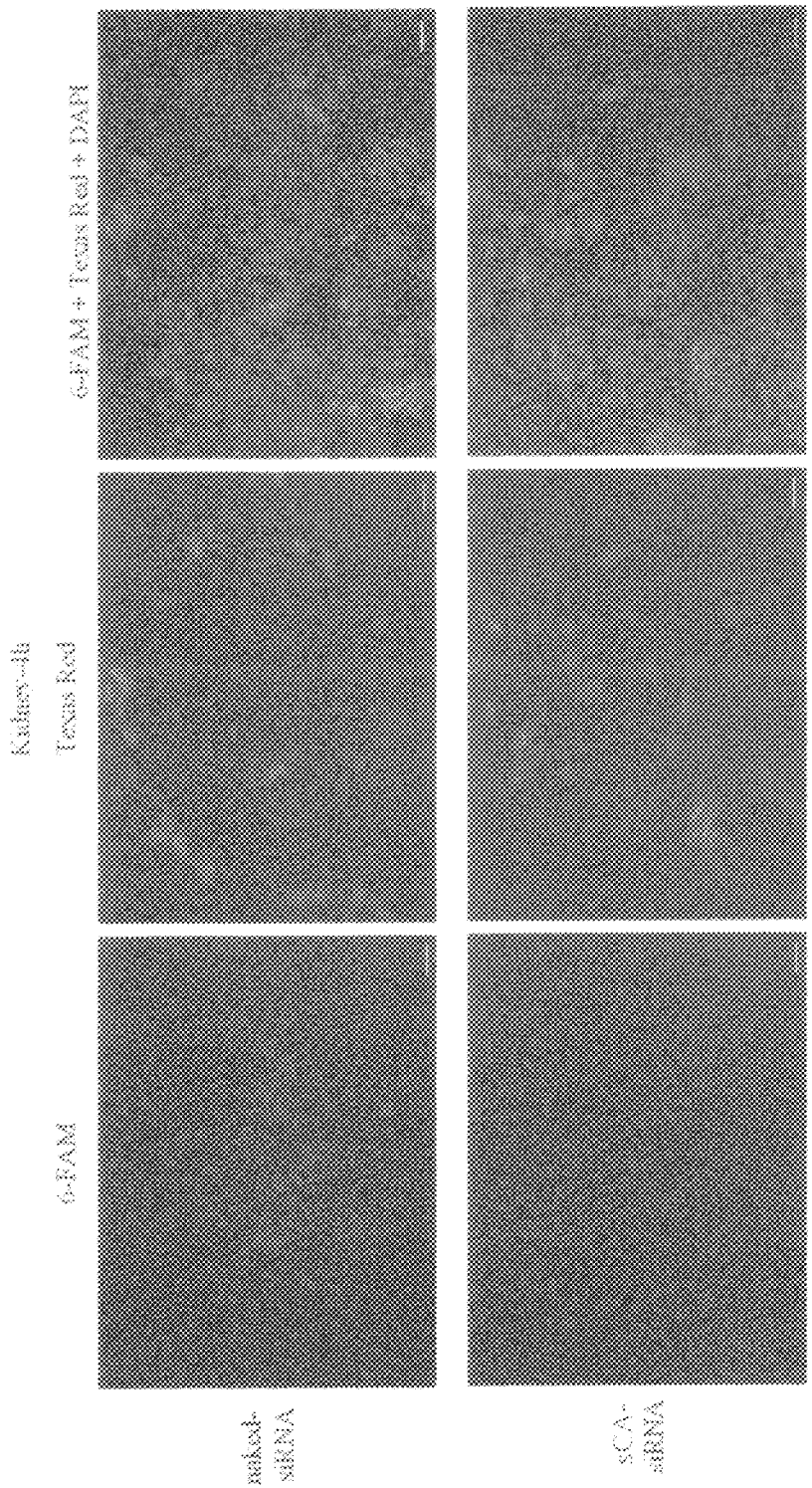
Figures 1, 13:
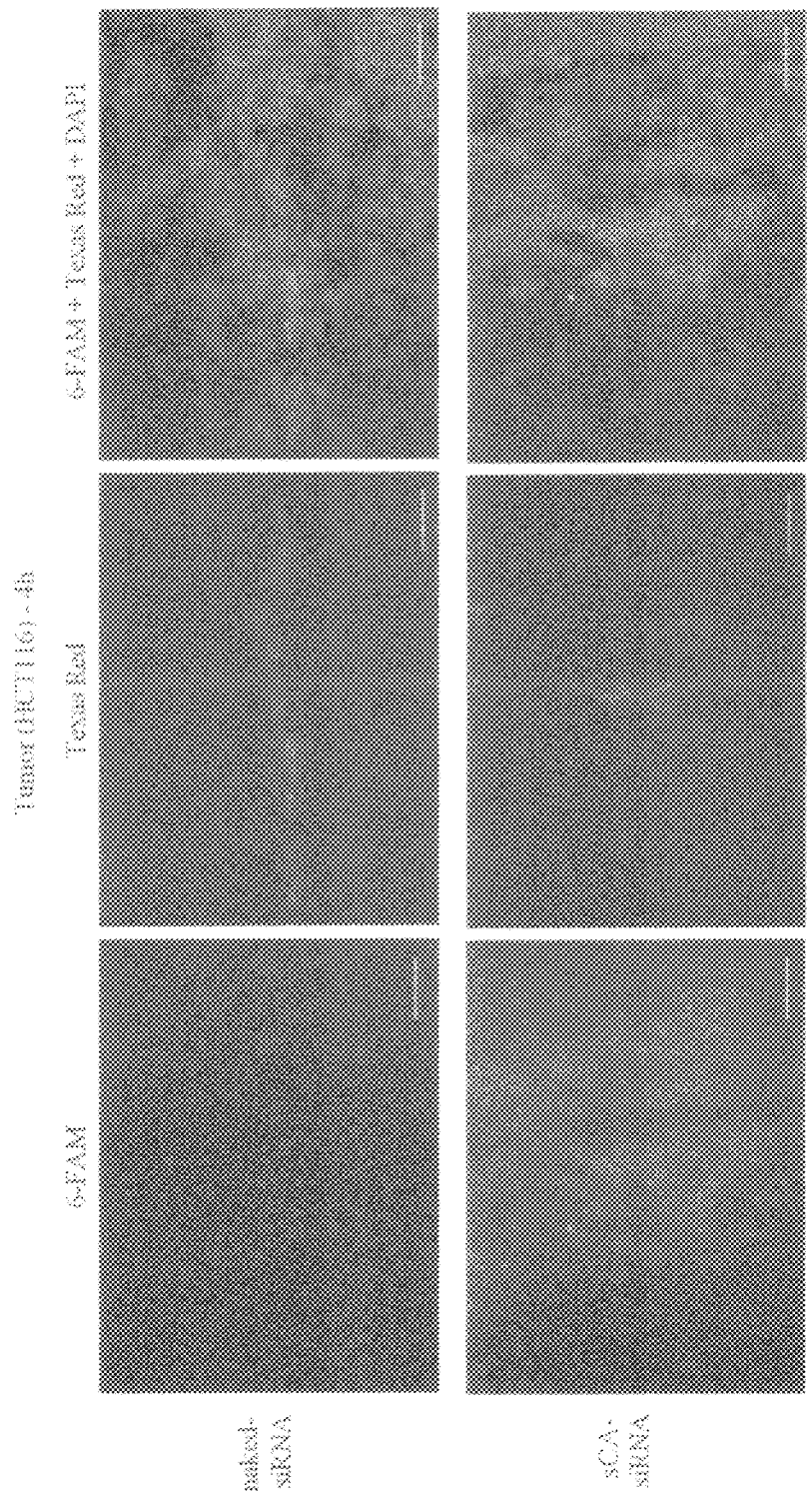
Figures 2, 13:
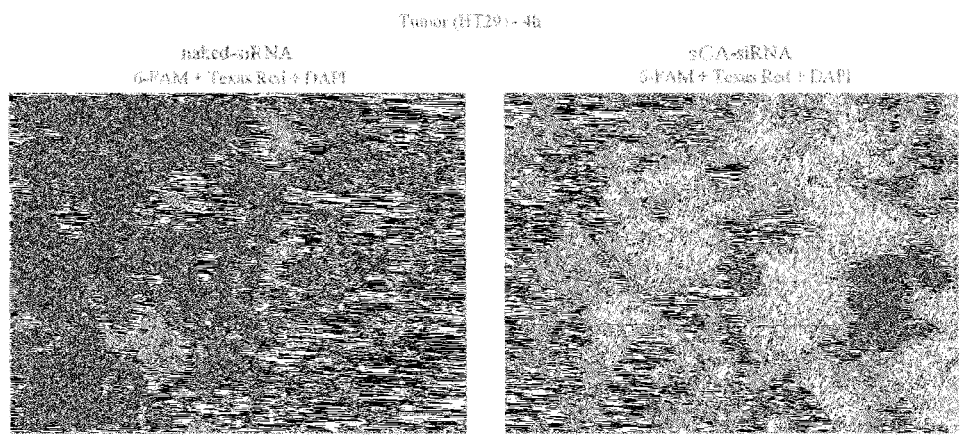
Figures 3, 13:
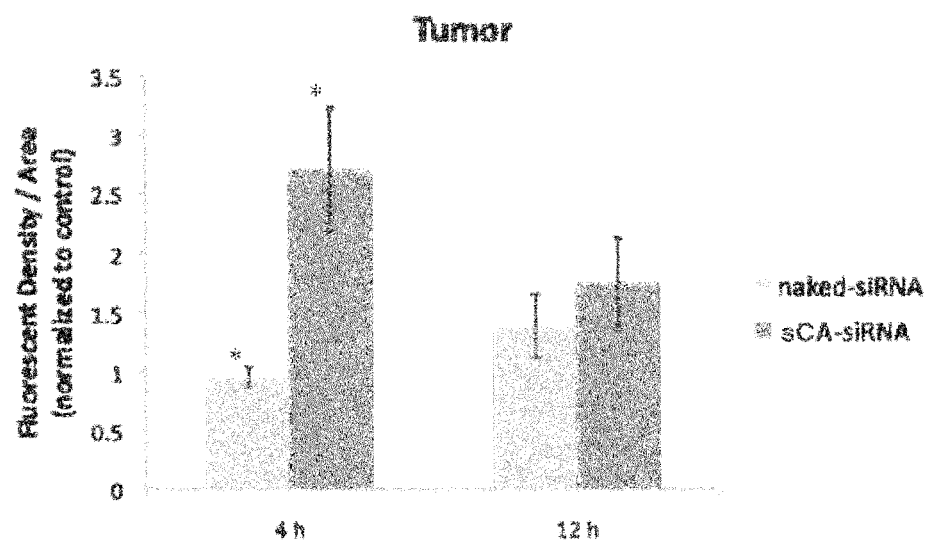

To stain blood vessels, Texas red-labeled dextran was intravenously administered 30 minutes before abdominal section. Four hours or 12 hours after the administration of siRNA, the liver, kidney, spleen, and tumor were taken out under anesthesia, embedded in O.C.T. compound, and stored at −80° C. From the frozen samples, 20 μm thick sections were prepared, fixed for 30 minutes using 4% PFA, and washed three times with PBS-T for 5 minutes. Subsequently, a DAPI-containing ProLong Gold antifade reagent was mounted, which was followed by incubation at 4° C. for 24 hours. The fluorescent-labeled siRNA in the samples was evaluated using a fluorescence microscope (BX-9000 manufactured by KEYENCE CORPORATION). Two-photon imaging was performed to visualize the leaching of sCA-siRNA or naked-siRNA from blood vessels. The imaging was performed using a system including a multi-photon microscope (SP5 manufactured by Leica) driven by a laser adjusted to 900 nm (Mai-Tai HP Ti (sapphire) manufactured by Spectra-Physics K.K.) and an upright microscope (DM6000B manufactured by Leica) with a 20× water-immersion objective. The results of the analysis are shown in FIGS. 11 to 13. FIG. 12-1 is an image of the liver after 4 hours, and FIG. 12-2 is an image of the kidney after 4 hours. FIG. 13-1 is an image of the HCT116-derived tumor tissue. FIG. 13-2 is an image of the HT29-derived tumor tissue. FIG. 13-3 shows the 6-FAM-derived fluorescence intensity detected in the HCT116-derived tumor tissue.

From the results shown in FIGS. 11 and 12, it is apparent that both 4 hours and 12 hours after the administration, naked-siRNA was accumulated in the liver and the kidney, whereas sCA-siRNA was not substantially accumulated in any of the liver and the kidney. The amounts of siRNA accumulated in the liver after 4 hours and 12 hours in the case of using sCA-siRNA were 1/10 and 1/26 of those in the case of using naked-siRNA, respectively. The amounts of siRNA accumulated in the kidney after 4 hours and 12 hours in the case of using sCA-siRNA were 1/4 and 1/5 of those in the case of using naked-siRNA, respectively. The fluorescence intensity shown in FIG. 11 is the ratio to the intensity of the control. FIG. 11 shows that the fluorescence ratio in the normal organ is about 1 when sCA-siRNA was used. This means the same fluorescence intensity as that of the control where there was nothing particular, which suggests that almost no carbonate apatite nanoparticles would be accumulated in normal tissues. These results indicate that sCA-siRNA is less likely to be captured by the endothelium system of liver or spleen, has low hepatotoxicity, and is also less likely to be removed by kidney.

FIG. 13-1 shows that when naked-siRNA was administered, a signal (green) indicating the presence of siRNA in blood vessels was detected to a certain extent, but such a signal was not clearly detected in the tumor cell area. This suggests that when naked-siRNA is intravenously administered, sufficient leaching of siRNA from blood vessels to tumor cells cannot be obtained in tumor tissues. In contrast, when sCA-siRNA was administered, a clear signal indicating the presence of siRNA was detected not only in blood tissues but also in a wide range of tumor tissues. Similar results were more clearly observed in the HT29-derived tumor tissue (FIG. 13-2). These results indicate that siRNA contained in sCA-siRNA is more stable in in-vivo environment than naked-siRNA and can leach from blood vessel walls and reach tumor tissues far from blood vessels. This is also supported by the fact that the fluorescence intensity detected in the tumor tissue when sCA-siRNA was used was significantly higher than that when naked-siRNA was used (FIG. 13-3). In FIG. 13-3, the fluorescence intensity detected after 12 hours is lower than that detected after 4 hours in the case of using sCA-siRNA. This may reflect that the carbonate apatite nanoparticles have the property of quickly releasing the contained material in low-pH environments such as tumor tissues.

Example 6

In Vivo Distribution 2 of Carbonate Apatite Nanoparticles

The following test was performed to compare the in vivo distribution of carbonate apatite nanoparticles with that of known drug delivery carriers.

Using the same technique as in Example 5, HCT116 or HT29 human colon cancer cells or FaDu human head and neck cancer cells were subcutaneously injected into mice, so that solid tumor-bearing model mice were produced. At the time when the tumor size reached 10 mm, the mice were randomly divided into three groups: an IF-siRNA administration group, an Atelo-siRNA administration group, and an sCA-siRNA administration group. The IF-siRNA administration group was administered by tail vein injection with Invivofectamine 2.0 (manufactured by Invitrogen) containing fluorescent-labeled control siRNA (manufactured by KOKEN CO., LTD.) (IF-siRNA) in such a manner that 40 µg of the fluorescent-labeled siRNA was administered to each mouse. The Atelo-siRNA administration group was administered by tail vein injection with AteloGene (manufactured by KOKEN CO., LTD.) containing fluorescent-labeled control siRNA (manufactured by KOKEN CO., LTD.) (Atelo-siRNA) in such a manner that 40 µg of the fluorescent-labeled siRNA was administered to each mouse. The sCA-siRNA administration group was administered by tail vein injection with carbonate apatite nanoparticles containing fluorescent-labeled control siRNA (manufactured by KOKEN CO., LTD.) (sCA-siRNA) in such a manner that 40 µg of the fluorescent-labeled siRNA was administered to each mouse (the binding affinity of siRNA to sCA nanoparticles is 40.6±2.9% (n=4)). IF-siRNA and Atelo-siRNA were each prepared according to the product protocol. The sCA-siRNA was prepared by the same procedure as in the production (3) of Example 1.

Twelve hours after the administration of IF-siRNA, Atelo-siRNA, or sCA-siRNA, the mice were subjected, under anesthesia, to computer tomography (CT) analysis using IVIS spectrum CT system (PerkinElmer), in which three-dimensional in vivo images were obtained. Using the same method as in Example 6, siRNA contained in the liver, kidney, and spleen was measured with a fluorescence microscope. In the experiment where three-dimensional in vivo images of mice were obtained, Alexa Fluor 750-labeled siRNA was used as the fluorescent-labeled siRNA. In the measurement of siRNA contained in the liver, kidney, spleen, and tumor, 6-FAM-labeled siRNA was used as the fluorescent-labeled siRNA.

Results of Evaluation of Uptake into Liver, Kidney, and Spleen

Figure 14:
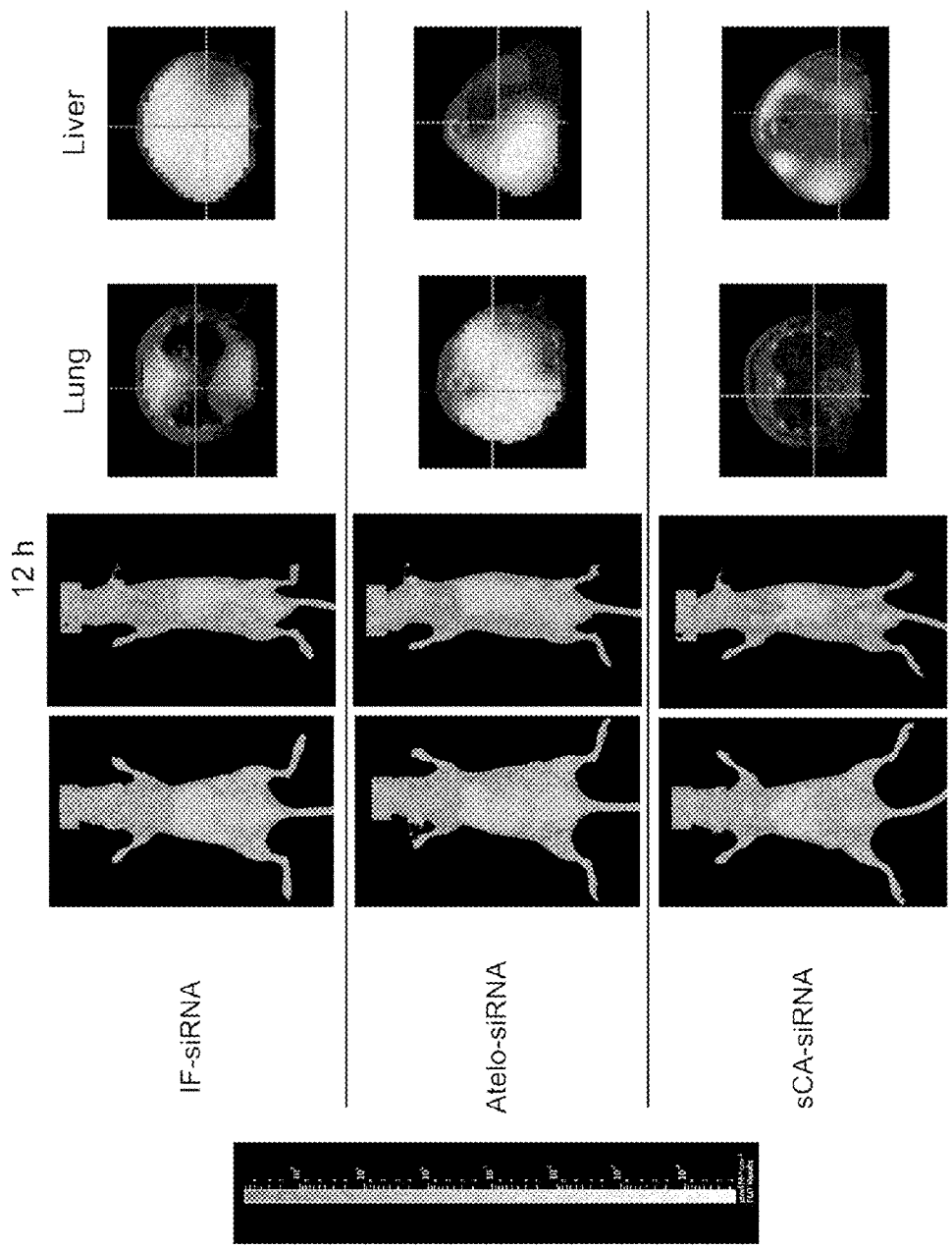
FIG. 14 is a three-dimensional in vivo image showing a distribution of siRNA-containing carbonate apatite nanoparticles in a tumor-bearing model mouse intravenously injected with siRNA-containing carbonate apatite nanoparticles.

FIG. 14 shows the results of taking three-dimensional in vivo images of mice. In the IF-siRNA administration group, the fluorescence of Alexa Fluor 750 was not significantly observed in the lung 12 hours after the administration, but the fluorescence of Alexa Fluor 750 was accumulated in the liver. In the Atelo-siRNA administration group, the fluorescence of Alexa Fluor 750 was strongly observed in the liver and the lung. In the sCA-siRNA administration group, however, the fluorescence of Alexa Fluor 750 was not observed in the lung although the fluorescence of Alexa Fluor 750 was observed in part of the liver.

Figures 1, 15:
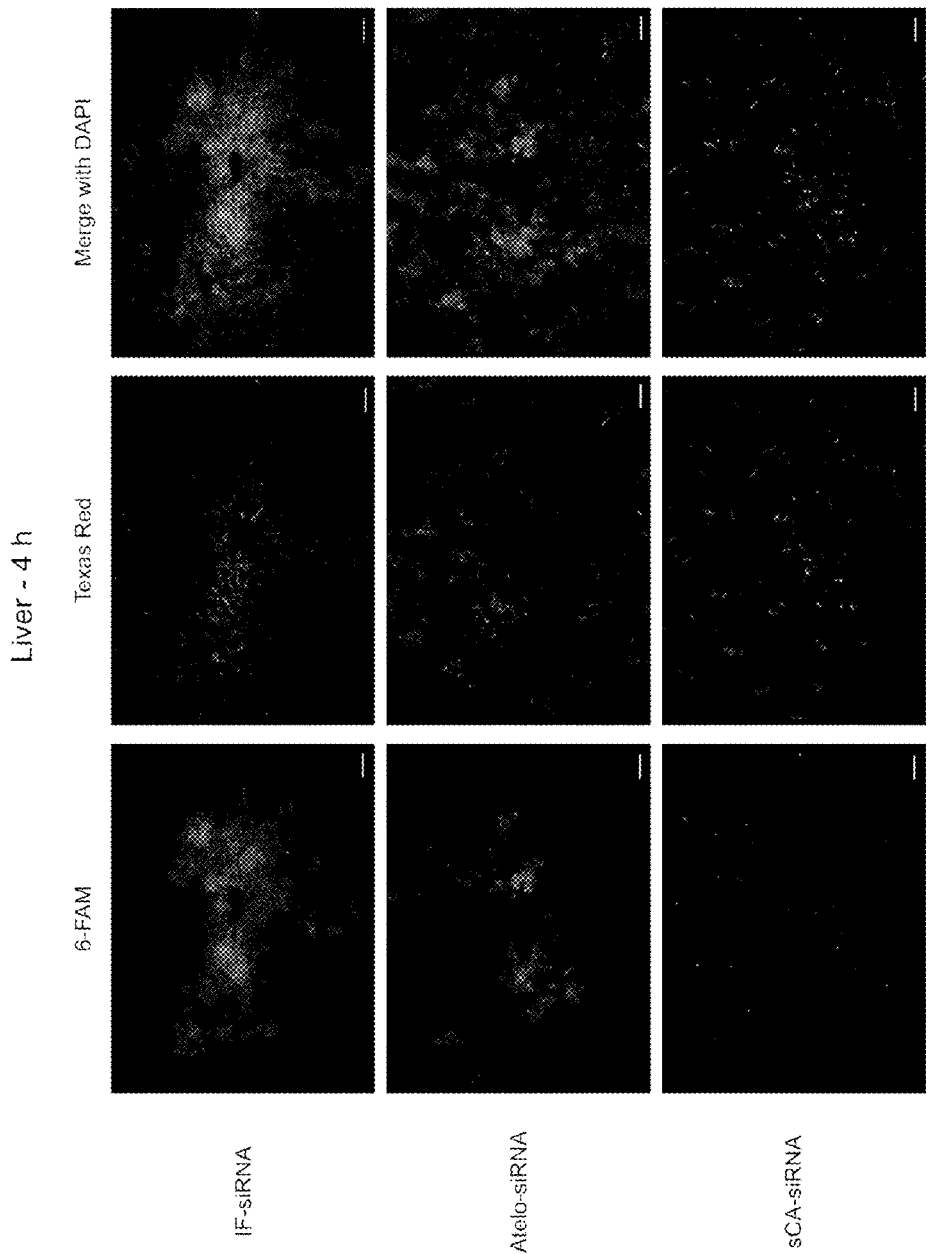
Figures 2, 15:
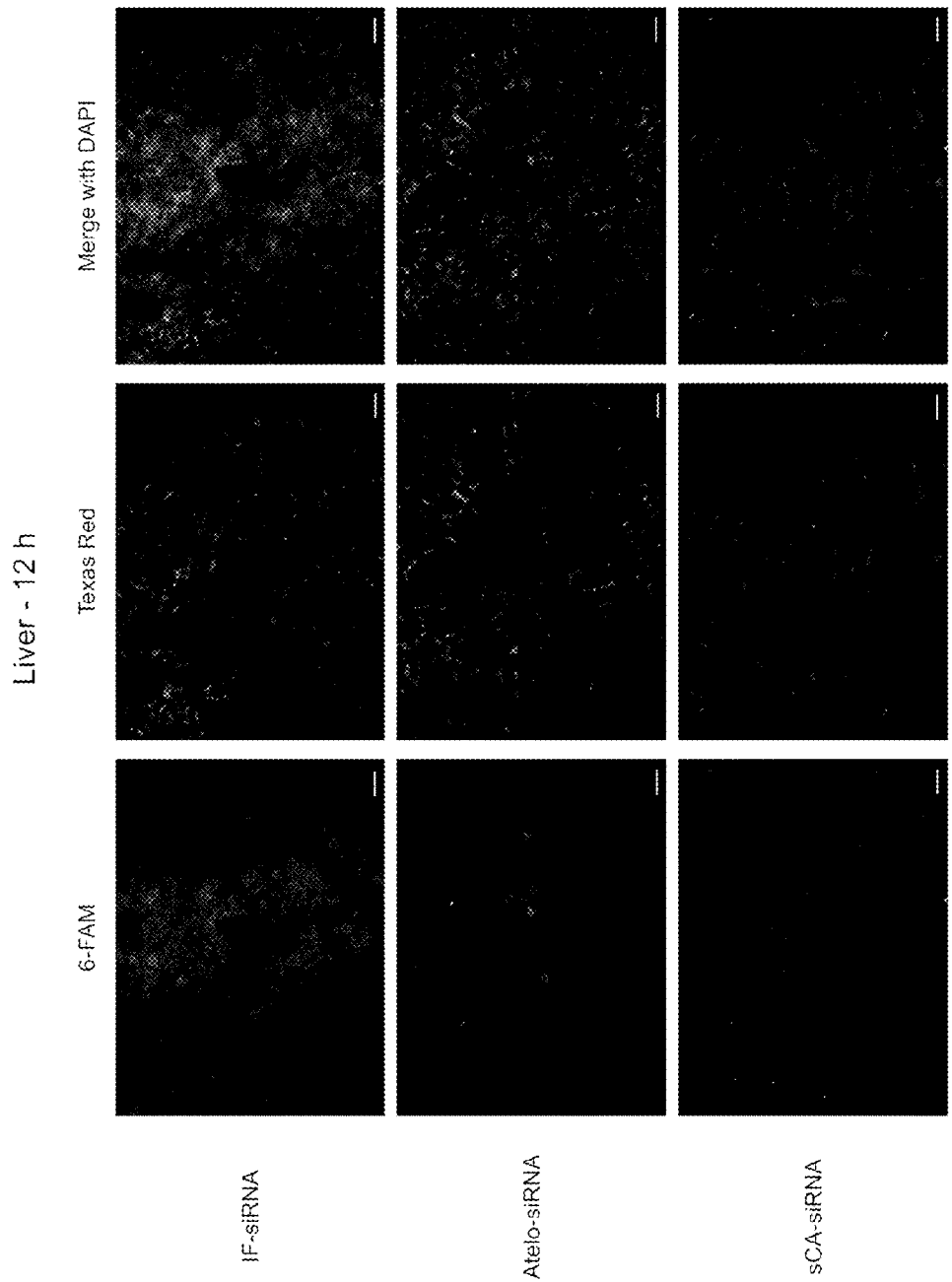
Figures 3, 15:
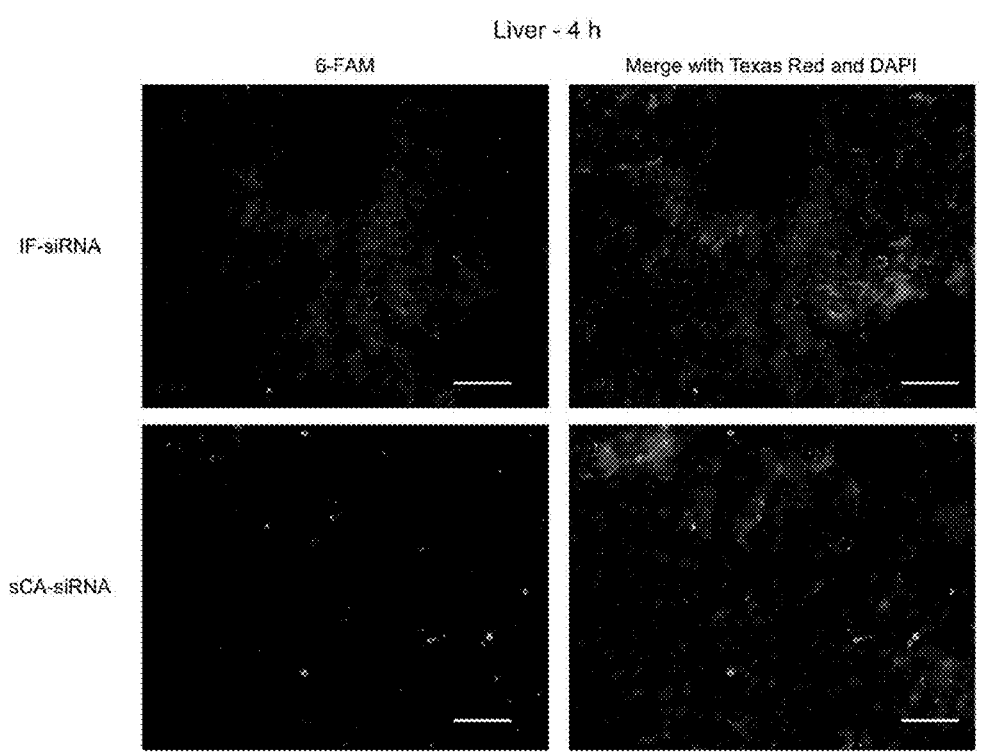
Figures 1, 16:
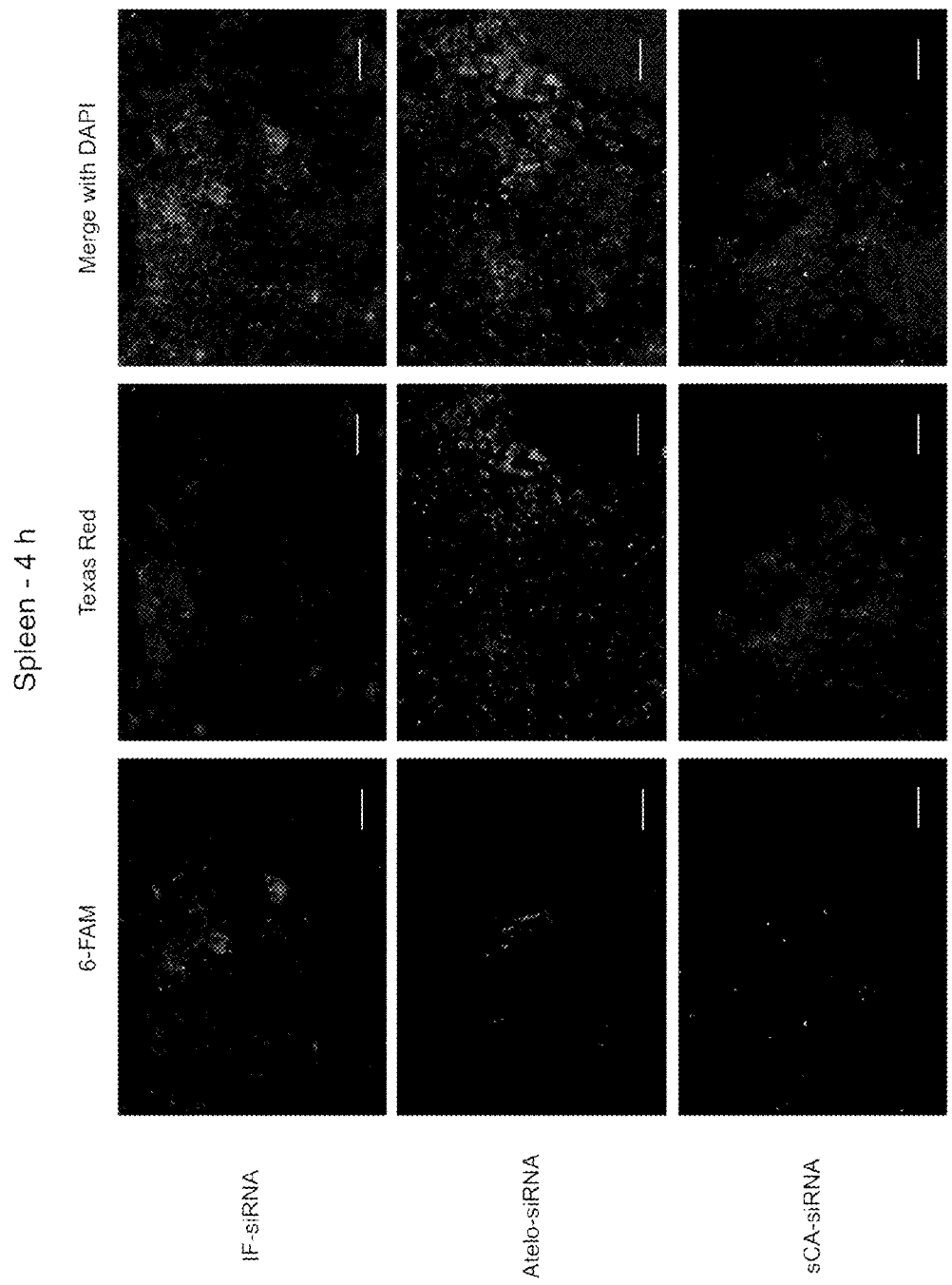
Figures 2, 16:
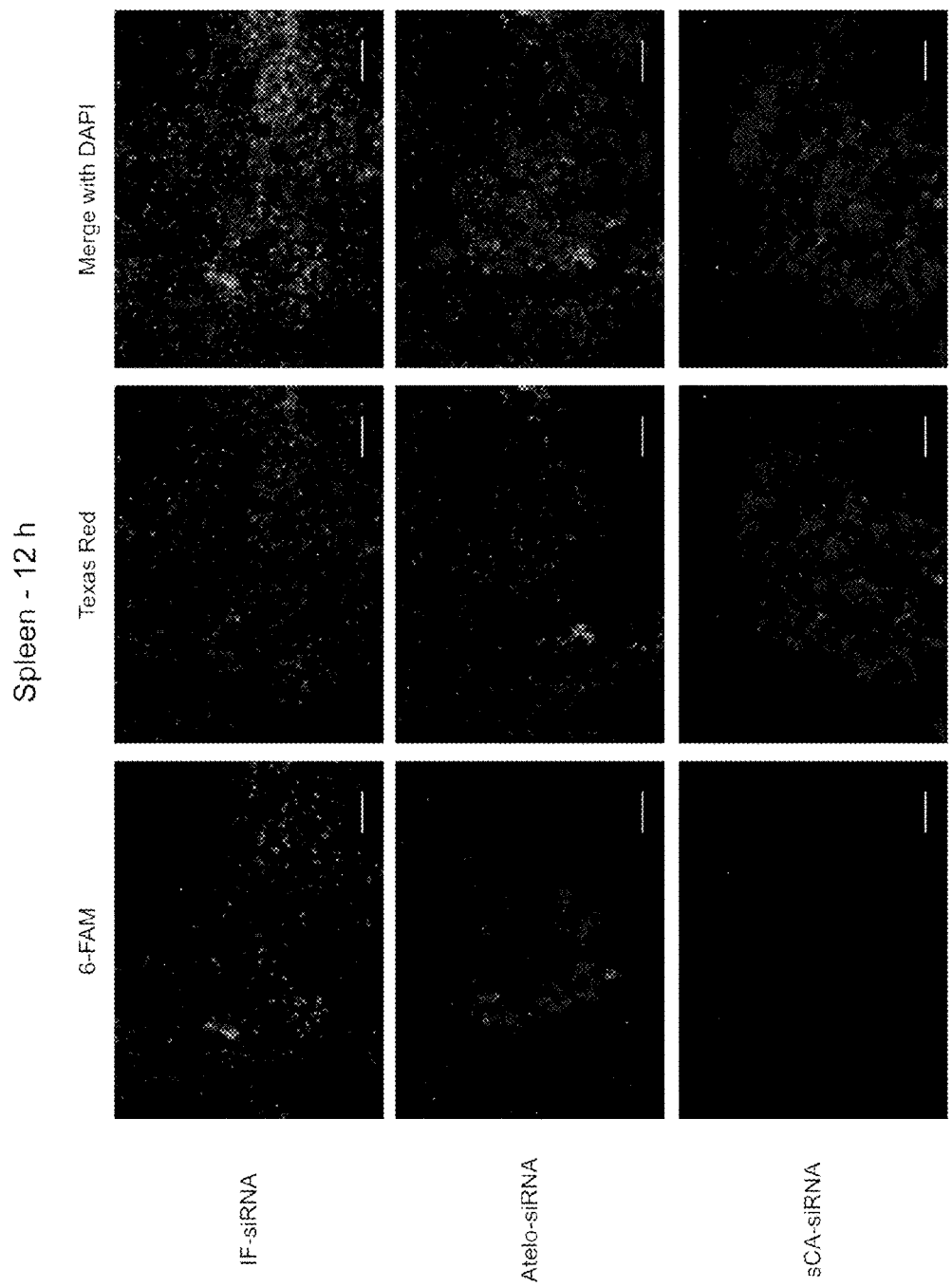
Figures 1, 17:
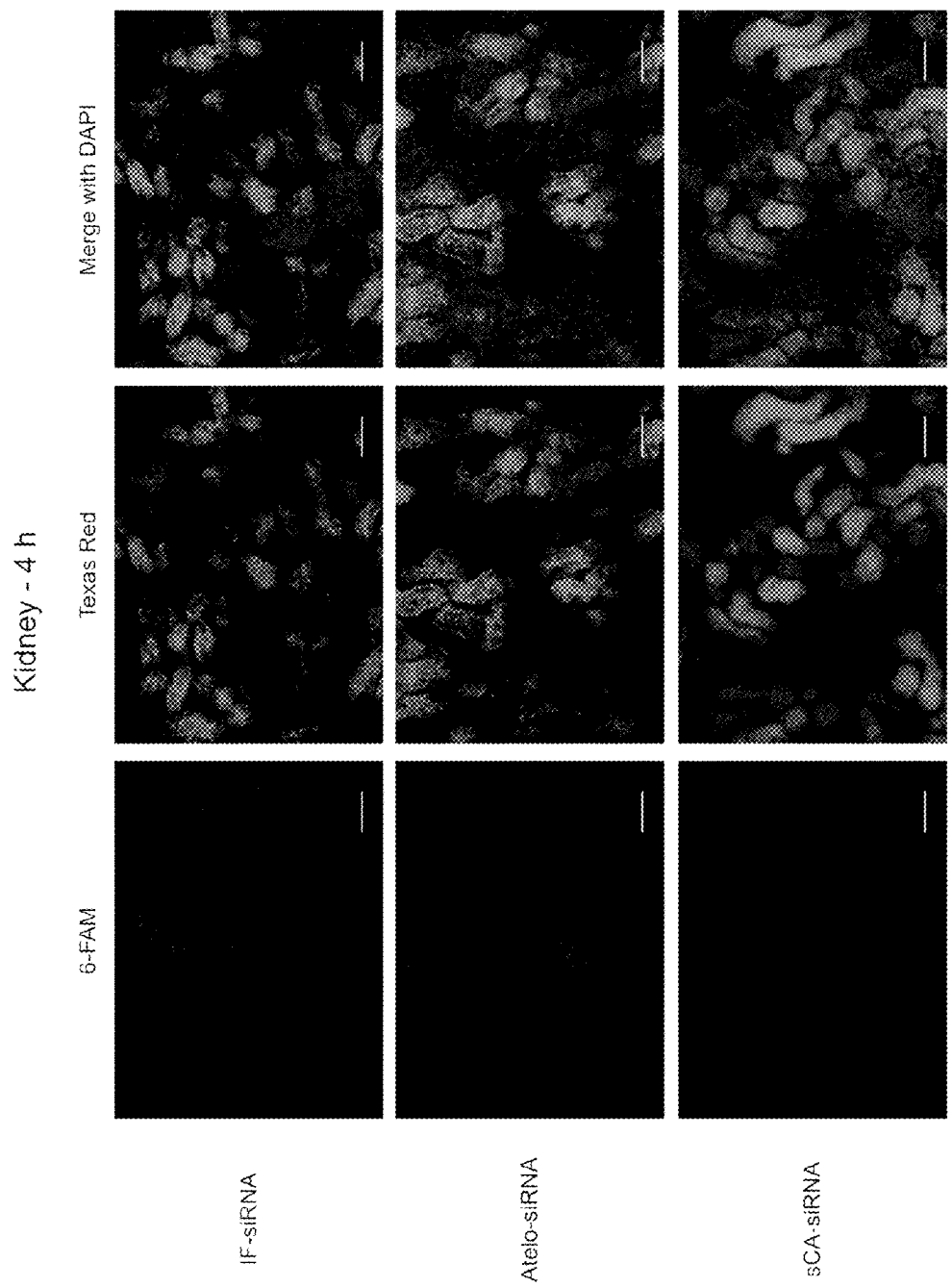
Figures 2, 17:
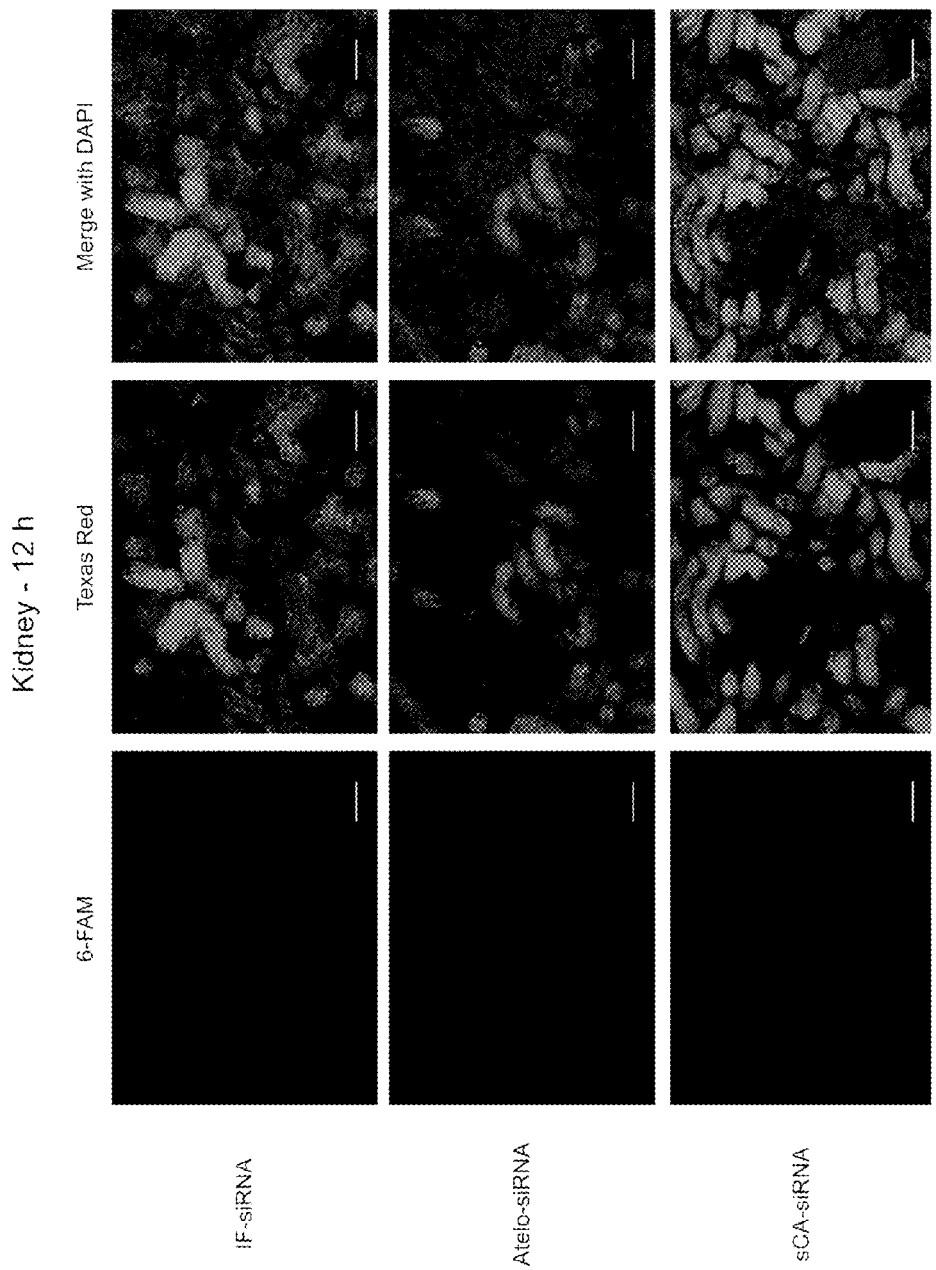

FIG. 15-1 shows an image of the liver 4 hours after the administration, FIG. 15-2 an image of the liver 12 hours after the administration, and FIG. 15-3 an image (enlarged image) of the liver 4 hours after the administration. FIG. 16-1 shows an image of the spleen 4 hours after the administration, and FIG. 16-2 shows an image of the spleen 12 hours after the administration. FIG. 17-1 shows an image of the kidney 4 hours after the administration, and FIG. 17-2 shows an image of the kidney 12 hours after the administration. FIGS. 15-1 and 15-2 show that in the IF-siRNA administration group and the Atelo-siRNA administration group, the green fluorescence of 6-FAM was observed in the cytoplasm of liver cells (mainly around central veins) 4 hours and 12 hours after the administration. In the sCA-siRNA administration group, however, only very slight green fluorescence was observed in the liver. As is evident from the enlarged image of FIG. 15-3, the uptake of sCA-siRNA into the liver was very rare, whereas IF-siRNA was clearly taken up into the cytoplasm of liver cells. FIGS. 16-1 and 16-2 also show that in the IF-siRNA administration group and the Atelo-siRNA administration group, the green fluorescence of 6-FAM was clearly observed in the spleen, whereas in the sCA-siRNA administration group, the green fluorescence was hardly observed in the spleen. On the other hand, in all the administration groups, the green fluorescence was hardly observed in the kidney.

Figure 18:
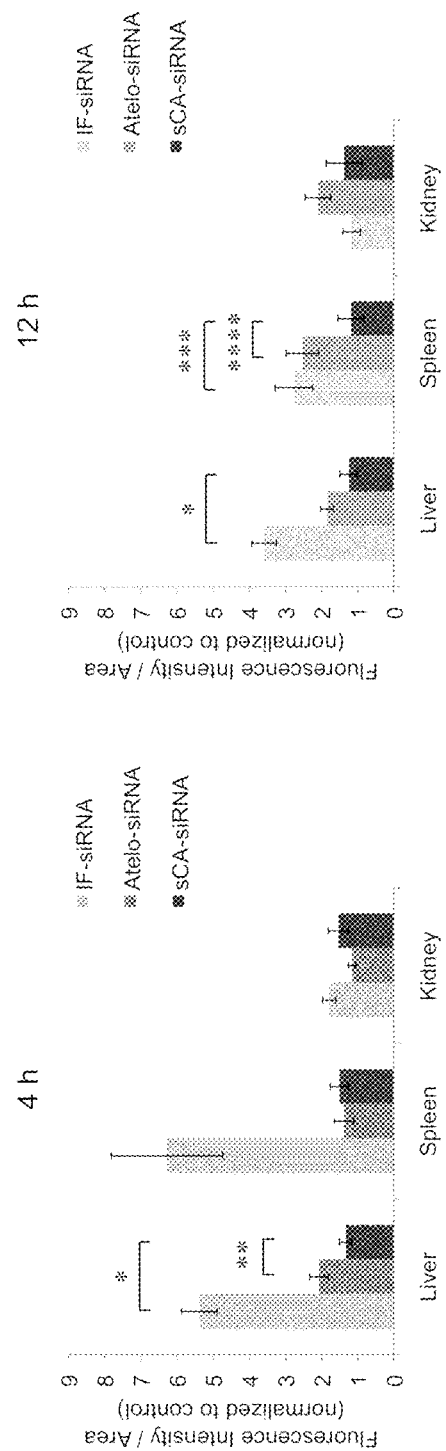
FIG. 18 shows the results of analysis of the accumulation in the liver, kidney, and spleen of a tumor-bearing model mouse intravenously injected with siRNA-containing carbonate apatite nanoparticles.

FIG. 18 shows the results of the analysis of the fluorescence intensity detected in the liver, spleen, and kidney in each administration group. Four hours after the administration, the fluorescence intensity of the liver in the sCA-siRNA administration group was 4.0 times or 1.6 times lower than that in the IF-siRNA administration group or the Atelo-siRNA administration group (P<0.0001 and P=0.014, respectively). Twelve hours after the administration, the fluorescence intensity of the liver in the sCA-siRNA administration group was 2.9 times lower than that in the IF-siRNA administration group (P<0.0001). Twelve hours after the administration, the fluorescence intensity of the spleen in the sCA-siRNA administration group was 2.3 times or 2.1 times lower than that in the IF-siRNA administration group or the Atelo-siRNA administration group (P=0.004 and P=0.017, respectively). No significant difference in the fluorescence intensity of the kidney was observed between the respective administration groups.

Results of Evaluation of Uptake into Tumor Tissue

Figure 19:
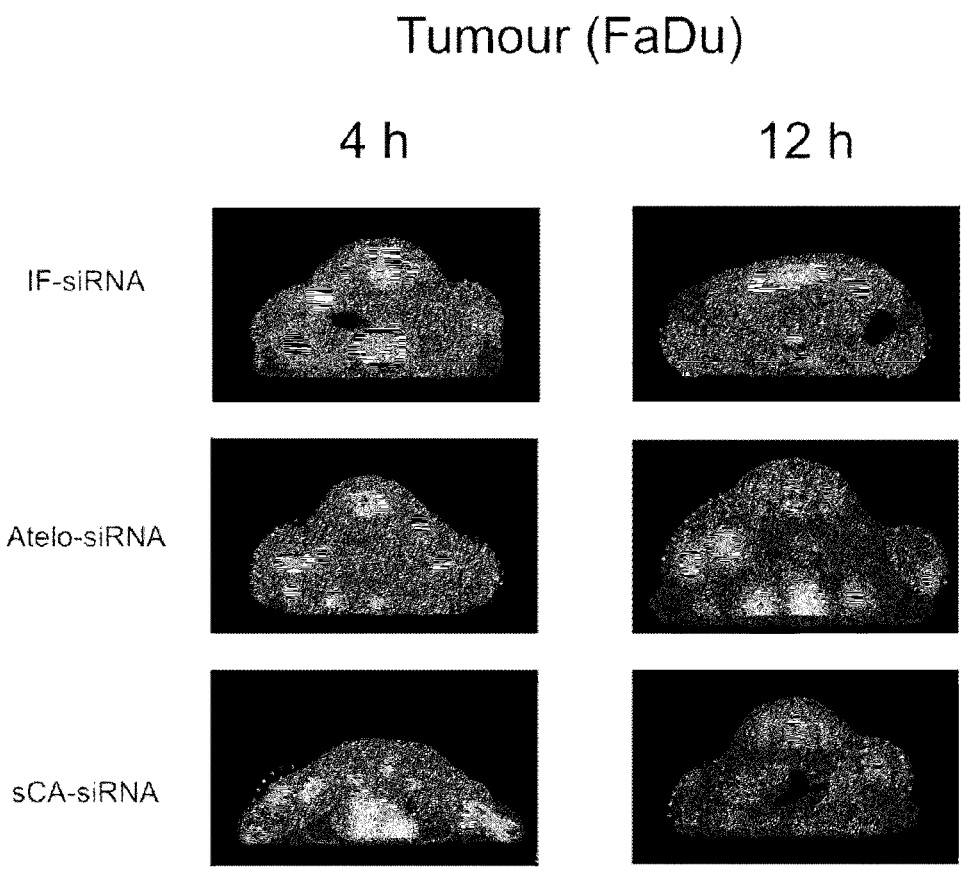
FIG. 19 is a three-dimensional in vivo image showing a distribution of siRNA-containing carbonate apatite nanoparticles in a FaDu tumor-bearing model mouse intravenously injected with siRNA-containing carbonate apatite nanoparticles.

FIG. 19 shows the results of taking three-dimensional in vivo images of the FaDu tumor in FaDu tumor-bearing mice 4 hours and 12 hours after the administration. These results show that 4 hours after the administration, the fluorescence of Alexa Fluor 750 was not observed in the FaDu tumor in the IF-siRNA administration group and the Atelo-siRNA administration group, but accumulation of the Alexa Fluor 750 fluorescence was observed at the center of the FaDu tumor in the sCA-siRNA administration group 4 hours after the administration.

Figure 20:
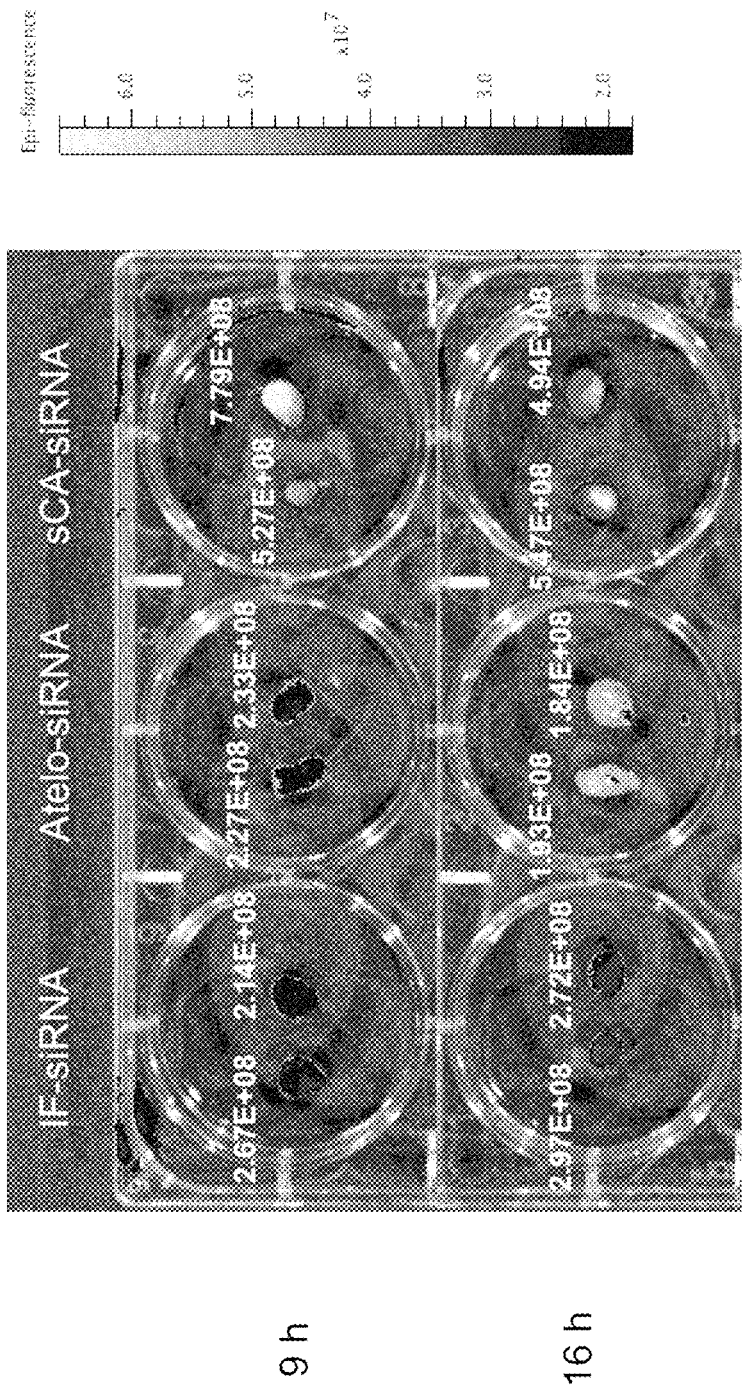
FIG. 20 shows the results of ex vivo imaging analysis of the FaDu tumor taken out of a FaDu tumor-bearing model mouse intravenously injected with siRNA-containing carbonate apatite nanoparticles.
Figure 21:
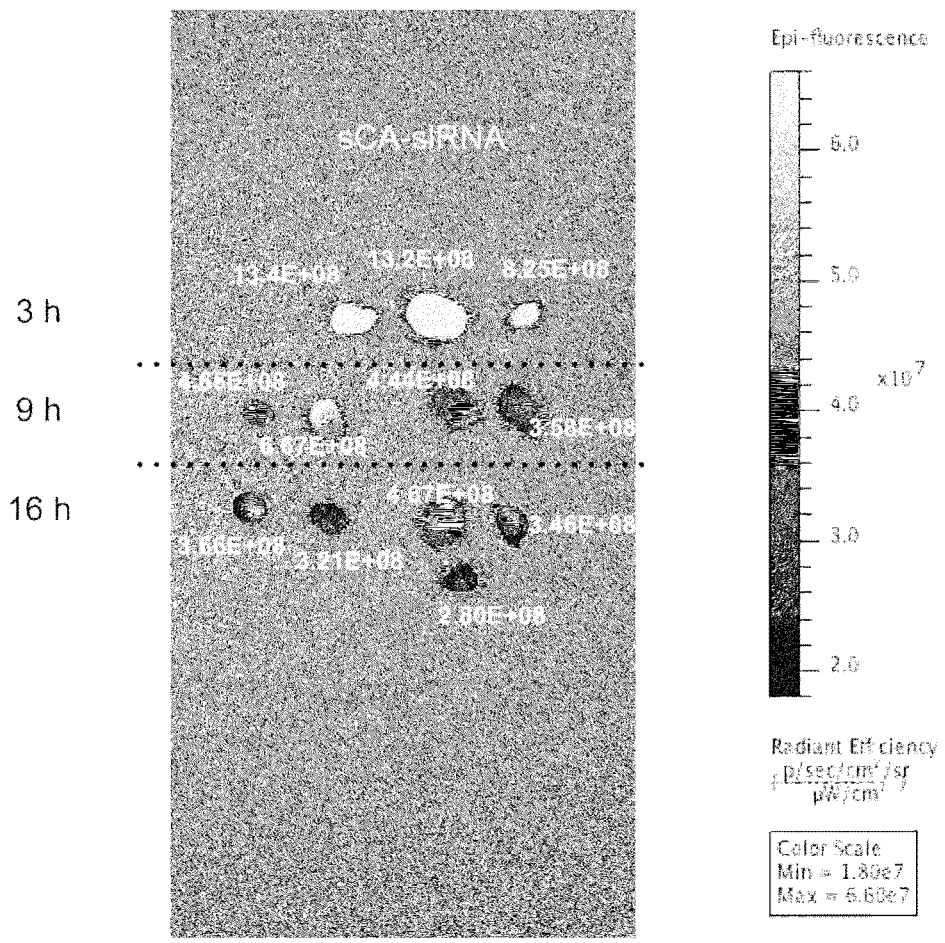
FIG. 21 shows the results of the measurement of the fluorescence intensity of Alexa Fluor 750 used to label siRNA in the FaDu tumor taken out of a FaDu tumor-bearing model mouse intravenously injected with siRNA-containing carbonate apatite nanoparticles.

FIG. 20 shows the results of ex vivo imaging analysis of the FaDu tumor taken out of the mice 9 hours and 16 hours after the administration. FIG. 20 shows that 9 hours and 16 hours after the administration, the fluorescence intensity per unit area of the FaDu tumor was higher in the sCA-siRNA administration group than in the other administration groups. In the sCA-siRNA administration group, stronger fluorescence from Alexa Fluor 750 was also observed in the FaDu tumor 3 hours after the administration (FIG. 21).

Figure 22:
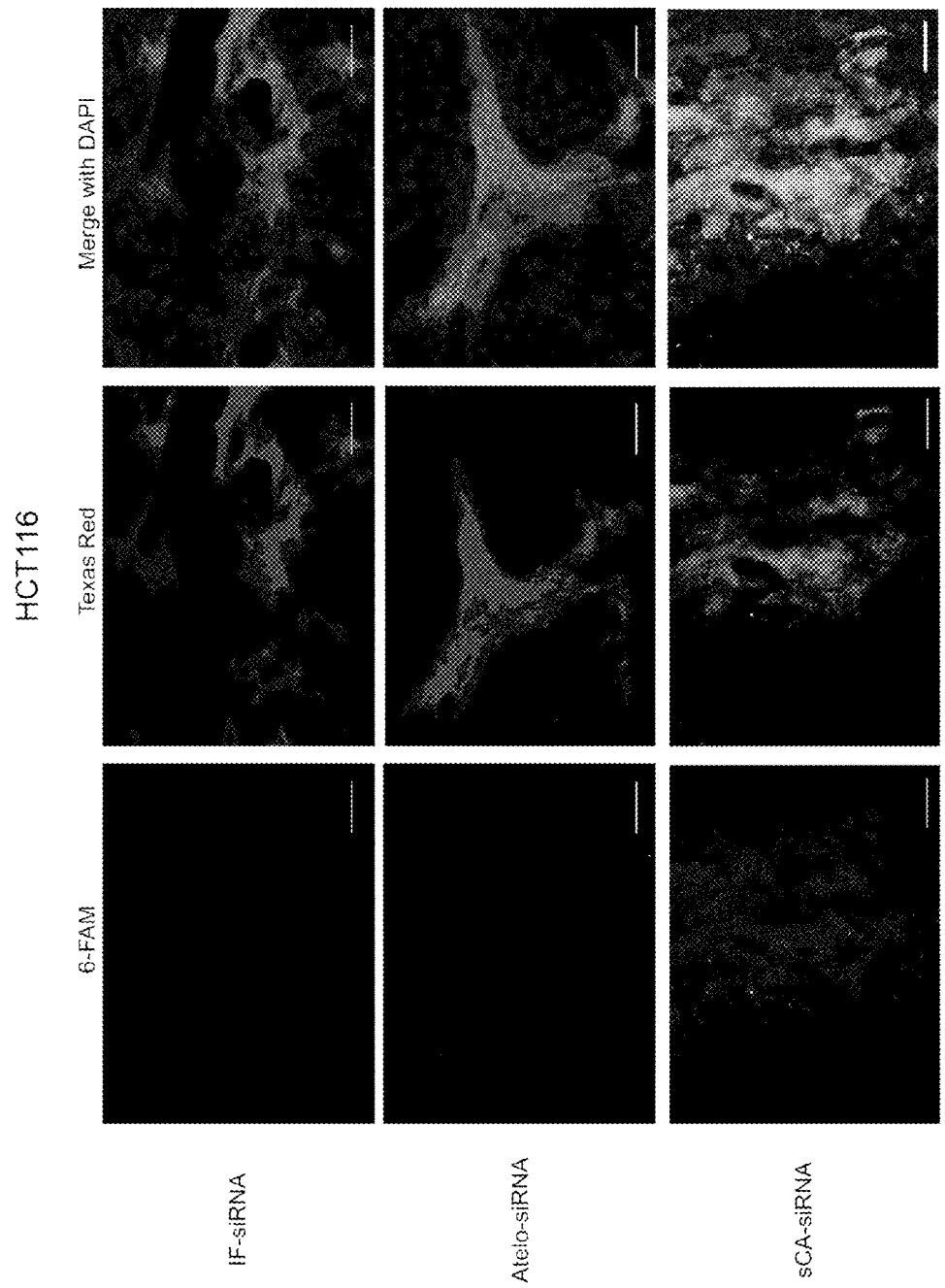
FIG. 22 shows whether or not carbonate apatite nanoparticles are accumulated in the HCT116 tumor of a HCT116 tumor-bearing model mouse after intravenous injection of siRNA-containing carbonate apatite nanoparticles.

Next, FIG. 22 shows the results of the fluorescence-microscopic measurement of siRNA contained in the HCT116 tumor of the HCT116 tumor-bearing mice. In the IF-siRNA administration group and the Atelo-siRNA administration group, no green signal was observed in the merged images 4 hours after the administration. In the sCA-siRNA administration group, however, leaching or penetrating green signals were observed in the merged images 4 hours after the administration.

Figure 23:
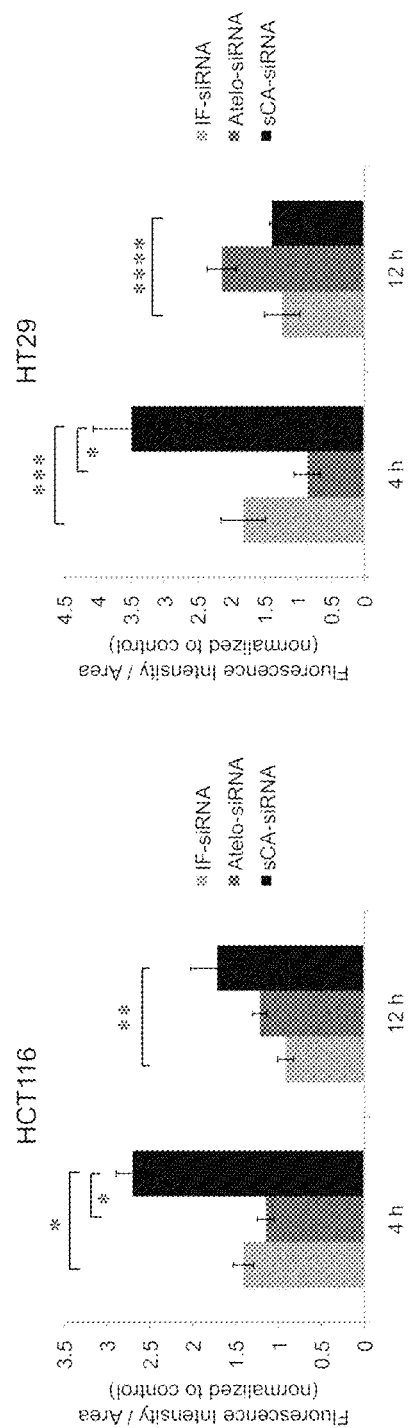
FIG. 23 shows the results of analysis of accumulation of carbonate apatite nanoparticles in each type of tumor of a HCT116 tumor- or HT29 tumor-bearing model mouse intravenously injected with siRNA-containing carbonate apatite nanoparticles.

FIG. 23 shows the results of the analysis of the fluorescence intensity detected in the HCT116 tumor and the HT29 tumor in each administration group. The results show that 4 hours after the administration, the green fluorescence intensity of the tumor was significantly higher in the sCA-siRNA administration group ($2.7 \pm 0.19$ times (mean$\pm$s.e.m) normalized to saline-treated-samples) than in the IF-siRNA administration group ($1.4 \pm 0.12$ times (mean$\pm$s.e.m) normalized to saline-treated-samples, $P<0.0001$) or than in the Atelo-siRNA administration group ($1.15 \pm 0.10$ times (mean$\pm$s.e.m) normalized to saline-treated-samples, $P<0.0001$). Twelve hours after the administration, the fluorescent intensity of the tumor was significantly higher in the sCA-siRNA administration group ($1.7 \pm 0.31$ times) than in the IF-siRNA administration group ($0.92 \pm 0.09$ times, $P=0.033$). Also in the H29 solid tumor-bearing mice, the fluorescence intensity of the tumor in the sCA-siRNA administration group increased $3.5 \pm 0.57$ times (mean$\pm$s.e.m., normalized to saline-treated samples) 4 hours after the administration, which was significantly higher than that of the tumor in the IF-siRNA administration group ($1.8 \pm 0.34$ times, normalized to saline-treated samples, $P=0.0051$) or than that of the tumor in the Atelo-siRNA administration group ($0.85 \pm 0.20$ times, normalized to saline-treated samples, $P<0.0001$).

Figure 24:
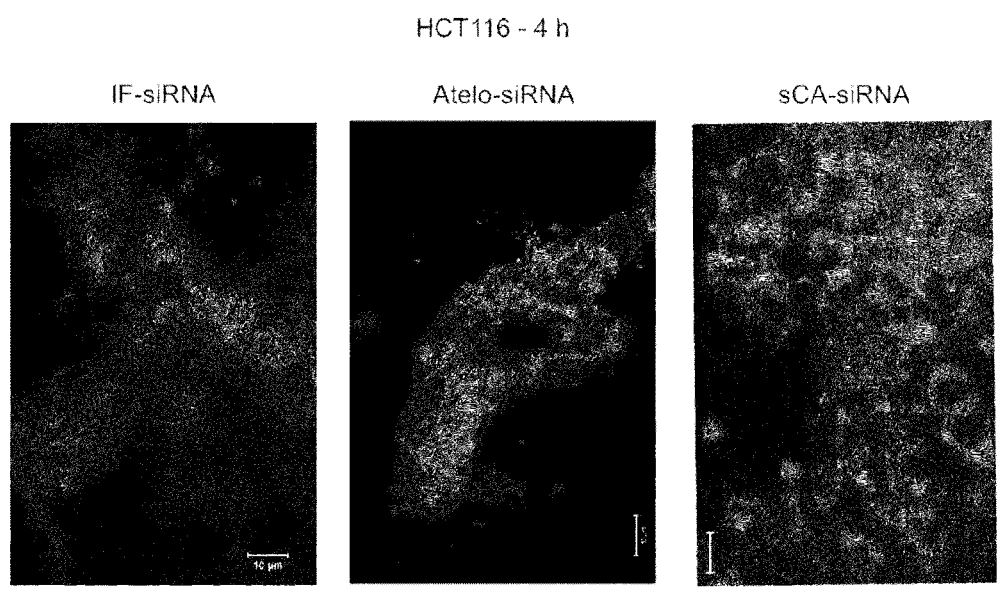
FIG. 24 shows the results of light sheet fluorescence microscopy analysis of accumulation of carbonate apatite nanoparticles in the HCT116 tumor of a HCT116 tumor-bearing model mouse intravenously injected with siRNA-containing carbonate apatite nanoparticles.

In light sheet fluorescence microscopy, accumulation of sCA-siRNA in the cytoplasm of HCT116 cells was observed 4 hours after the administration (FIG. 24). In contrast, no accumulation of IF-siRNA or Atelo-siRNA in HCT116 cells was observed (FIG. 24).

These results in Example 6 show that carbonate apatite nanoparticles are advantageous in that they are less likely to accumulate in liver, kidney, spleen, and so on and more likely to accumulate in tumor tissues than known drug delivery carriers.

Example 7

Evaluation 1 of the Function of Substance Introduced with Carbonate Apatite Nanoparticles The examples described above show that the use of carbonate apatite nanoparticles makes it possible to more efficiently introduce substances into tumor cells. Thus, whether or not siRNA introduced using carbonate apatite nanoparticles can actually function in cells was examined using anti-survivin siRNA (manufactured by KOKEN CO., LTD.). Carbonate apatite nanoparticles containing anti-survivin siRNA were prepared according to the procedure (3) of Example 1.

Figure 25:
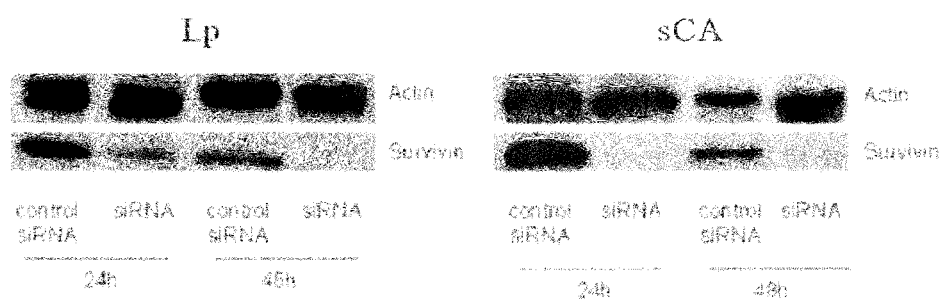
FIG. 25 shows the results of functional analysis of anti-survivin siRNA-containing carbonate apatite nanoparticles-induced suppression of target gene protein expression in HCT116 cells.

Lipofectamine 2000 containing anti-survivin siRNA was prepared according to the product protocol. These materials were introduced into HCT116 as in Example 4 using a medium containing 100 pmol/well of the siRNA. Subsequently, 24 hours and 48 hours after the introduction, the presence of survivin protein was checked by western blot. The results are shown in FIG. 25. In FIG. 25, the results obtained with Lipofectamine 2000 are shown on the left, and the results obtained with the carbonate apatite nanoparticles are shown on the right. FIG. 25 shows that when Lipofectamine 2000 was used, survivin protein completely disappeared after 48 hours, but when the carbonate apatite nanoparticles were used, survivin protein completely disappeared after 24 hours. This shows not only that siRNA introduced using carbonate apatite nanoparticles can function in cells but also that the use of carbonate apatite nanoparticles makes it possible to introduce siRNA into cells more quickly than the use of Lipofectamine and to allow siRNA to function in cells.

Example 8

Evaluation 2 of the Function of Substance Introduced with Carbonate Apatite Nanoparticles Following Example 7, the effect on the HCT116 cell growth was evaluated using WST-8 assay (manufactured by DOJINDO LABORATORIES). HCT116 cells were uniformly seeded on 96-well plates ($1 \times 10^4$ cells/well) and cultured for 24 hours. The medium was then replaced by a fresh medium (100 µl) containing carbonate apatite nanoparticles containing anti-survivin siRNA or by a fresh medium (100 µl) containing Lipofectamine 2000 containing anti-survivin siRNA. The fresh medium contained siRNA at a concentration of 5 pmol/well. Subsequently, 48 hours and 72 hours after the replacement, the cell survival rate was evaluated by spectrophotometric analysis using a microplate reader (680XR manufacture by Bio-Rad Laboratories, Inc.).

Figure 26:
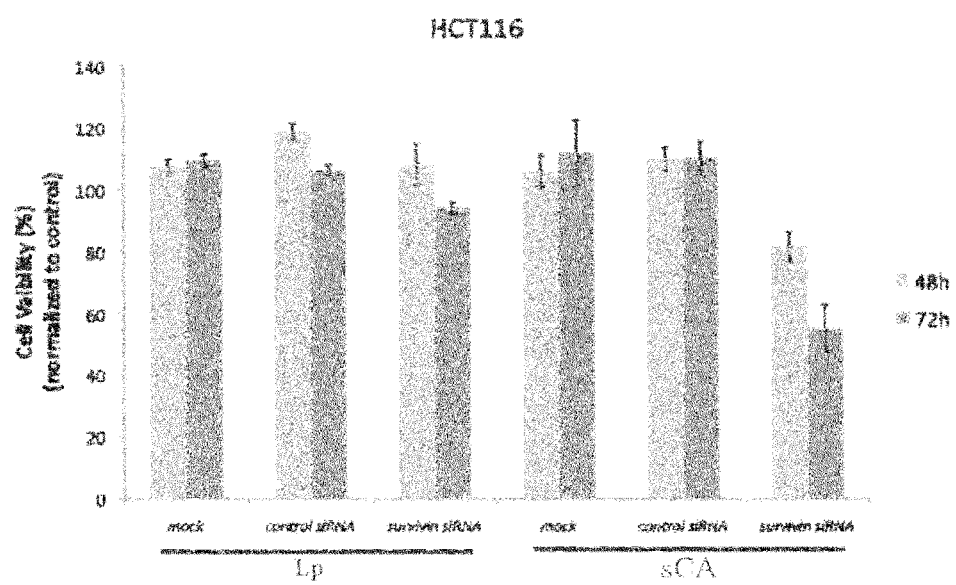
FIG. 26 shows the results of the examination of the effect on the cell survival rate when anti-survivin siRNA-containing carbonate apatite nanoparticles were transfected into HCT116 cells.

The results are shown in FIG. 26. FIG. 26 shows that a significant reduction in the cell survival rate was observed only when anti-survivin siRNA was introduced using the carbonate apatite nanoparticles.

Example 9

Evaluation 1 of Antitumor Activity Using Tumor Model Mice

HCT116-derived tumor-bearing mice were produced as in Example 5. The day when the tumor size reached 5 to 6 mm was designated as day 0. On days 0, 2, 4, 7, 9, 11, 14, 16, and 18, each sample was administered as shown in Table 2 through tail vein to the mice in such a manner that 15 µg of siRNA was administered to each mouse.

TABLE 2

| | |
|---|---|
| Saline administration group | Administered with saline |
| IF-control-siRNA administration group | Administered with Invivofectamine 2.0 (manufactured by Invitrogen) containing control siRNA (manufactured by KOKEN CO., LTD.) (IF- |

TABLE 2-continued

| | |
|---|---|
| IF-survivin-siRNA administration group | control-siRNA). Prepared according to the product protocol. Administered with Invivofectamine 2.0 (manufactured by Invitrogen) containing anti-survivin siRNA (manufactured by KOKEN CO., LTD.) (IF-survivin-siRNA). Prepared according to the product protocol. |
| Atelo-control-siRNA administration group | Administered with AteloGene (manufactured by KOKEN CO., LTD.) containing control siRNA (manufactured by KOKEN CO., LTD.) (Atelo-control-siRNA). Prepared according to the product protocol. |
| Atelo-survivin-siRNA administration group | Administered with AteloGene (manufactured by KOKEN CO., LTD.) containing anti-survivin siRNA (manufactured by KOKEN CO., LTD.) (Atelo-survivin-siRNA). Prepared according to the product protocol. |
| sCA-control-siRNA administration group | Administered with carbonate apatite nanoparticles containing control siRNA (manufactured by KOKEN CO., LTD.) (sCA-control-siRNA). Prepared using the procedure (3) of Example 1. |
| sCA-survivin-siRNA administration group | Administered with carbonate apatite nanoparticles containing anti-survivin siRNA (manufactured by KOKEN CO., LTD.) (sCA-survivin-siRNA). Prepared using the procedure (3) of Example 1. |

The tumor size was measured on days 4, 7, 11, 14, and 18. The tumor size was calculated from the following formula: $V = a \times b^2/2$, wherein V represents the size, a the length, and b the breadth. The number n of samples is 10. On day 19, the tumor was taken out of the mice, embedded in O.C.T. compound, and stored at −80° C. The frozen sample was used and incubated with a polyclonal human anti-survivin antibody (Novus Biologicals) at a concentration of 1,000 times overnight, and then incubated with a second antibody (goat anti-rabbit IgG Alexa Fluor 633, Invitrogen). Subsequently, the sample was mounted with a DAPI-containing ProLong Gold antifade reagent (Invitrogen) and subjected to immunofluorescence staining.

In addition, 6 hours and 12 hours after the administration of each sample, blood was collected from each mouse and subjected to cytokine analysis (IFN-α, IL-6, TNF-α, and INF-γ). The mouse serum cytokine level was determined using a commercially available sandwich ELISA kit.

Figure 27:
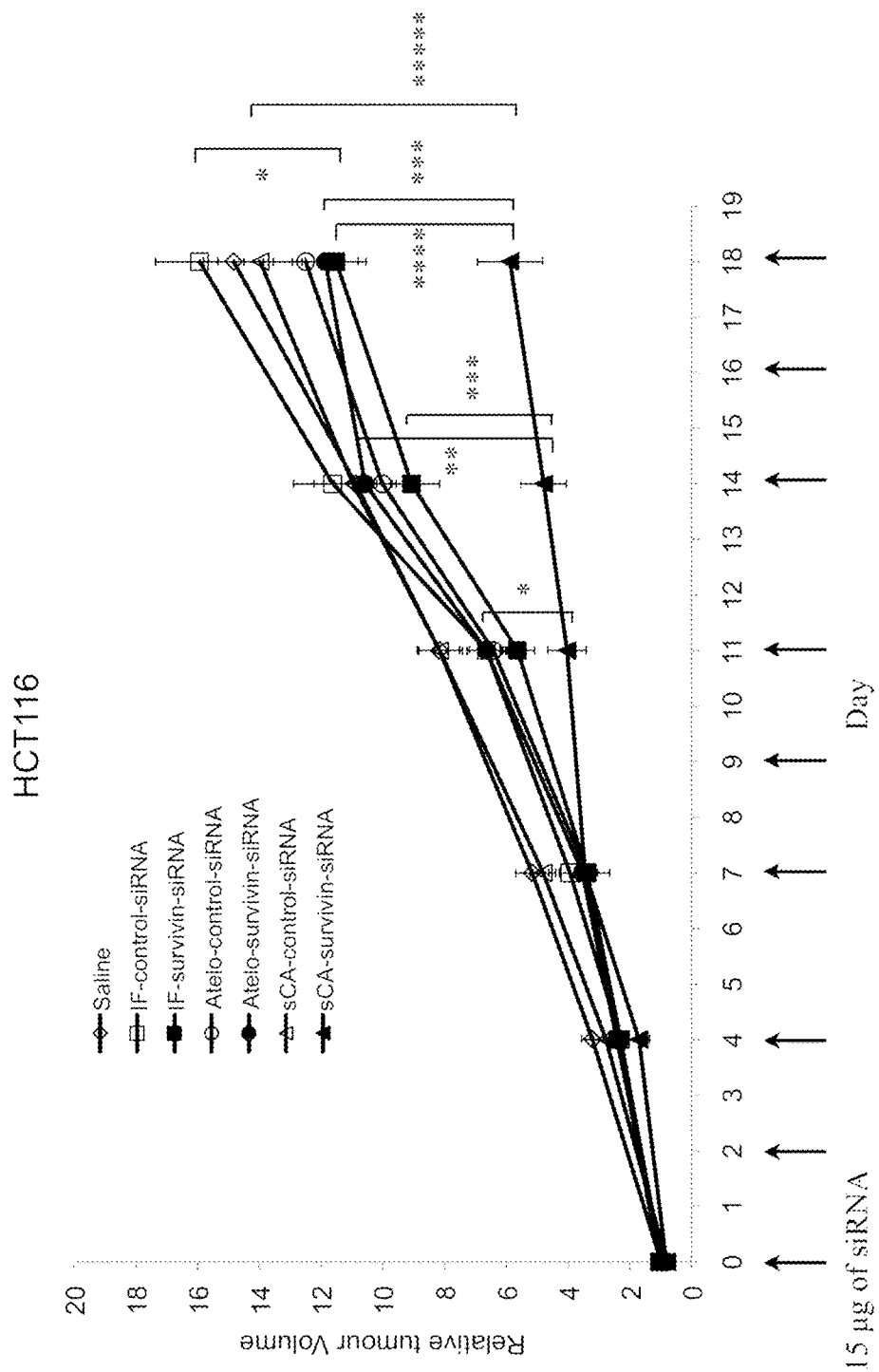
FIG. 27 shows the effect of anti-survivin siRNA-containing carbonate apatite nanoparticles on the tumor size of tumor-bearing model mice.

FIG. 27 shows the results of the measurement of the tumor size in each administration group. In the IF-survivin-siRNA administration group, a significant antitumor effect relative to that in the IF-control-siRNA administration group was observed only on day 18. The Atelo-survivin-siRNA administration group showed no significant antitumor effect as compared with the Atelo-control-siRNA administration group. On the other hand, the sCA-survivin-siRNA administration group showed an antitumor effect on day 11 and thereafter, and on day 18, the effect was superior to that in the other administration groups.

Figure 28:
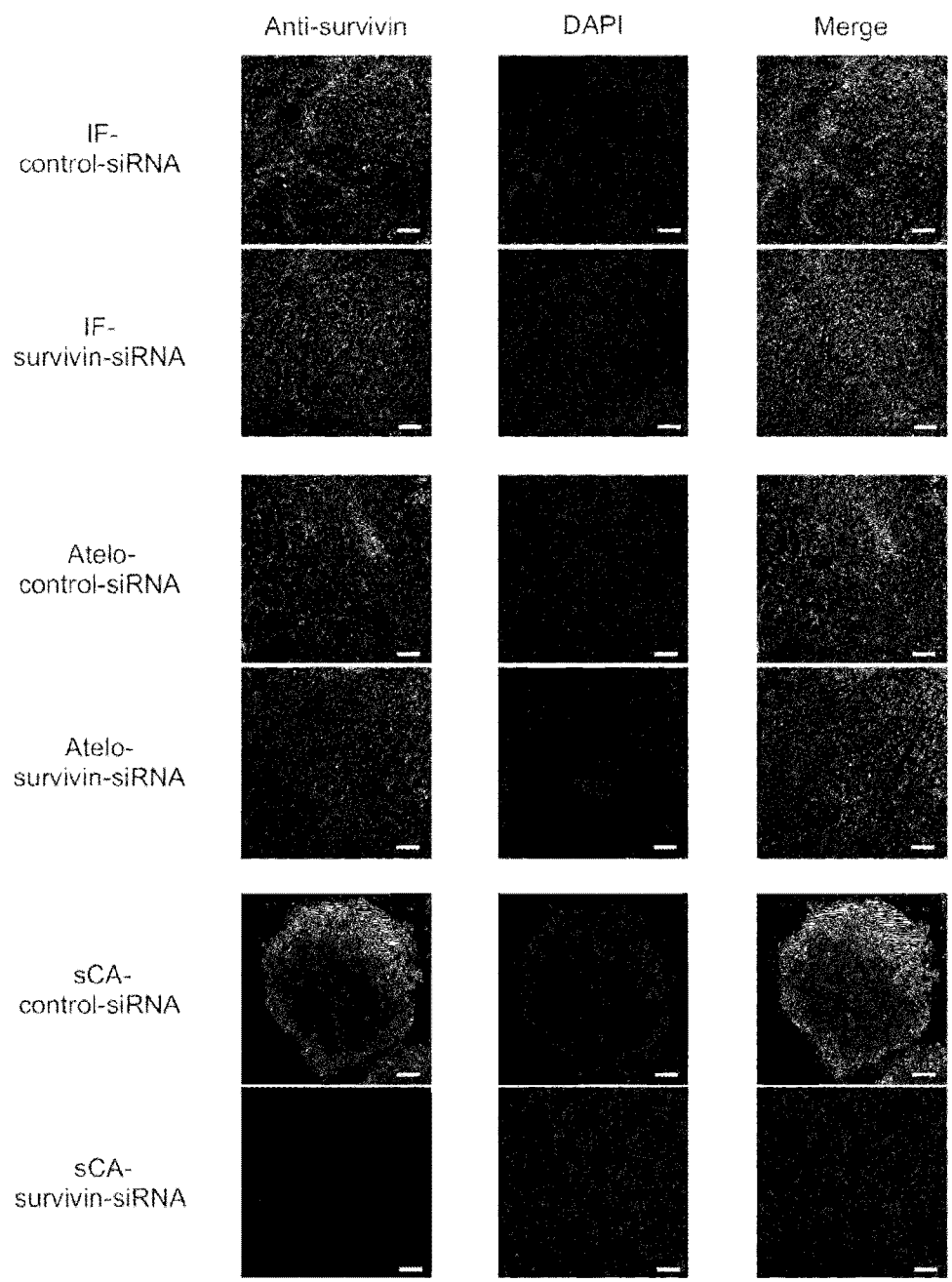
FIG. 28 shows the results of immunofluorescence staining of the tumor of tumor-bearing model mice administered with anti-survivin siRNA-containing carbonate apatite nanoparticles.
Figure 29:
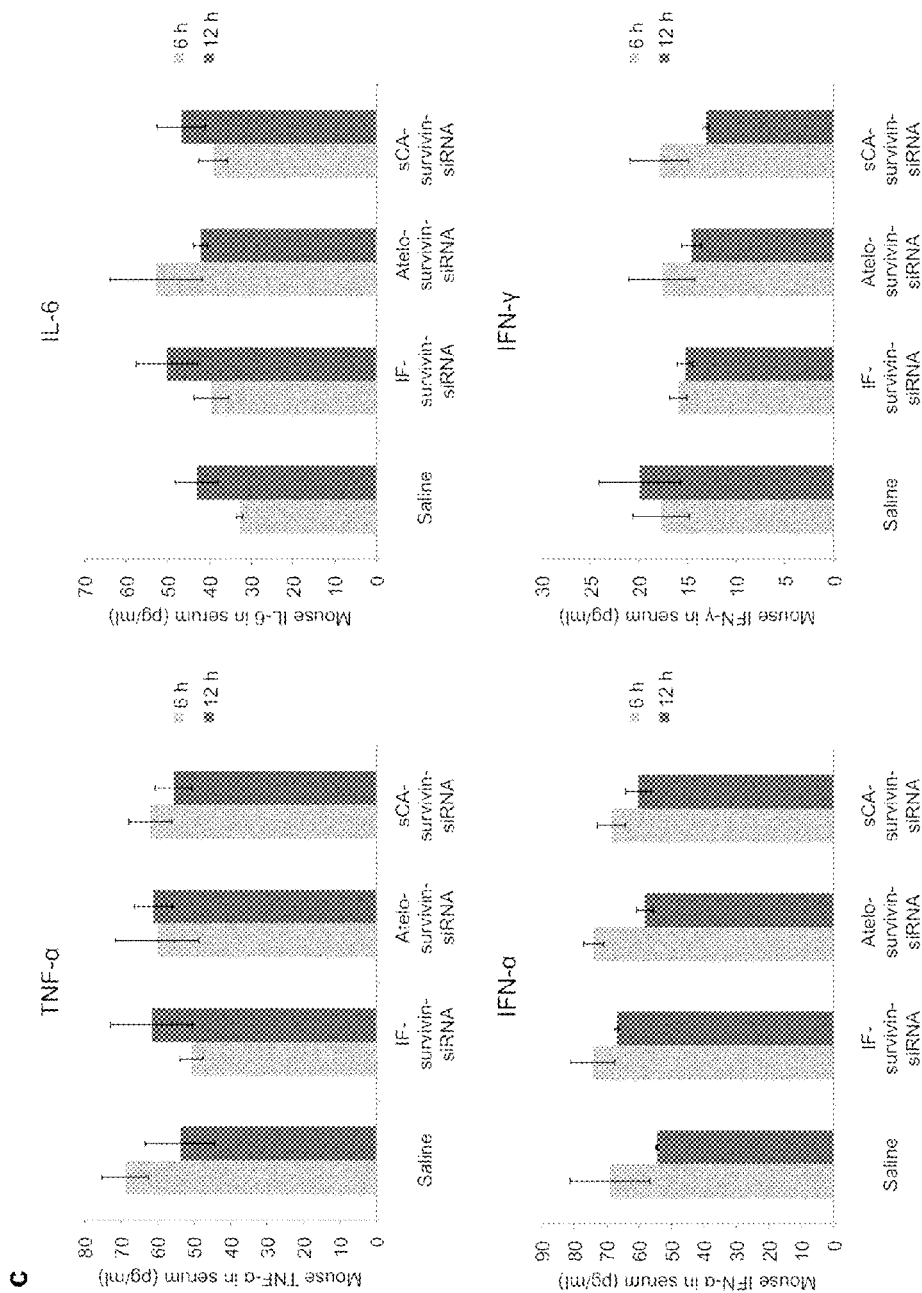
FIG. 29 shows the results of the measurement of the concentration of IFN-α, IL-6, TNF-α, and INF-γ in the serum of tumor-bearing model mice administered with anti-survivin siRNA-containing carbonate apatite nanoparticles.

FIG. 28 shows the results of immunofluorescence staining of the tumor taken out of the mouse on day 19. Knockdown of survivin expression was observed only in the sCA-survivin-siRNA administration group. Tumor necrosis factors IFN-α, IL-6, TNF-α, and INF-γ did not increase in all administration groups (FIG. 29). This shows that the antitumor effect of sCA-survivin-siRNA is not caused by a specific sequence siRNA-induced increase in immune response.

Example 10

Evaluation 2 of Antitumor Activity Using Tumor Model Mice

HT29 human colon cancer cells were subcutaneously injected into the left and right backs of 7 week-old BALB/cA nude mice (produced by CLEA Japan, Inc.), so that solid tumor-bearing model mice were produced. The day when the tumor size reached 10 mm was designated as day 0. On days 0, 1, and 2, each sample was administered as shown in Table 3 through tail vein to the mice in such a manner that 40 μg of siRNA was administered at each time.

TABLE 3

| | |
|---|---|
| Saline administration group | Administered with saline |
| Naked-survivin-siRNA administration group | Administered with saline containing 40 μg of fluorescent 6-FAM-labeled anti-survivin siRNA (manufactured by KOKEN CO., LTD.) |
| sCA-survivin-siRNA administration group | Administered with carbonate apatite nanoparticles containing 6-FAM-labeled anti-survivin siRNA (manufactured by KOKEN CO., LTD.) (sCA-survivin-siRNA). Prepared using the procedure (3) of Example 1. |

Figure 30:
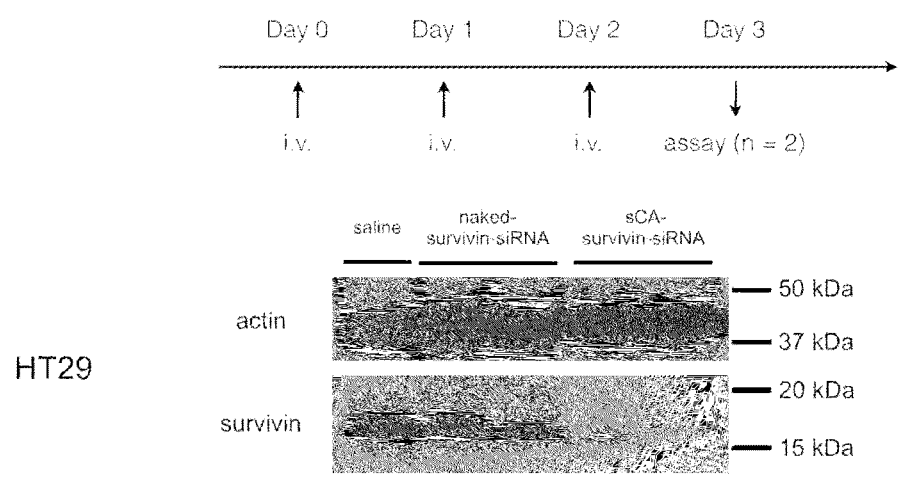
FIG. 30 shows the results of western blot examination of the presence of survivin protein in the tumor taken out of a tumor-bearing model mouse administered with anti-survivin siRNA-containing carbonate apatite nanoparticles.

On day 3, the tumor was taken out and subjected to western blot examination of the presence of survivin protein. The results are shown in FIG. 30. The results show that three consecutive administrations of sCA-survivin-siRNA significantly reduced the expression of survivin protein.

Figure 31:
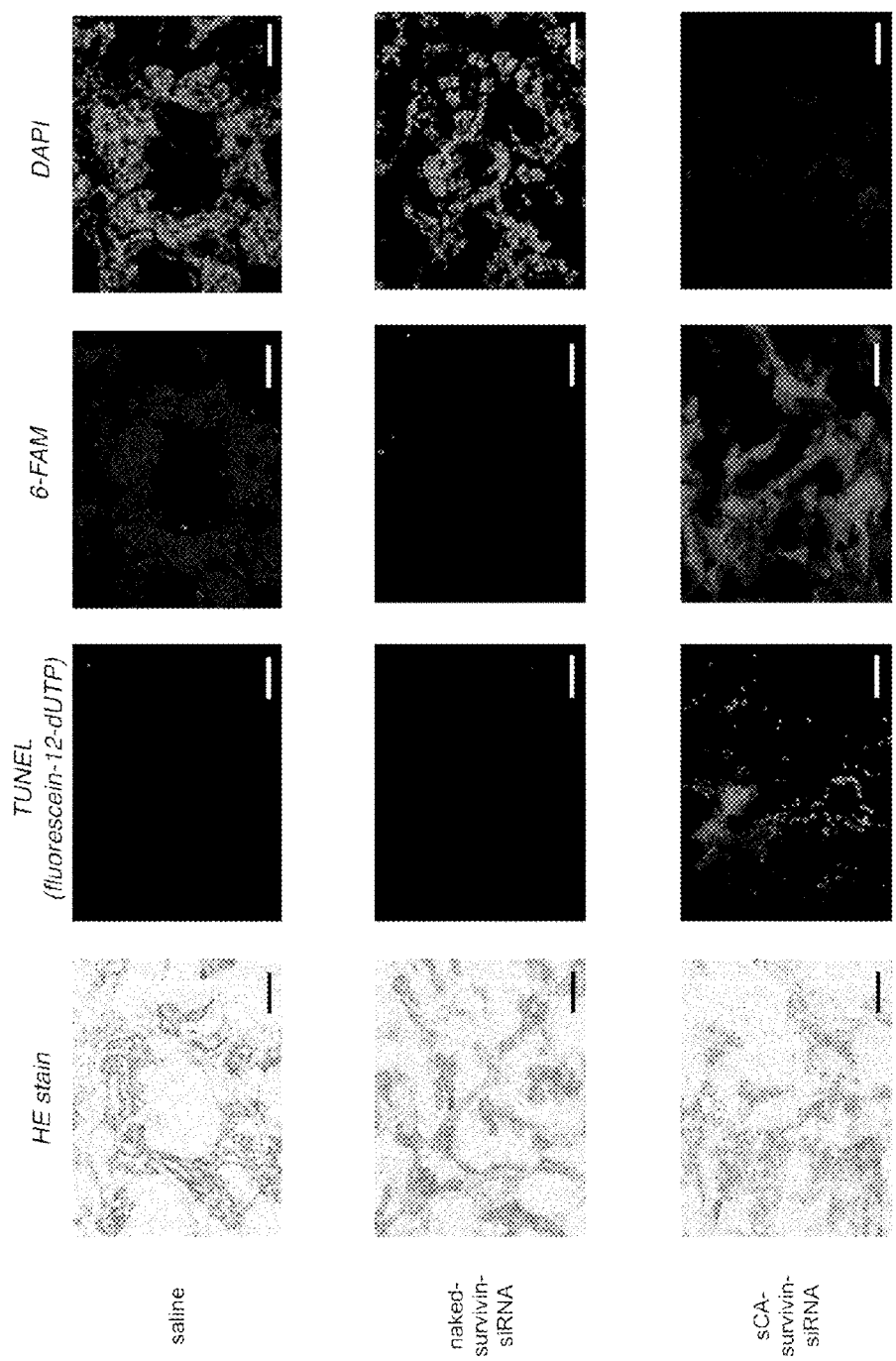
FIG. 31 shows the results of the measurement of the fluorescence of anti-survivin siRNA and 12-dUTP apoptosis signal in the tumor taken out of a tumor-bearing model mouse administered with anti-survivin siRNA-containing carbonate apatite nanoparticles.

The tumor taken out on day 3 was also subjected to the detection of apoptosis cells using DeadEnd Fluorometric TUNEL System (Promega) according to the manufacturer's protocol. The DNA fragment of apoptosis cells was detected by coupling fluorescein-12-dUTP to the 3'-OH end of the DNA with a catalyst. The fluorescence of the 6-FAM-labeled anti-survivin siRNA and 12-dUTP apoptosis signal was observed in the tumor in the sCA-survivin-siRNA administration group, but not detected in the tumor in the Saline administration group and the naked-survivin-siRNA administration group (FIG. 31).

Example 11

Antitumor Effect of Anticancer Agent-Containing Carbonate Apatite Nanoparticles

To 100 ml of distilled water were added 0.37 g of $NaHCO_3$, 90 μl of $NaH_2PO_4 \cdot 2H_2O$ (1M), and 180 μl of $CaCl_2$ (1 M) in this order, and dissolved. The pH of the solution was adjusted to 7.5 with 1N HCl. The solution was filtered through a 0.2 μm size filter. Doxorubicin-containing carbonate apatite nanoparticles necessary for a single intravenous dose per 20 g mouse were prepared as follows. Specifically, 1.28 ml of doxorubicin (5 mM) and 200 μl of $CaCl_2$ (1 M) were mixed per 40 ml of the resulting buffer, and the mixture was incubated in a water bath at 37° C. for 30 minutes. Subsequently, the mixture was centrifuged at 15,000 rpm for 5 minutes. The resulting pellet was dissolved in 250 μl of a saline solution. The solution was then subjected to an ultrasonic vibration treatment for 10 minutes, so that doxorubicin-containing carbonate apatite nanoparticles were obtained.

Figure 32:
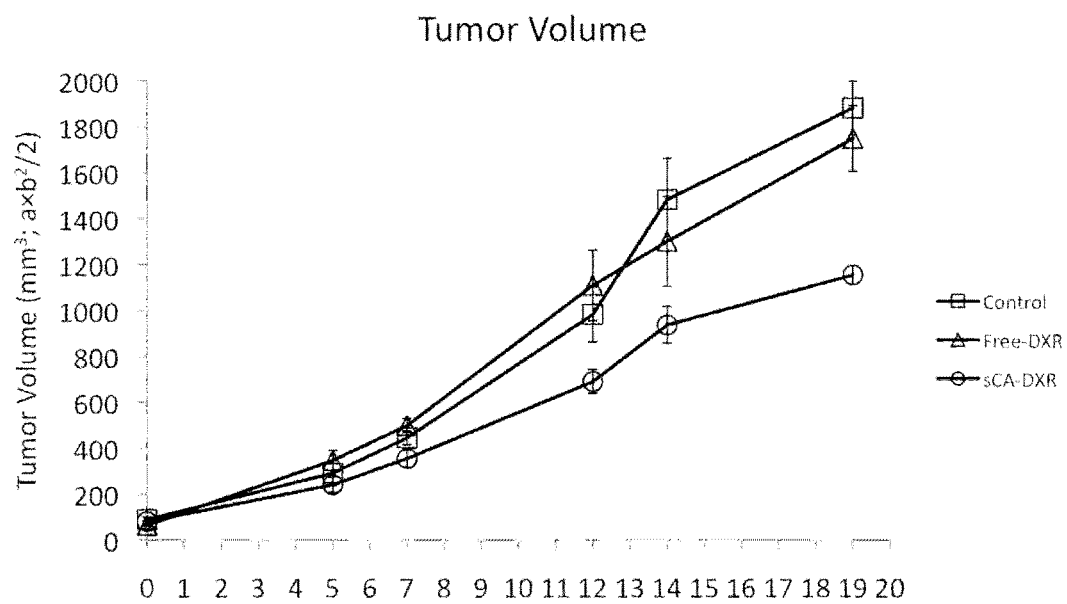
FIG. 32 shows the effect of doxorubicin-containing carbonate apatite nanoparticles on the tumor size of tumor-bearing model mice.

HCT116 human colon cancer cells ($5.0 \times 10^6$ cells) were subcutaneously injected into the left and right backs of 7 week-old BALB/cA nude mice (produced by CLEA Japan, Inc.), so that solid tumor-bearing model mice were produced. At the time when the tumor size reached 5 to 6 mm, the mice were randomly divided into three groups: a control group, a doxorubicin alone administration group, and a doxorubicin-containing carbonate apatite nanoparticles administration group. On days 0, 1, 2, 7, 8, 9, 14, 15, and 16, the mice in the doxorubicin alone administration group were i.v. administered with doxorubicin in a dose of 0.33 mg/kg/day via tail vein, and the mice in the doxorubicin-containing carbonate apatite nanoparticles administration group were i.v. administered with the nanoparticles via tail vein in such a manner that the dose of doxorubicin was 0.33 mg/kg/day. The administration of doxorubicin-containing carbonate apatite nanoparticles was performed quickly (within 30 seconds) after the ultrasonic vibration treatment. The antitumor activity was measured based on the tumor size. The tumor size was calculated from the following formula: $V=a \times b^2/2$, wherein V represents the size, a the length, and b the breadth. The number n of samples is 6. The results are shown in FIG. 32. FIG. 32 shows that on days 12 and 19, the tumor size was significantly smaller in the doxorubicin-containing carbonate apatite nanoparticles administration group than in the control group or the doxorubicin alone administration group.

Example 12

Antitumor Effect of microRNA-Containing Carbonate Apatite Nanoparticles

Carbonate apatite nanoparticles containing microRNA (miR340, miR542-3p, and miR34a), which is known to have an antitumor effect, were evaluated for antitumor effect.

HCT116 human colon cancer cells were uniformly seeded on 24-well plates (about $3 \times 10^5$ cells/dish) and cultured overnight with a 10% fetal bovine serum-supplemented DMEM medium.

Carbonate apatite nanoparticles containing each microRNA or an siRNA transfection reagent (siPORT NeoFX/Amine manufactured by Ambion) containing each microRNA was added to the cultured cells of each line in such a manner that microRNA was at a concentration of 5 pmol/well, and the cells were cultured. Twenty-four hours, 48 hours, and 72 hours after the addition, each cell survival rate was measured. Carbonate apatite nanoparticles containing microRNA with a sequence not naturally occurring in cells or an siRNA transfection reagent (siPORT NeoFX/Amine manufactured by Ambion) containing such microRNA was used as a negative control.

Figure 33:
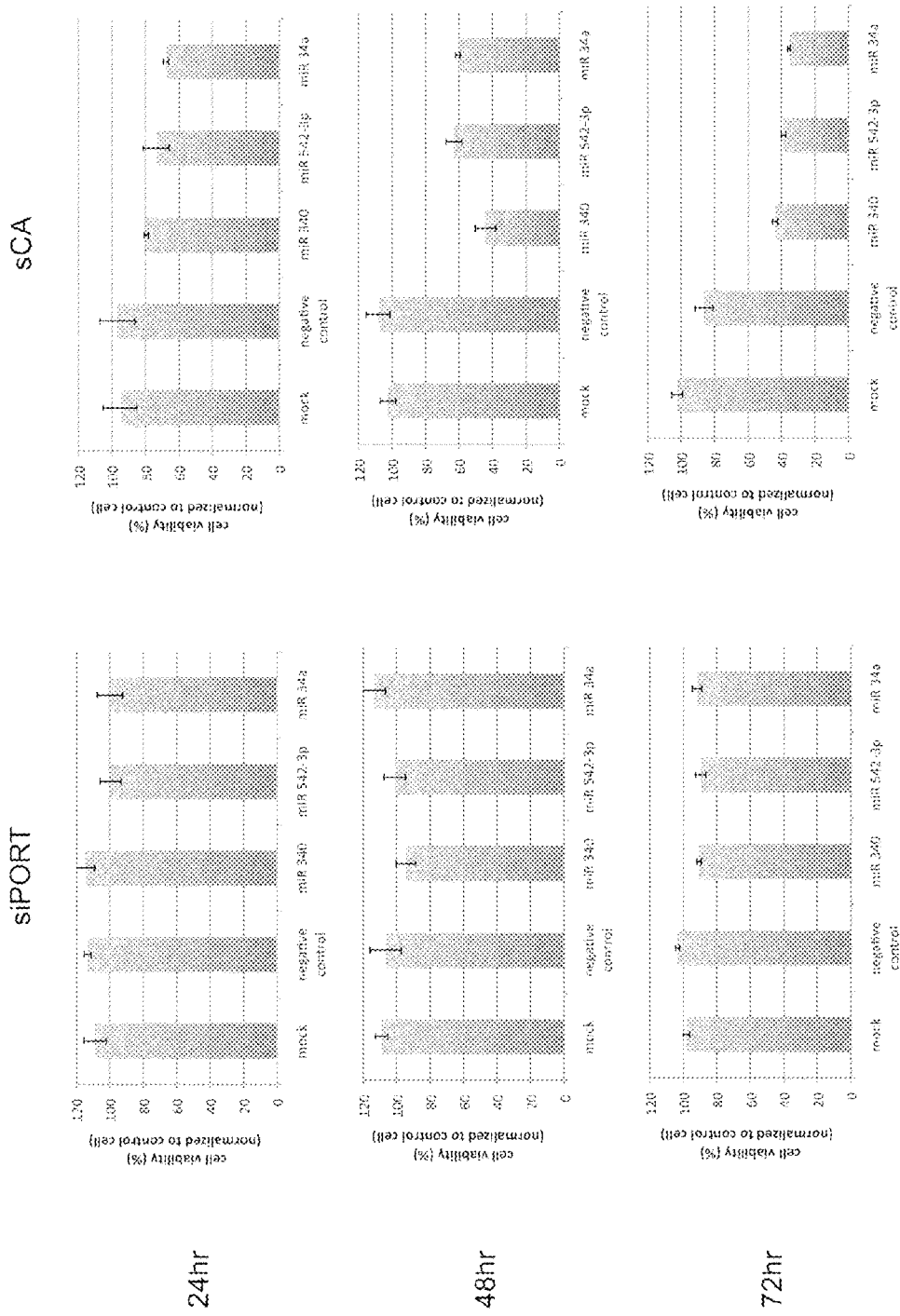
FIG. 33 shows the effect of antitumor miRNA-containing carbonate apatite nanoparticles on cancer cell growth.

The results are shown in FIG. 33. When a commercially available siRNA transfection reagent was used to introduce microRNA (miR340, miR542-3p, and miR34a), the cancer cell growth was not suppressed. However, when microRNA-containing carbonate apatite nanoparticles were used, the cancer cell growth was significantly suppressed.

Example 13

In Vivo Antitumor Effect of microRNA-Containing Carbonate Apatite Nanoparticles HCT116 human colon cancer cells were subcutaneously injected into the left and right backs of 7 week-old BALB/cA nude mice (produced by CLEA Japan, Inc.), so that solid tumor-bearing model mice were produced. The day when the tumor size reached 100 mm³ was designated as day 0. Each sample was administered as shown in Table 4 three times a week, every other day, via tail vein, and the tumor size was measured over time. The method of measuring the tumor size was the same as that in Example 10.

TABLE 4

| | |
|---|---|
| Saline administration group | Administered with saline |
| Cmab administration group | Administered with 1 mg/mouse of cetuximab at each time |

TABLE 4-continued

| | |
|---|---|
| sCA-miR4685 + Cmab administration group | Administered with a combination of 40 µg/mouse of sCA(2) particles (prepared in the production (2) of Example 1) and 1 mg/mouse of cetuximab at each time |
| sCA-miRNA-NC administration group | Administered with 40 µg of naked-miR4685 at each time |
| sCA-miRNA4685 administration group | Administered with miRNA4685-containing carbonate apatite nanoparticles in a dose of 40 µg (miRNA4685)/mouse at eachtime. The miRNA4685-containing carbonate apatite nanoparticles were prepared using the procedure (3) of Example 1. |
| sCA-miRNA4685 + Cmab administration group | Administered with a combination of 40 µg/mouse of miRNA4685-containing carbonate apatite nanoparticles and 1 mg/mouse of cetuximab at each time. The miRNA4685-containing carbonate apatite nanoparticles were administered in a dose of 40 µg miRNA4685. The miRNA4685-containing carbonate apatite nanoparticles were prepared using the procedure (3) of Example 1. |

Figure 34:
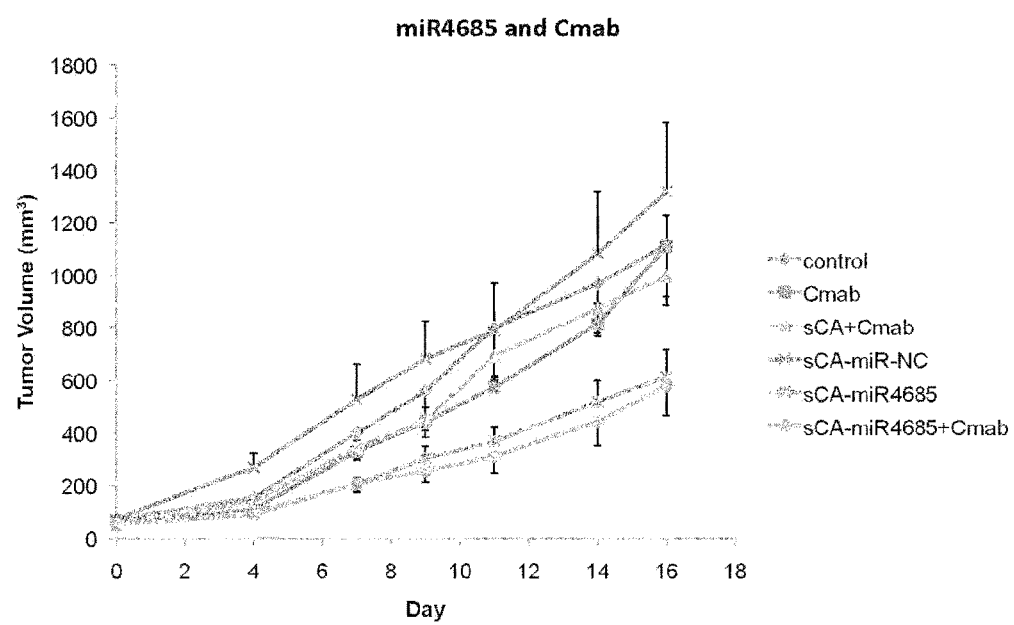
FIG. 34 shows the effect of antitumor miRNA-containing carbonate apatite nanoparticles on the tumor size of tumor-bearing model mice.

The results are shown in FIG. 34. On day 7 and thereafter, the tumor size was significantly smaller in the sCA-miRNA4685 administration group and the sCA-miRNA4685+Cmab administration group than in the other administration groups, and it was found that the use of carbonate apatite nanoparticles made possible efficient transfer of miRNA4685 to the tumor tissue.

Example 14

Evaluation of Toxicity of Carbonate Apatite Nanoparticles

On days 0, 2, 4, 6, 8, 10, and 12, the sCA(2) particles prepared in the production (2) of Example 1 were subcutaneously injected into 7 week-old BALB/cA nude mice (produced by CLEA Japan, Inc.). The sCA(2) particles were administered in a dose containing 40 µg of siRNA at each time. The total amount of the sCA(2) particles administered in this experiment was about twice the amount administered in the examination of the antitumor effect. The body weight of each mouse was measured over time. On day 20, tissues and blood were taken out of the mice and subjected to biochemical examination of blood and histological examination.

Figure 35:
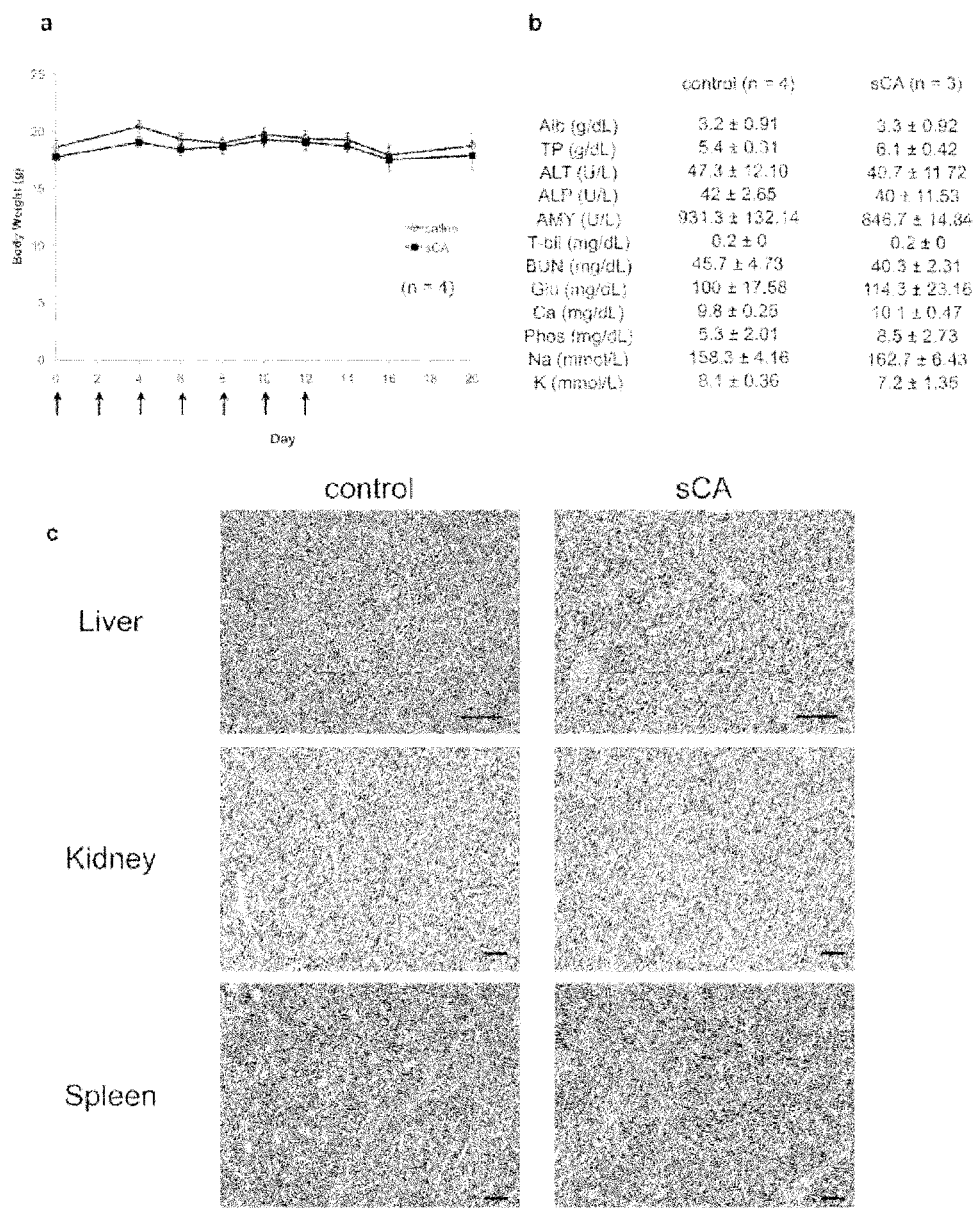
FIG. 35 shows the results of measurement of body weight, biochemical examination of blood, and histological examination performed on mice administered with carbonate apatite nanoparticles.

Part a of FIG. 35 shows the results of the measurement of the body weight of mice over time. Part a of FIG. 35 shows that the administration of the sCA(2) particles did not reduce the body weight. Part b of FIG. 35 shows the results of the biochemical examination of blood. The results show that even when the sCA(2) particle were administered, any physiologically significant difference from the control (administered with saline) was not observed. Part c of FIG. 35 shows the results of hematoxylin-eosin staining (HE staining) of the liver, kidney, and spleen. The results show that the administration of the sCA(2) particles did not cause any histological damage.

Example 15

Suppression of Aggregation of Carbonate Apatite Nanoparticles

Carbonate apatite nanoparticles were prepared as in the production (2) of Example 1. In this case, however, after the pellet of carbonate apatite nanoparticles was dissolved in an aqueous solution, 5 mg/ml of albumin was added to the solution, and the solution was subjected to the ultrasonic vibration treatment for 10 minutes. Distilled water or saline containing the carbonate apatite nanoparticles was placed in a 50 ml-volume tube (manufactured by BD Falcon). The tube was then allowed to float in water at 30° C. placed in the cleaning tank of an ultrasonic cleaner, in which the ultrasonic treatment was performed under the conditions of a high-frequency power of 55 W and an oscillating frequency of 38 kHz for 10 minutes. The controls used were carbonate apatite nanoparticles prepared by the same process with no addition of albumin and carbonate apatite particles prepared with no addition of albumin and with no ultrasonic vibration treatment. The size of the carbonate apatite nanoparticles prepared in these ways was measured in the same manner as in Example 2. The results are shown in Table 5 below and FIG. 36.

TABLE 5

Albumin-supplemented carbonate apatite nanoparticles

|  | After 1 minute | | After 10 minutes | |
| --- | --- | --- | --- | --- |
|  | Measurement 1 | Measurement 2 | Measurement 1 | Measurement 2 |
| Average particle size (nm) | 15.8 | 13.32 | 12.21 | 13.73 |
| Measured area | 5 μm × 5 μm | | 5 μm × 5 μm | |
| Number of particles in the measured area | 867 | 410 | 243 | 193 |

Figure 36:
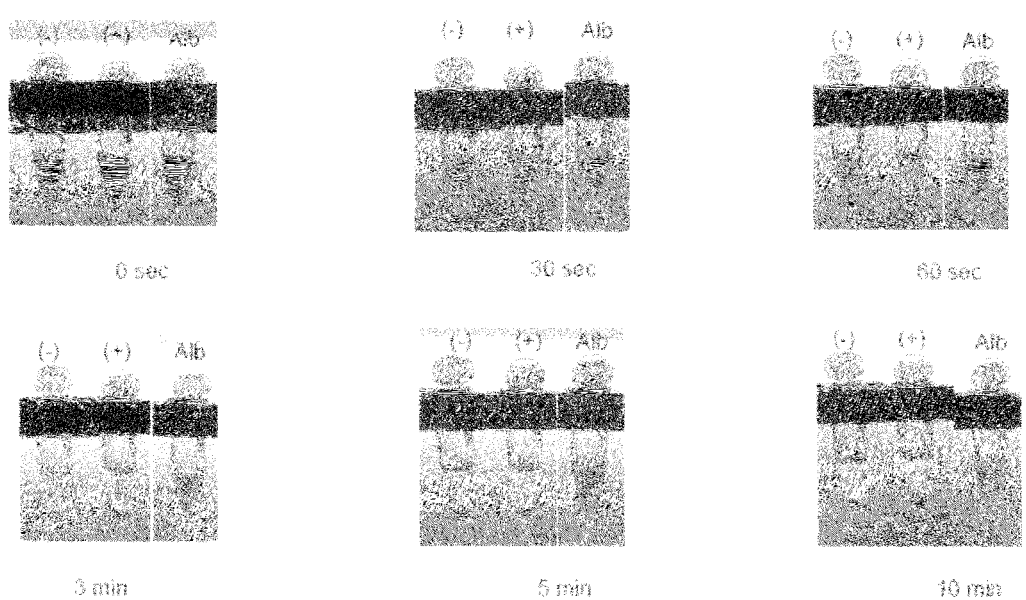
FIG. 36 shows that aggregation of carbonate apatite nanoparticles is suppressed by the addition of albumin, in which (−) represents the results in the case where no albumin was added and no ultrasonic treatment was performed, (+) represents the results in the case where no albumin was added but an ultrasonic vibration treatment was performed, and (Alb) represents the results in the case where albumin was added and an ultrasonic vibration treatment was performed.

Table 5 and FIG. 36 show that the addition of albumin to an aqueous solution containing carbonate apatite nanoparticles makes it possible to suppress reaggregation of the particles after the ultrasonic treatment. Although the mechanism of suppressing reaggregation of carbonate apatite nanoparticles by the addition of albumin has not been sufficiently clarified, it is conceivable that the surface of individual 10 nm-scale particles is coated with albumin so that reaggregation can be prevented. This may be because albumin is negatively charged to adhere to the positively-charged calcium site of carbonate apatite nanoparticles, so that calcium ions, which form the positively-charged site of carbonate apatite nanoparticles, can be prevented from being electrically coupled to negatively-charged sites of other particles, such as carbonate ions and phosphate ions.

Example 16 pH Sensitivity of Carbonate Apatite Nanoparticles

The sCA(2) particles, the sCA-siRNA particles, and the conventional type of carbonate apatite particles were prepared according to Example 1 and Comparative Example 1. After the centrifugation, the pellet of each type of particles was dissolved in 1 ml of a saline solution. While 1 N HCl was added dropwise to each sample, the turbidity of each sample at each reduced level of pH was evaluated as optical density by spectrophotometric analysis using a microplate reader (680XR manufactured by Bio-Rad Laboratories, Inc.). The pH was measured using Docu pH meter (manufactured by Sartorius AG) with a micro pH electrode (Microelectrodes, Inc.).

Figure 37:
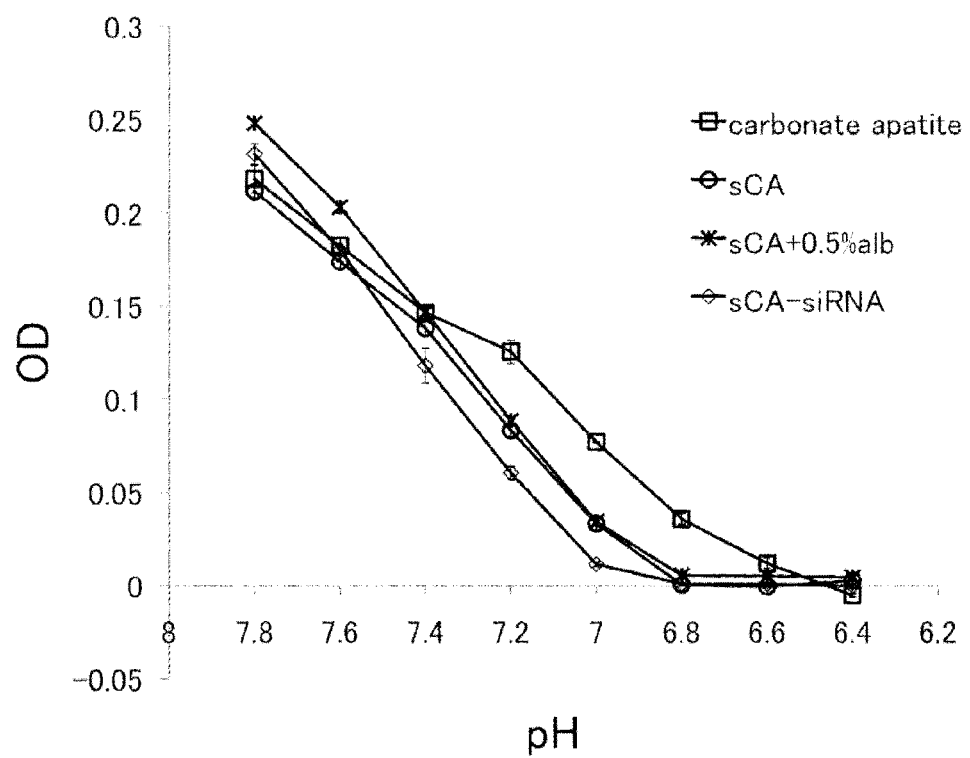
FIG. 37 shows the pH sensitivity of carbonate apatite nanoparticles in comparison with that of a conventional type of apatite particles.

The results are shown in FIG. 37. The results show that the carbonate apatite nanoparticles have higher pH sensitivity (in other words, the particles become more likely to disintegrate as pH decreases) than the conventional type of carbonate apatite particles. It is conceivable that this higher pH sensitivity is also responsible for the fact that the use of carbonate apatite nanoparticles improves the efficiency of uptake of substances into cells as compared with the use of the conventional type of carbonate apatite particles.

In the examples, 5'-AUCCGCGCGAUAGUACGUA-UUdTdT-3' (SEQ ID NO: 1) was used as the control siRNA to be labeled with 6-FAM, 5'-GCAUUCGUCCGGUUGCG-CUdTdT-3' (SEQ ID NO: 2) was used as the anti-survivin siRNA, and 5'-UACGUACUAUCGCGCGGAU-3' (SEQ ID NO: 3) was used as the control siRNA to be labeled with Alexa Fluor 750.

What is claimed is:

1. A pharmaceutical composition, comprising: carbonate apatite nanoparticles with an average particle size of at most 50 nm containing a nucleic acid with antitumor activity; and a pharmacologically acceptable solvent in which the carbonate apatite nanoparticles containing the nucleic acid are dispersed.

2. The pharmaceutical composition according to claim 1, wherein the solvent is a saline solution.

3. The pharmaceutical composition according to claim 1, wherein the carbonate apatite nanoparticles are a product obtained by subjecting, to an ultrasonic vibration treatment, carbonate apatite particles containing the nucleic acid with antitumor activity.

4. The pharmaceutical composition according to claim 1, wherein the nucleic acid is at least one selected from the group consisting of siRNA, miRNA, and antisense RNA.

5. The pharmaceutical composition according to claim 1, further comprising albumin.

6. A method of treating cancer, comprising the step of administering, to a patient with cancer, a pharmaceutical composition according to claim 1.

7. The method according to claim 6, wherein the pharmaceutical composition is administered by intravascular administration, subcutaneous administration, or intramuscular administration.

8. The method according to claim 6, wherein the solvent is a saline solution.

9. The method according to claim 6, wherein the carbonate apatite nanoparticles are a product obtained by subjecting, to an ultrasonic vibration treatment, carbonate apatite particles containing the nucleic acid with antitumor activity.

10. The method according to claim 6, wherein the nucleic acid is at least one selected from the group consisting of siRNA, miRNA, and antisense RNA.

11. The method according to claim 6, wherein the pharmaceutical composition further comprises albumin.

12. A method for manufacturing the pharmaceutical composition according to claim 1, comprising the steps of:
   preparing a dispersion including carbonate apatite particles containing a nucleic acid with antitumor activity and a pharmacologically acceptable solvent in which the particles are dispersed; and
   subjecting the dispersion to an ultrasonic vibration treatment.

* * * * *

SEQUENCE LISTING

```
<160> NUMBER OF SEQ ID NOS: 3

<210> SEQ ID NO 1
<211> LENGTH: 21
<212> TYPE: RNA
<213> ORGANISM: Artificial Sequence
<220> FEATURE:
<223> OTHER INFORMATION: siRNA

<400> SEQUENCE: 1
auccgcgcga uaguacguau u                                              21

<210> SEQ ID NO 2
<211> LENGTH: 19
<212> TYPE: RNA
<213> ORGANISM: Artificial Sequence
<220> FEATURE:
<223> OTHER INFORMATION: siRNA

<400> SEQUENCE: 2
gcauucgucc gguugcgcu                                                 19

<210> SEQ ID NO 3
<211> LENGTH: 19
<212> TYPE: RNA
<213> ORGANISM: Artificial Sequence
```

```
-continued

<220> FEATURE:
<223> OTHER INFORMATION: siRNA

<400> SEQUENCE: 3
uacguacuau cgcgcggau                                                        19
```